United States Patent
Aizenberg et al.

(10) Patent No.: US 9,683,197 B2
(45) Date of Patent: Jun. 20, 2017

(54) DYNAMIC AND SWITCHABLE SLIPPERY SURFACES

(71) Applicant: President and Fellows of Harvard College, Cambridge, MA (US)

(72) Inventors: Joanna Aizenberg, Boston, MA (US); Benjamin Hatton, Toronto (CA); Xi Yao, Cambridge, MA (US); Michael Aizenberg, Boston, MA (US); Wendong Wang, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 146 days.

(21) Appl. No.: 14/268,171

(22) Filed: May 2, 2014

(65) Prior Publication Data
US 2014/0328999 A1    Nov. 6, 2014

Related U.S. Application Data

(63) Continuation of application No. PCT/US2012/063609, filed on Nov. 5, 2012.
(Continued)

(51) Int. Cl.
*C10M 171/00* (2006.01)
*A61L 27/50* (2006.01)
(Continued)

(52) U.S. Cl.
CPC ........... *C10M 171/001* (2013.01); *A61F 2/28* (2013.01); *A61L 15/425* (2013.01); *A61L 15/50* (2013.01);
(Continued)

(58) Field of Classification Search
CPC ........ G03C 1/85; A61M 31/00; C10M 133/16
(Continued)

(56) References Cited

U.S. PATENT DOCUMENTS

| 5,624,713 A | 4/1997 | Ramer |
| 2005/0178286 A1* | 8/2005 | Bohn, Jr. ............ B81C 1/00206 106/16 |

(Continued)

FOREIGN PATENT DOCUMENTS

| DE | 19818956 A1 | 11/1998 |
| JP | 01-170932 A | 7/1989 |

(Continued)

OTHER PUBLICATIONS

Bohn et al., Insect Aquaplaning, Sep. 2004, PNAS, vol. 101 No. 39, pp. 14138-14143.*

(Continued)

*Primary Examiner* — Dah-Wei D Yuan
*Assistant Examiner* — Andrew Bowman
(74) *Attorney, Agent, or Firm* — Wilmer Cutler Pickering Hale and Dorr LLP

(57) ABSTRACT

The present disclosure describes a strategy to create self-healing, slippery liquid-infused porous surfaces (SLIPS) that can be modified as desired. Roughened (e.g., porous) surfaces can be utilized to lock in place a lubricating fluid, referred to herein as Liquid B to repel a wide range of objects, referred to herein as Object A (Solid A or Liquid A). Use of an external stimuli or degradation of the Liquid B can be utilized to change the characteristics of SLIPS structures reversibly or irreversibly that may be desired in a number of different applications. Numerous characteristics, such as adhesion, optical, mechanical, and the like, can be dynamically changed.

33 Claims, 64 Drawing Sheets

Related U.S. Application Data

(60) Provisional application No. 61/555,957, filed on Nov. 4, 2011.

(51) Int. Cl.

| | | |
|---|---|---|
| *A61L 29/14* | (2006.01) | |
| *A61L 15/50* | (2006.01) | |
| *A61L 27/56* | (2006.01) | |
| *A61L 15/42* | (2006.01) | |
| *A61F 2/28* | (2006.01) | |
| *B05D 3/00* | (2006.01) | |
| *B05D 3/02* | (2006.01) | |
| *B05D 3/06* | (2006.01) | |
| *B05D 3/12* | (2006.01) | |
| *B05D 3/14* | (2006.01) | |
| *F17D 1/08* | (2006.01) | |
| *A61M 31/00* | (2006.01) | |

(52) U.S. Cl.
CPC ............... *A61L 27/50* (2013.01); *A61L 27/56* (2013.01); *A61L 29/14* (2013.01); *A61L 29/146* (2013.01); *B05D 3/007* (2013.01); *B05D 3/0254* (2013.01); *B05D 3/06* (2013.01); *B05D 3/12* (2013.01); *B05D 3/14* (2013.01); *B05D 3/207* (2013.01); *F17D 1/08* (2013.01); *A61F 2240/001* (2013.01); *A61L 2400/10* (2013.01); *A61L 2400/16* (2013.01); *A61L 2400/18* (2013.01); *A61M 31/00* (2013.01); *Y10T 137/0324* (2015.04); *Y10T 428/139* (2015.01); *Y10T 428/24355* (2015.01)

(58) Field of Classification Search
USPC .............................. 106/16; 508/100; 424/422
See application file for complete search history.

(56) References Cited

U.S. PATENT DOCUMENTS

| | | | | |
|---|---|---|---|---|
| 2007/0254000 | A1* | 11/2007 | Guo | ...................... A61L 29/049 |
| | | | | 424/422 |
| 2009/0069203 | A1* | 3/2009 | Takezaki | .............. C10M 115/08 |
| | | | | 508/100 |

FOREIGN PATENT DOCUMENTS

| | | |
|---|---|---|
| JP | 05-240251 A | 9/1993 |
| JP | 2004-037764 A | 2/2004 |
| WO | WO-93/17077 A1 | 9/1993 |
| WO | WO-99/36490 A1 | 7/1999 |
| WO | WO-2006/091235 A1 | 8/2006 |

OTHER PUBLICATIONS

Bauer, U. and Federle, W., "The insect-trapping rim of Nepenthes pitchers," Plant Signaling and Behavior, vol. 4, No. 11, pp. 1019-1023 (Nov. 2009).

Bohn, H. F. and Federle, W., "Insect aquaplaning: Nepenthes pitcher plants capture prey with the peristome, a fully wettable water-lubricated anisotropic surface," PNAS, vol. 101, No. 39, pp. 14138-14143 (Sep. 28, 2004).

Cassie, A. B. D. and Baxter, S., "Wettability of porous surfaces," Transaction of the Faraday Society, vol. 40, pp. 546-551 (1944).

Hejazi, V. and Nosonovsky, M., "Wetting Transitions in Two-, Three-, and Four-Phase Systems," Langmuir, vol. 28, pp. 2173-2180 (2012).

International Search Report and Written Opinion issued by the European Patent Office as International Searching Authority for International Application No. PCT/US2012/021928 dated Aug. 10, 2012 (21 pages).

International Search Report and Written Opinion issued by the European Patent Office as International Searching Authority for International Application No. PCT/US2012/021929 dated Aug. 21, 2012 (23 pages).

International Search Report and Written Opinion issued by the European Patent Office as International Searching Authority for International Application No. PCT/US2012/063609 dated Sep. 9, 2013 (26 pages).

Lafuma, A. and Quere, D., "Slippery pre-suffused surfaces," Europhysics Letters: A Letters Journal Exploring the Frontiers of Physics, vol. 96, No. 5, 56001, pp. 1-4 (Dec. 2011).

Wenzel, Robert N., "Resistance of Solid Surfaces to Wetting by Water," Industrial & Engineering Chemistry, vol. 28, No. 8, pp. 988-994 (Aug. 1936).

Wong, T.-S. et al., "Bioinspired self-repairing slippery surfaces with pressure-stable omniphobicity," Nature, vol. 477, pp. 443-447 (Sep. 22, 2011).

Yao, X. et al., "Applications of Bio-Inspired Special Wettable Surfaces," Advanced Materials, vol. 23, pp. 719-734 (2011).

* cited by examiner

Poking

DYNAMIC AND SWITCHABLE SLIPPERY SURFACES

RELATED APPLICATIONS

This application is a continuation of PCT Application No. US2012/063609, filed on Nov. 5, 2012 which claims the benefit of the earlier filing date of U.S. Patent Application No. 61/555,957, filed on Nov. 4, 2011, the contents of which is incorporated by reference herein in their entireties.

This application is related to International Patent Application No. PCT/US12/21928, filed on Jan. 19, 2012; International Patent Application No. PCT/US12/21929, filed on Jan. 19, 2012; U.S. Patent Application No. 61/434,217, filed on Jan. 19, 2011; 61/466,352, filed on Mar. 22, 2011; U.S. Patent Application No. 61/470,973, filed on Apr. 1, 2011; U.S. Patent Application No. 61/496,883, filed on Jun. 14, 2011; U.S. Patent Application No. 61/509,488, filed on Jul. 19, 2011; and U.S. Patent Application No. 61/529,734, filed on Aug. 31, 2011, the contents of which are incorporated by reference herein in their entireties.

STATEMENT REGARDING GOVERNMENT FUNDING

This invention was made with government support under N66001-11-1-4180 and FA9550-09-1-0669-DOD35CAP awarded by the U.S. Department of Defense. The government has certain rights in the invention.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present disclosure relates generally to slippery surfaces that controllably change their structure and the associated slippery and other properties over time, methods for forming them, and their uses.

SUMMARY

The present disclosure relates generally to slippery surfaces that controllably change their structure and the associated slippery and other properties over time, methods for forming them, and their uses.

In one aspect, a method of altering one or more characteristics of a structure is disclosed, the method comprising: providing a structure comprising a roughened surface which is optionally functionalized to immobilize a lubricating liquid, wherein the lubricating liquid wets and adheres to the roughened surface to form a layer having a smooth planar upper surface over the roughened surface to obtain a first characteristic of the structure; and applying or removing a first stimulus to the structure, wherein the application or removal of the first stimulus exposes a portion of the underlying substrate or disrupts the smoothness and/or planarity and/or planarity of the upper surface of the lubricating liquid layer to obtain a second characteristic of the structure.

In some embodiments, the one or more characteristics comprise at least one of optics, transparency, wettability, adhesion to a first substance which optionally contacts the surface, repellency of a first liquid which optionally contacts the surface or mobility of a first liquid which optionally contacts the surface.

In some embodiments, the change from the first characteristic of the structure to the second characteristic of the structure occurs gradually or over a continuum.

In some embodiments, the change from the first characteristic of the structure to the second characteristic of the structure occurs abruptly or completely.

In some embodiments, the change from the first characteristic of the structure to the second characteristic of the structure is irreversible or reversible, by removal or reduction of the first stimulus or application of a second stimulus.

In some embodiments, the first stimulus is selected to alter the shape, volume or configuration of the substrate, such that the underlying substrate is exposed when the substrate is in an expanded or contracted state.

In some embodiments, the substrate comprises a shape-changing polymer selected from the group consisting of thermal responsive polymers that undergo a shape, volume or configuration change upon thermal stimulus or a change in pH, hydration, humidity or exposure to solvent, optical responsive polymers that undergo a shape, volume or configuration change upon light stimulus, electro-activated polymer that undergo a shape, volume or configuration change upon electric field stimulus and ferrogels that undergo a shape, volume or configuration change upon magnetic field stimulus.

In some embodiments, the substrate is a deformable roughened surface and the first stimulus comprises mechanical deformation, said mechanical deformation exposing the underlying substrate.

In some embodiments, the substrate is a deformable roughened surface and the first stimulus comprises mechanical deformation, said mechanical deformation smoothing out the roughed surface to cover the underlying substrate.

In some embodiments, the substrate comprises a conductive element and the first stimulus comprises an electrical current.

In some embodiments, the lubricating liquid comprises additives that respond to the first stimulus.

In some embodiments, the additives comprise magnetic particles and the first stimulus comprises a magnetic field.

In some embodiments, the additives comprise electrically conductive particles and the first stimulus comprises a electric field.

In some embodiments, the additives comprises a gelling or polymerization agent and the first stimulus induces polymerization or gelling of the lubricant.

In some embodiments, the first stimulus comprises heat.

In some embodiments, the heat stimulus causes temperature-induced melting of a solid lubricant or a change in viscosity of the lubricant.

In some embodiments, the first stimulus comprises a biological environment.

In some embodiments, the surface comprises a plurality of deflectable aspected features and the first stimulus is selected to deflect the aspected features from a first position in which the aspected features are above the lubricant layer to a second position in which the aspected features are below the lubricant layer or vice versa.

In some embodiments, the first stimulus is selected to degrade the substrate surface to reduce the affinity of the lubricant for the surface.

In some embodiments, the first stimulus is selected to degrade the lubricant to reduce the affinity of the lubricant for the surface.

In some embodiments, the first stimulus is selected to reduce the shape, volume or configuration of the lubricant to expose the underlying substrate.

In some embodiments, the removal of the first stimulus and/or the application of a second stimulus re-obtains the first characteristic of the structure.

In another aspect, a method to control the flow of a fluid without using a valve is disclosed, the method comprising: providing a region on a substrate that comprises a roughened surface which is optionally functionalized to immobilize a lubricating liquid under a first set of conditions; providing the lubricating liquid, wherein the lubricating liquid wets and adheres to the roughened surface to form a layer having a smooth planar upper surface over the roughened surface to obtain a slippery channel under the first set of conditions; flowing a fluid through or along the region; applying or removing a second set of conditions; wherein the second set of conditions comprises at least one stimulus which exposes the substrate or disrupts the smoothness and/or planarity of the upper surface of the lubricating liquid to obtain a non-slippery channel and stop or reduce the flow of the fluid through or along the region.

In another aspect, a method to change the adhesive properties of a medical implant is disclosed, the method comprising: providing a medical implant that comprises a roughened surface which is optionally functionalized to immobilize a lubricating liquid under a first set of conditions; providing a lubricating liquid, wherein the lubricating liquid wets and adheres to the roughened surface to form a smooth planar upper surface over the roughened surface to obtain a slippery medical implant under the first set of conditions; wherein the slippery medical implant repels undesired biological objects; and wherein the lubricating liquid is capable of degrading or moving away from the medical implant to expose the roughened surface and promote adhesion of desired biological objects under a second set of conditions.

In some embodiments, the undesired biological objects comprise at least one of bacteria or biofilm.

In some embodiments, the desired biological objects comprise at least one of bone tissue or cells.

In another aspect, a structure is disclosed, comprising: a substrate comprising a roughened surface which is optionally functionalized to immobilize a lubricating liquid under a first set of conditions; and a lubricating liquid, wherein the lubricating liquid wets and adheres to the roughened surface to form a layer having a smooth planar upper surface over the roughened surface to obtain a slippery surface under the first set of conditions; wherein the substrate comprises a material that is capable of changing the shape, volume or configuration of the roughened surface to allow a change in the level of the lubricating liquid upon application or removal of at least one stimulus.

In some embodiments, the at least one stimulus comprises at least one of mechanical force, electric field, magnetic field, pH, biological fluids, hydration, humidity, solvent, acoustic signals or temperature.

In another aspect, a structure is disclosed, comprising: a substrate that comprises a roughened surface which is optionally functionalized to immobilize a lubricating liquid under a first set of conditions; and a lubricating liquid, wherein the lubricating liquid wets and adheres to the roughened surface to form a layer having a smooth planar upper surface over the roughened surface to obtain a slippery surface under a first set of conditions; wherein the lubricating liquid comprises a material that is capable of changing the phase, shape or viscosity of the lubricating liquid upon application or removal of at least one stimulus.

In some embodiments, the material comprises magnetic particles.

In some embodiments, the lubricating liquid solidifies upon application or removal of the at least one stimulus.

In some embodiments, the at least one stimulus comprises at least one of an electric field, a magnetic field, pH, biological fluids, acoustic signals, humidity, hydration, solvent or temperature.

In another aspect, an article capable of changing properties is disclosed, comprising: a structure comprising a roughened surface which is optionally functionalized to immobilize a lubricating liquid, wherein the lubricating liquid wets and adheres to the roughened surface to form a layer having a smooth planar upper surface over the roughened surface to obtain a first characteristic of the structure; wherein the lubricating liquid exposes a portion of the underlying substrate or disrupts the smoothness and/or planarity of the upper surface of the lubricating liquid in response to application or removal of a first stimulus to obtain a second characteristic of the structure.

In some embodiments, the first stimulus comprises at least one of active removal, evaporation or decomposition of the lubricating liquid.

In some embodiments, application or removal of the first stimulus results at least in part in a change in degree of swelling of the roughened surface.

In some embodiments, the first stimulus comprises stretching, bending, shearing or poking the roughened surface so as to expose a portion of the underlying substrate.

In some embodiments, the roughened surface comprises a hydrogel or organogel and the first stimulus comprises at least one of mechanical forces, temperature, pH, optical response, humidity, hydration, solvent, M-field, E-field, electrical current, glucose, enzyme, antigen or ultrasound.

In some embodiments, the roughened surface comprises electro-activated gels or polymers and the first stimulus comprises an electric field.

In some embodiments, the roughened surface comprises a ferrogel and the first stimulus comprises a magnetic field.

In some embodiments, the first stimulus comprises a magnetic field which causes the lubricating liquid to expand.

In some embodiments, the roughened surface comprises a conductive element and the first stimulus comprises an electrical current.

In some embodiments, the roughened surface comprises a mesh and the electrical current causes the mesh to expand or contract.

In some embodiments, the roughened surface comprises a plurality of deflectable aspected features and the stimulus is selected to deflect the aspected features from a first position in which the aspected features are above the lubricant layer to a second position in which the aspected features are below the lubricant layer or vice versa.

In some embodiments, the first stimulus results in solidification of the lubricating liquid to obtain the second characteristic of the structure; and wherein the first characteristic of the structure is re-obtained by removal or reduction of the first stimulus or the application of a second stimulus.

In some embodiments, the application and removal of the first stimulus tunes the viscosity of the lubricating liquid along a continuum.

In some embodiments, the lubricating liquid comprises a ferrofluid or ferromagnetic particles and the first stimulus comprises a magnetic field.

In some embodiments, the article comprises a channel or pipe and wherein the lubricating liquid wets and adheres to the inner surface of the channel or pipe.

In some embodiments, the transition from a layer having a smooth planar upper surface to an exposed portion of the underlying substrate or disrupted smoothness and/or planarity of the upper surface of the lubricating liquid is reversible or irreversible.

In some embodiments, application of a second stimulus re-obtains the first characteristic of the structure.

In some embodiments, the second stimulus comprises removing the first stimulus.

In some embodiments, the application and removal of the first and second stimuli tunes the first and second characteristics of the structure along a continuum.

In some embodiments, the application and removal of the first and second stimuli tunes the viscosity of the lubricating liquid along a continuum.

In some embodiments, the roughened surface comprises a chemical catalyst.

In some embodiments, the article is a tent, fluidic channel, wound dressing or bandage.

In some embodiments, the at least one of the first or second stimuli changes a property selected from optics, transparency, wettability, adhesion to a first substance, repellency of a first liquid or mobility of a first liquid.

In some embodiments, the functionalization of the surface comprises chemical functionalization, porosity or roughness.

In some embodiments, the article is patterned such that responsive regions are created which respond to local stimulus, or such that the change from the first to the second characteristic occurs locally.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
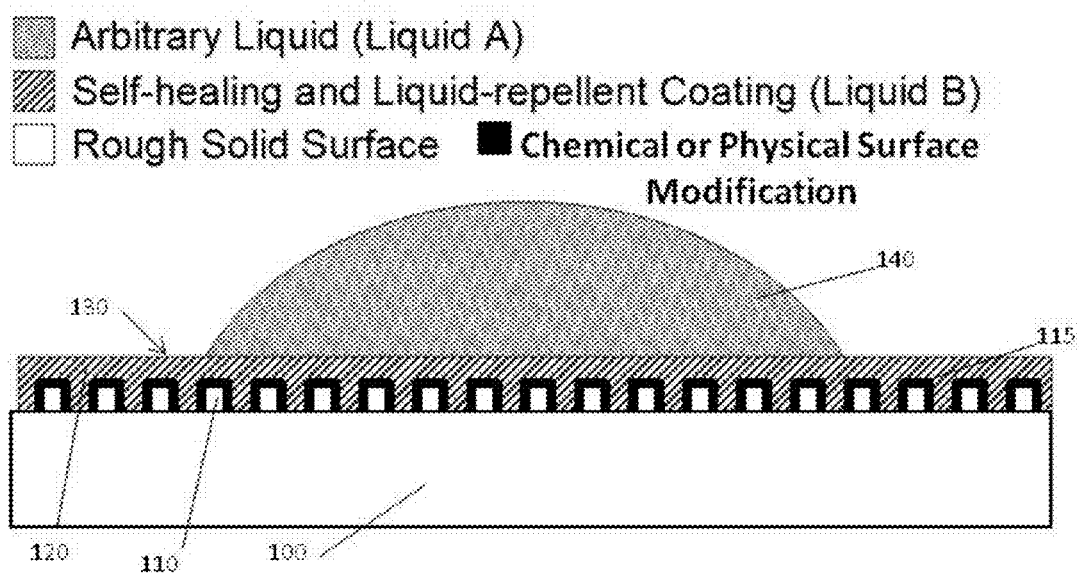
FIG. 1 is a schematic of a self-healing slippery liquid-infused porous surface (SLIPS) in accordance with certain embodiments.

The present disclosure describes slippery surfaces referred to herein as Slippery Liquid-Infused Porous Surfaces ("SLIPS") that changes its slippery characteristics based on certain variables, such as time, external stimuli, and the like.

In certain embodiments, SLIPS exhibits anti-adhesive and anti-fouling properties. SLIPS are able to prevent adhesion of a wide range of materials. Exemplary materials that do not stick onto the surface include liquids, solids, and gases (or vapors). In some embodiments, liquids such as oil-based paints, hydrocarbons, organic solvents, complex fluids such as protein-containing fluids and the like are repelled. In some embodiments, the liquids are either pure liquids and complex fluids. In certain embodiments, SLIPS is designed to be omniphobic, where SLIPS exhibits both hydrophobic and oleophobic properties. In some embodiments, biological objects like bacteria, insects, fungi and the like are repelled. In further embodiments, solids like paper, sticky notes, or inorganic particle-containing paints, dust particles are repelled or cleaned. In still further embodiments, solids like ice and frost are repelled. In some embodiments, SLIPS is also designed to show high transparency that avoids scattering of light in the material. Yet another characteristic of SLIPS is their ability to self-heal and function in extreme conditions, such as high pressure.

In certain embodiments, a surface is designed to change or reduce any of the characteristics of the SLIPS described above. In some embodiments, a surface is designed to provide the low adhesion, high repellency and transparency surfaces of SLIPS for a specified amount of time or under specific conditions. In some embodiments, the SLIPS structure is altered to revert to a surface with conventional wetting, high adhesion or low repellency behavior. In some embodiments, the SLIPS structure is designed to change its optical properties or self-healing characteristics. Because the SLIPS properties are changeable based on user design, such surfaces are referred to as "dynamic SLIPS". In some embodiments, SLIPS is modified to obtain a structure that promotes adhesions, or change transparency, hereinafter referred to as a "non-SLIPS," under selected conditions. By modifying the structure of SLIPS, materials that did not adhere to SLIPS are made to adhere onto the modified surface or change its appearance, for example optical property from transparent to opaque.

In certain embodiments, the dynamic nature of the SLIPS surface is either permanent or reversible. In some embodiments, a dynamic SLIPS provides a change over time from a highly repellent to an adhesive surface. In some embodiments, the newly adhesive surface is permanent. In other embodiments, it is desirable to oscillate between conditions of high repellency and adhesion. Dynamic SLIPS is capable of reversibly changing its surface properties or appearance. In certain embodiments, dynamic switching of a SLIPS structure to a non-SLIPS structure is desired to occur on the time scale of seconds, minutes, days, weeks, months, or even years. In some embodiments, dynamic SLIPS is designed to switch between the SLIPS and non-SLIPS states either abruptly or in a continuous fashion, enabling fine tuning of the surface properties between two extreme conditions.

It should be noted that while adhesion and optical transparency are particularly discussed, in some embodiments other characteristics, such as the ability to lower friction, ability to prevent solidification on its surface, ability to repel solid or liquid objects, and the like are be dynamically altered as the transition between SLIPS and non-SLIPS structures occur.

Materials that can be prevented from sticking to SLIPS or promoted to stick onto non-SLIPS are referred to herein as "Object A." Object A that is in liquid form is referred to as "Object A in liquid form," or "liquefied Object A," or "Liquid A." Object A that is in solid form is referred to as "Object A in solidified form," or "solidified Object A" or "Solid A." Object A that is in gas form is referred to a "Object A in gas form," or "gaseous Object A" or "Gas A." In certain embodiments, Object A contains a mixture of solids, liquids, and/or gases.

In some embodiments, Object A includes polar and non-polar Liquids A and their solidified forms, such as hydrocarbons and their mixtures (e.g., from pentane up to hexadecane and mineral oil, paraffinic extra light crude oil; paraffinic light crude oil; paraffinic light-medium crude oil; paraffinic-naphthenic medium crude oil; naphthenic medium-heavy crude oil; aromatic-intermediate medium-heavy crude oil; aromatic-naphthenic heavy crude oil, aromatic-asphaltic crude oil, etc.), ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), acids (e.g., concentrated hydrofluoric acid, hydrochloric acid, nitric acid, etc.) and bases (e.g., potassium hydroxide, sodium hydroxide, etc.), and ice, etc. In some embodiments, Object A includes biological objects, such as insects, small animals, protozoa, bacteria, viruses, fungi, bodily fluids (e.g., blood) and tissues, proteins and the like. In some embodiments, Object A includes solid particles suspended in liquid. In some embodiments, Object A includes non-biological objects, such as dust, colloidal suspensions, spray paints, food items, common household, and the like. In some embodiments, Object A includes adhesives and adhesive films. The list is intended to be exemplary and the slippery surfaces of the present disclosure are envisioned to successfully repel numerous other types of materials.

A schematic of the overall design of SLIPS is illustrated in FIG. 1. As shown, the article includes a solid surface 100 having surface features 110 that provide a certain roughness (i.e., roughened surface). The surface features 110 are chemically or physically modified when needed with a layer 115 to ensure high affinity to a Liquid B 120 applied thereon. Liquid B stably wets the roughened surface, filling the hills, valleys, and/or pores of the roughened surface, and forming an ultra-smooth surface 130 over the roughened surface. In some embodiments, in its repellant state, SLIPS possesses an ultra-smooth surface resulting from wetting the roughened surface with Liquid B, and Object A 140 does not adhere to and moves freely on the surface.

In some embodiments, SLIPS is modified to obtain non-SLIPS structures. In some embodiments, the SLIPS surface is modified such that it exposes the underlying roughened surface and thereby disrupts the ultra-smooth surface. In some embodiments, the roughened surface is functionalized to immobilize a liquid. In other embodiments, the liquid surface itself is disrupted in order to disturb the ultra-smooth surface created by the wetting of the roughened surface. Many different techniques, such as active removal of Liquid B, Liquid B evaporation or decomposition with time, application of certain external stimuli (e.g., stretching, compression, etc.) to the underlying solid surface 100, swelling and de-swelling of the solid surface in response to certain stimuli, choosing the solid surface to decompose or smoothen during the operation, application of certain external stimuli (e.g., mechanical, thermal, electrical, magnetic, acoustic, etc.) to Liquid B, temperature-induced solidification/melting of Liquid B or dynamic changes of its viscosity, slow release of occluded Liquid B droplets from the solid, and the like are carried out to regulate SLIPS or non-SLIPS properties.

Figure 2:
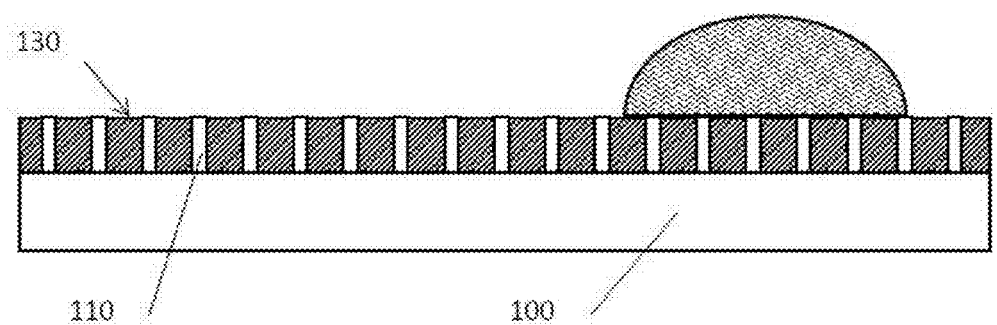
FIG. 2 is a schematic of a non-SLIPS structure obtained by modifying the underlying substrate in accordance with certain embodiments.
Figure 3:
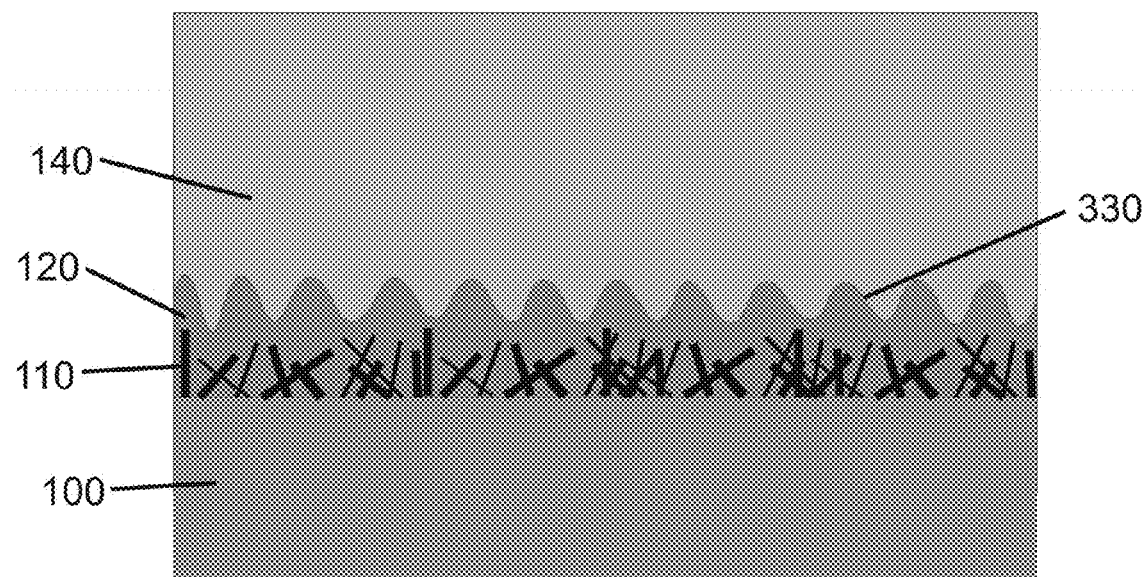
FIG. 3 is a schematic of a non-SLIPS structure obtained by modifying Liquid B of the SLIPS structure in accordance with certain embodiments.

For example, as shown in FIG. 2, Liquid B recedes toward the solid surface 100 (e.g., evaporation, stretching of the underlying solid surface 100) to expose the surface features 110, removing the ultra-smooth surface 130 that is characteristic of SLIPS. In some embodiments, Liquid B is modified to impart a non-ultra-smooth surface 330 as shown in FIG. 3.

SLIPS

Before describing in detail the particular components of a dynamic SLIPS structure, the underlying components of SLIPS are discussed. Further detail is found in related International Patent Application No. PCT/US12/21928, filed on Jan. 19, 2012; International Patent Application No. PCT/US12/21929, filed on Jan. 19, 2012; U.S. Patent Application No. 61/434,217, filed on Jan. 19, 2011; 61/466,352, filed on Mar. 22, 2011; U.S. Patent Application No. 61/470,973, filed on Apr. 1, 2011; U.S. Patent Application No. 61/496,883, filed on Jun. 14, 2011; U.S. Patent Application No. 61/509,488, filed on Jul. 19, 2011; U.S. Patent Application No. 61/529,734, filed on Aug. 31, 2011; and U.S. Patent Application No. 61/673,705, filed on Jul. 19, 2012, the contents of which are incorporated by reference in their entireties.

SLIPS includes at least the following three factors: 1) the lubricating liquid (Liquid B) can infuse into, wet, and stably adhere within the properly functionalized roughened surface, 2) the roughened surface can be preferentially wetted by the lubricating liquid (Liquid B) rather than by the liquid to be repelled (Object A), and 3) the lubricating fluid (Liquid B) and the object or liquid to be repelled (Object A) are immiscible and do not chemically interact with each other.

The first factor can be satisfied by using micro- or nanotextured, rough substrates whose large surface area, combined with chemical affinity for Liquid B, facilitates complete wetting by, and adhesion of, the lubricating fluid. More specifically, the roughness of the roughened surface, R, is selected such that $R \geq 1/\cos \theta_{BX}$, where R is defined as the ratio between the actual and projected areas of the surface, and $\theta_{BX}$ is the equilibrium contact angle of Liquid B on a flat solid substrate immersed under medium X (X=water/air/other immiscible fluid medium). In certain embodiments, R may be any value from 1 (essentially flat, smooth surface) to greater than 1, such as 1.5, 2, or even 5 and higher. To satisfy the first requirement, the roughened surface should be chemically or physically modified with moieties that strongly interact with Liquid B, such that this lubricant liquid stably adheres to and is locked in place by the modified solid substrate. The methods, structures and articles disclosed herein can comprise any degree of roughness.

To satisfy the second factor, the roughened surface can be preferentially wetted by the lubricating fluid (Liquid B) rather than by the immiscible liquid/complex fluids/undesirable solids one wants to repel (Object A). This can ensure that Object A remains on top of a stable lubricating film of Liquid B and does not infuse to get attached to the underlying solid.

To satisfy the third factor, the enthalpy of mixing between Object A and Liquid B may be sufficiently high (e.g., water/oil; insect/oil; ice/oil, etc.) that they phase separate from each other when mixed together, and/or do not undergo substantial chemical reactions between each other. In certain embodiments, Object A and Liquid B are substantially chemically inert with each other so that they physically remain distinct phases/materials without substantial mixing between the two.

Figures 4A, 4B:
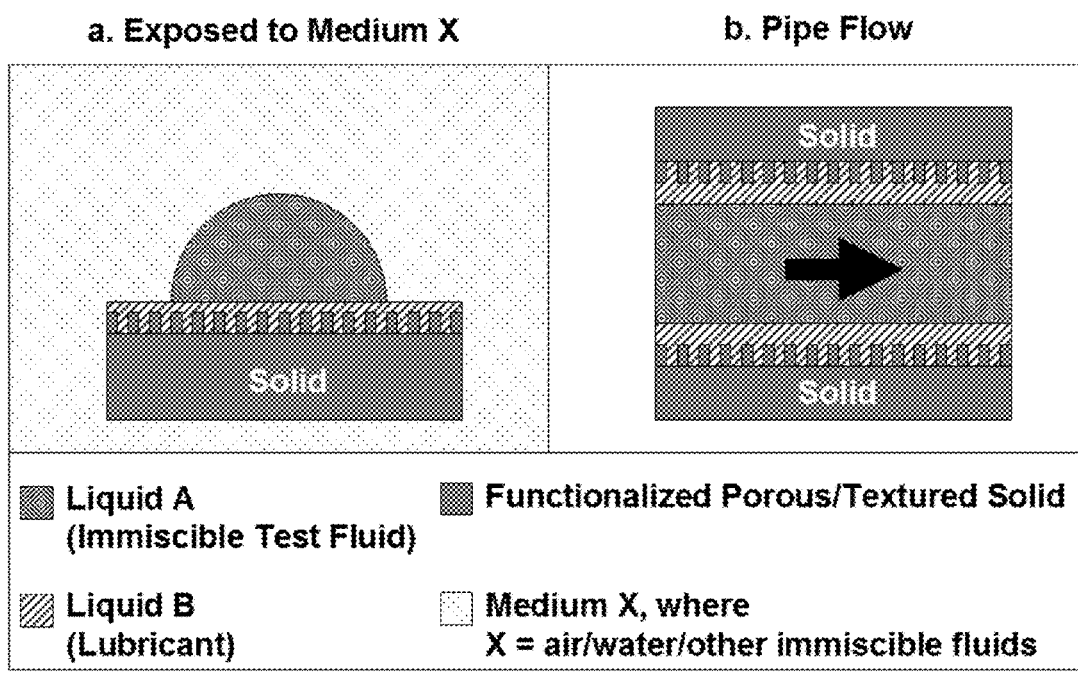
FIG. 4A shows Liquid A droplet over SLIPS where Liquid B of the SLIPS is exposed to both Liquid A and immiscible Medium X in accordance with certain embodiments.
FIG. 4B shows Liquid A contacting SLIPS where Liquid B of the SLIPS is substantially exposed only to Liquid A in accordance with certain embodiments.

In some embodiments, SLIPS is incorporated in an environment (1) where Liquid B is exposed substantially only to Object A (e.g., flow pipe, etc.) (see FIG. 4B) or (2) where Liquid B is exposed to both Object A and another fluid environment, such as medium X (e.g., atmosphere, underwater, etc.) (see FIG. 4A). FIG. 4 shows Object A in the liquid form as Liquid A.

When SLIPS is incorporated in the first environment (e.g., inside the interior of a pipe/tubing and alike) (see FIG. 4B), the working combinations of the substrate surface/lubricant/immiscible test fluid may be chosen by satisfying the condition shown in Equation (e1)

$$\Delta E_0 = \gamma_{BX} \cos \theta_{BX} - \gamma_{AX} \cos \theta_{AX} > 0 \quad (e1)$$

where $\gamma_{AX}$, and $\gamma_{BX}$ represent the interfacial energies of the Object A-medium X interface, and Liquid B-medium X interface, respectively. Also, $\theta_{AX}$, and $\theta_{BX}$ are the equilibrium contact angles of Object A and Liquid B on a flat solid surface immersed under medium X environment, respectively.

On the other hand, when SLIPS is incorporated in the second environment (e.g., exposed to both Liquid A and a second fluid or air environment) (see FIG. 4A), satisfying the following two conditions can provide a suitable SLIPS $$\Delta E_1 = R(\gamma_{BX} \cos \theta_{BX} - \gamma_{AX} \cos \theta_{AX}) - \gamma_{AB} > 0 \quad (e2)$$

$$\Delta E_2 = R(\gamma_{BX} \cos \theta_{BX} - \gamma_{AX} \cos \theta_{AX}) + \gamma_{AX} - \gamma_{BX} > 0 \quad (e3)$$

where $\gamma_{AB}$ represent the interfacial energies of the Object A-Liquid B interface.

In addition, in some embodiments the density difference between the Object A and Medium X also plays a role for the liquid repellency. For example, in order for Object A to slide off from SLIPS by gravity, the density of Object A, $\rho_A$, may desirably be greater than that of the Medium X, $\rho_X$ (i.e., $\rho_A > \rho_X$). Moreover, the size of Object A may be on the order of, or greater than, its capillary length. Specifically, capillary length is a characteristic length scale that quantifies the dominance of body force over surface force on an object, which can be quantitatively expressed as $(\gamma/\rho g)^{1/2}$, where $\gamma$, $\rho$, and g are surface tension, density of the liquid, and gravity, respectively.

The different parameters noted in (e1), (e2) and (e3) (i.e. $\theta_{AX}$, $\theta_{BX}$, $\gamma_{AX}$, $\gamma_{BX}$, $\gamma_{AB}$, R) can be obtained or estimated utilizing the following standard techniques. While the following standard techniques are described, other techniques are utilized in accordance with the present disclosure, which will be apparent to those of skill in the art.

Kinetically Stable SLIPS

In certain embodiments, kinetically stable SLIPS, which are stable for a limited period of time and/or for limited number of exposures to the liquid(s) being repelled, are utilized, as described in U.S. Patent Application No. 61/673,705, filed on Jul. 19, 2012, the contents of which is incorporated by reference herein in its entirety.

Figure 4C:
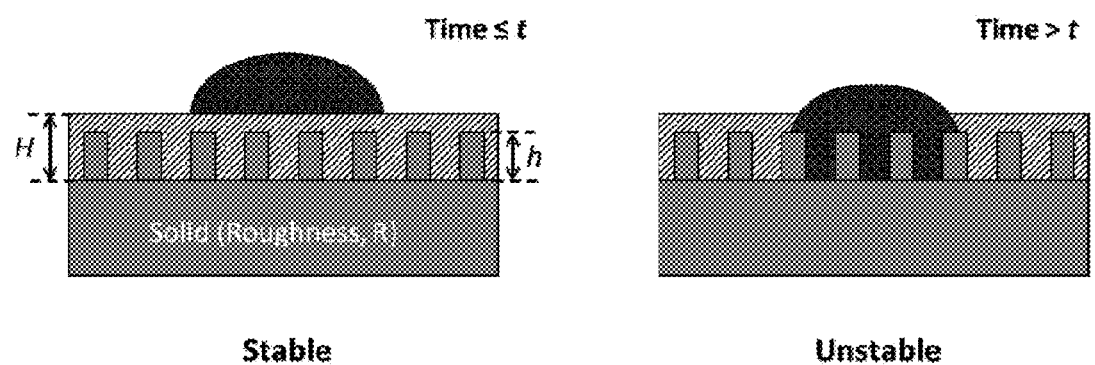
FIG. 4C shows metastable SLIPS in accordance with certain embodiments.

In some instances, even though the thermodynamic energy minimum is not reached based on the equations described above, if the lubricating liquid (Liquid B)'s surface tension allows wetting of the roughened surface, kinetically stable SLIPS may be formed for operationally meaningful time scale (FIG. 4C, left), although over long periods time, the SLIPS structure may degrade (FIG. 4C, right). As shown in FIG. 4C, Object A displaces Liquid B after a sufficiently long time leading to an unstable or non-SLIPS structure. However, before this degradation takes place, the kinetically stable SLIPS structure (FIG. 4C, left) is utilized as a basis for a dynamic SLIPS structure.

In certain embodiments, a kinetically stable SLIPS structure that degrades after more than a few minutes, hours, or even days may be utilized if the dynamic switching of a SLIPS structure to a non-SLIPS structure is desired to occur on the time scale of several seconds or less. Similarly, a kinetically stable SLIPS structure that degrades after more than a few hours or days may be utilized if the dynamic switching of a SLIPS structure to a non-SLIPS structure is desired to occur on the time scale of several minutes or less.

In certain embodiments, a kinetically stable SLIPS structure that degrades after more than a few days or weeks is utilized if the dynamic switching of a SLIPS structure to a non-SLIPS structure is desired to occur on the time scale of several hours or less. In certain embodiments, a kinetically stable SLIPS structure that degrades after more than a few weeks or months is utilized if the dynamic switching of a SLIPS structure to a non-SLIPS structure is desired to occur on the time scale of several days or weeks. In certain embodiments, a kinetically stable SLIPS structure that degrades after more than a few months or years is utilized if the dynamic switching of a SLIPS structure to a non-SLIPS structure is desired to occur on the time scale of several weeks or months.

Non-SLIPS

In some embodiments, SLIPS is modified to obtain non-SLIPS structures. In some embodiments, non-SLIPS structures are formed by controlling and/or modifying the underlying solid surface 100. In further embodiments, non-SLIPS structures are formed by controlling and/or modifying Liquid B. In still further embodiments, both the solid surface and the Liquid B undergo changes to obtain non-SLIPS structures. In some embodiments, structures switch between SLIPS and non-SLIPS states. In further embodiments, structures are continuously tuned so as to have more or less SLIPS character.

Modification of the Underlying Solid Surface

In certain embodiments, the underlying solid surface 100 is modified. In some embodiments, the underlying surface area and available volume for Liquid B increase so that Liquid B recedes toward the solid surface 100 to expose the roughened surface 110.

Figure 5A:
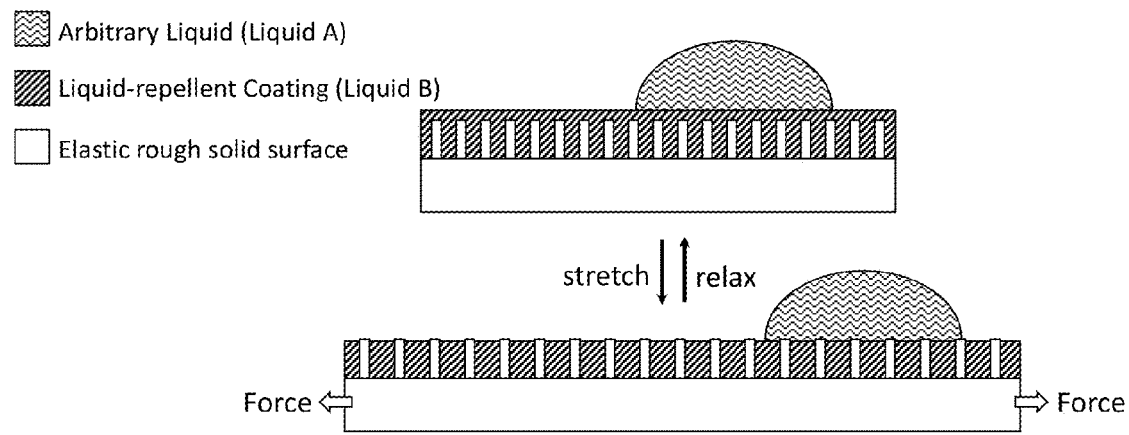
FIG. 5A shows a change from SLIPS to a non-SLIPS structure as a function of applied mechanical strain in accordance with certain embodiments.

Many different techniques for receding Liquid B and exposing the roughened surface 110 can be envisioned. For example, as shown in FIG. 5A, Liquid B recedes toward the elastic (e.g., stretchable) solid surface 100 by applying a mechanical force to stretch the underlying solid surface 100 and expose the roughened surface 110. In such embodiments, the substrate is selected to be flexible and capable of deformation (in addition to requirements set out above for obtaining SLIPS).

Figure 5B:
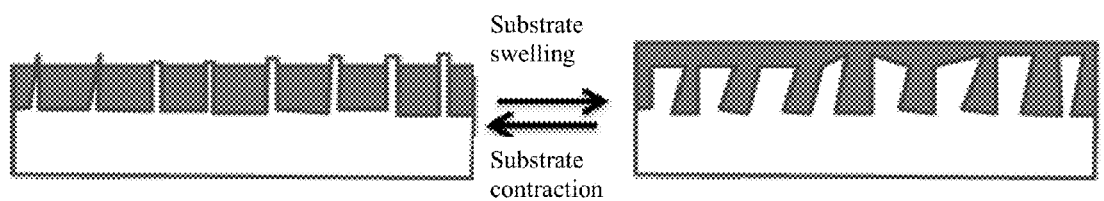
FIG. 5B shows a change from non-SLIPS to a SLIPS structure as a function of swelling of the substrate to squeeze Liquid B to form an ultra-smooth layer in accordance with certain embodiments.

In other embodiments, the size, shape and surface area of the underlying surface is altered by undergoing a shape-change or volume-change, as shown in FIG. 5B, such as thermal and/or optical responsive polymers that undergo a shape-change during the treating process, an electro-activated gel/or polymer that expands its volume by application of an electric field. For example, in some embodiments hydrogels undergo a shape/volume-change in response to external stimuli (e.g., mechanical forces, temperature, pH, optical response, humidity, M-field, E-field, electrical current, glucose, enzyme, antigen, ultrasound, and the like). Other materials include electro-activated gels/or polymers that expand their volume in response to electric field, ferrogels that change their volume in response to the magnetic field, or any other volume-changing material. FIG. 5B demonstrates the working principle of such surfaces: a substrate made of responsive material that has SLIPS properties in its swollen form, but produces a non-SLIP structure when contracted due to the receding of Liquid B into increased pore volume of the underlying solid.

Figure 5C:
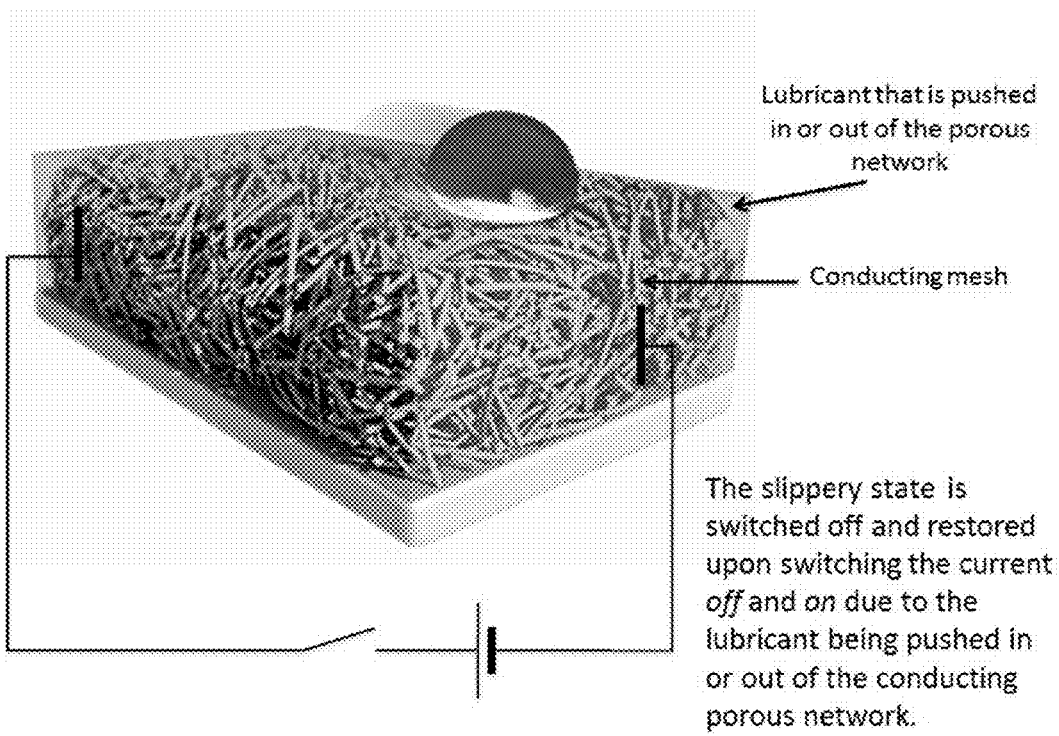
FIG. 5C shows a change from non-SLIPS to a SLIPS structure by applying an electrical current to the substrate to squeeze Liquid B to form an ultra-smooth layer in accordance with certain embodiments.

FIG. 5C shows one particular exemplary structure of FIG. 5B, where the substrate is a conducting mesh that expands or shrinks upon application of an electrical current that leads to a reversible switching between SLIPS and non-SLIPS structures. For example, the structure is be in a non-SLIPS state where the lubricant is trapped within the porous network between the conducting mesh and the conducting mesh surfaces are exposed to Object A. As an electrical current is applied, the conducting mesh expands, reducing the available free volume of the porous network, which in turn squeezes the lubricant out of the porous network to form a flat overlayer over the conducting mesh and form a SLIPS structure. When the electrical current is removed, the lubricant flows back into porous network between the conducting mesh to again form a non-SLIPS structure.

Figure 5D:
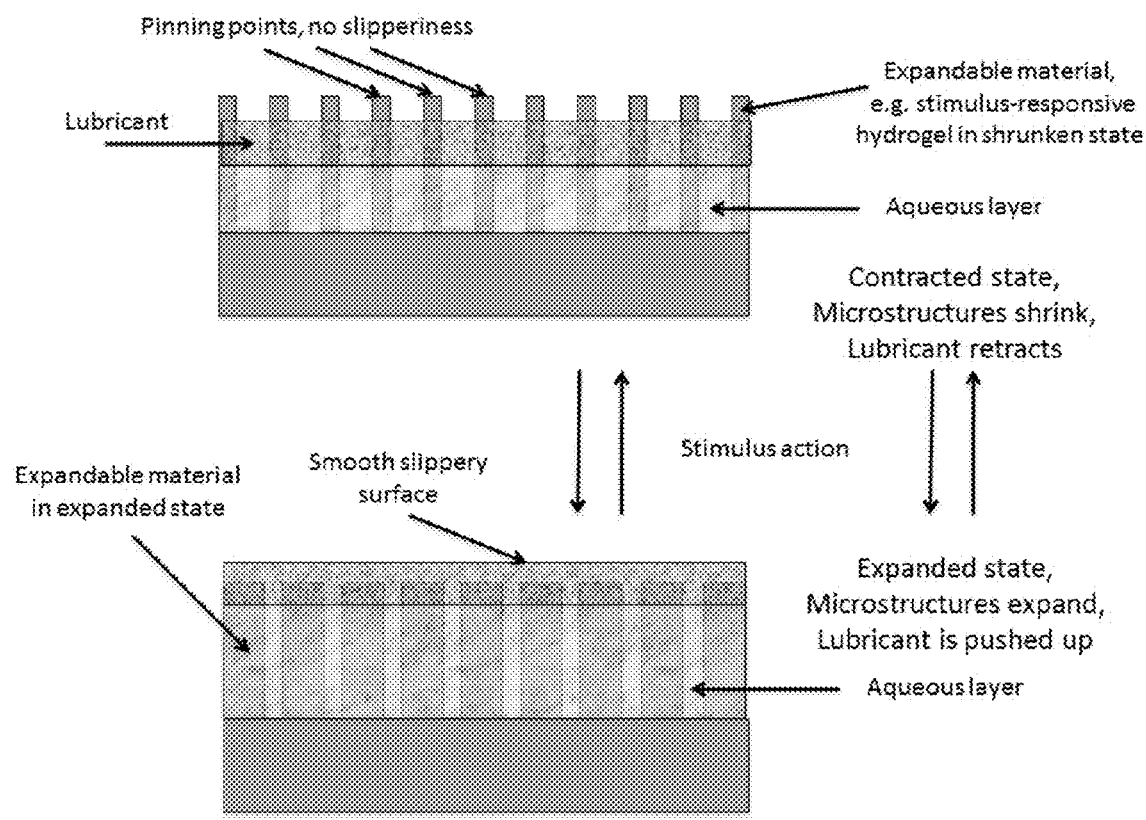
FIG. 5D shows a change from non-SLIPS to a SLIPS structure using an intermediate layer over the substrate to squeeze Liquid B to form an ultra-smooth layer in accordance with certain embodiments.

Another exemplary structure of FIG. 5B is shown in FIG. 5D. A substrate having a plurality of microstructures is shown, wherein the entire substrate or the microstructures are made of a material that changes its volume upon application of a suitable stimulus (e.g., stimulus-responsive hydrogel). As discussed above, in some embodiments suitable stimulus includes mechanical, temperature, pH, light, E-field, M-field, glucose, enzyme, antigen, ultrasound, and the like. However, in this particular example, the substrate can further include an intermediate layer (e.g., aqueous layer) between the lubricant and the underlying substrate, wherein when the substrate expands (e.g., upon swelling by hydration), the reduction in the free volume between the microstructures of the substrate leads to a rise in both the level of the intermediate layer and the lubricant to switch from a non-SLIPS structure to a SLIPS structure. Upon application of a suitable stimulus, the substrate shrinks again, leading to a lowered level of the lubricant and the intermediate layer and provide a non-SLIPS structure.

Figure 5E:
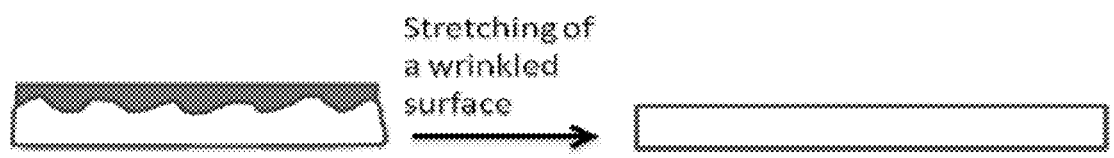
FIG. 5E shows a change from a SLIPS to a non-SLIPS structure by changing the roughness of the underlying solid surface in accordance with certain embodiments.

In certain embodiments, mechanical deformation is used to change the surface roughness, such as from a wrinkled, rippled surface to a flat, smooth surface, as shown in FIG. 5E. As seen in equations e2 and e3 above, the reduction of R leads to reduced energy gain, which correlates with the reduction or deterioration of the SLIPS function. In some embodiments, such a change is used to influence the wetting of the Liquid B layer on the surface and transform a SLIPS structure to a non-SLIPS structure. In some embodiments, since a high-surface area for the solid surface enhances the ability for the solid substrate to retain Liquid B in place (which increases with increasing surface roughness), such a change from a rough/wrinkled surface to a flat surface is used to influence the wetting and retention of the Liquid B layer on the surface, such that Liquid B leaves the surface upon its flattening.

Figure 5F:
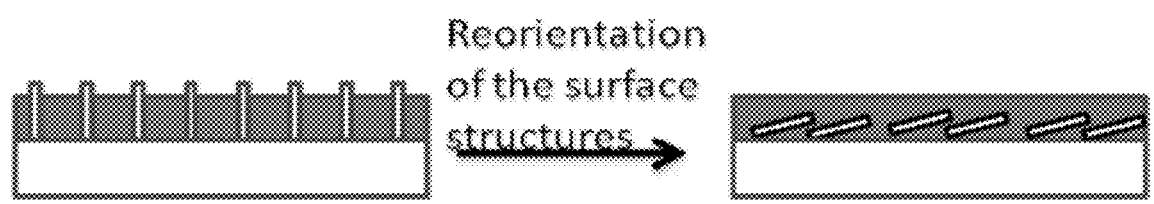
FIG. 5F shows a change from a non-SLIPS to a SLIPS structure by reorienting the surface structures of the underlying solid surface in accordance with certain embodiments.

FIG. 5F shows another example of using the solid surface with up-right high-aspect-ratio structures that reconfigure from an up-right to a bent or tilted configuration in response to a stimulus (e.g., mechanical, T, pH, light, E-field, M-field, glucose, enzyme, antigen, ultrasound, etc.). When such a surface is filled with a Liquid B that does not cover the high-aspect-ratio structures in their upright orientation, but covers the surface in their bent configuration, the material then reversibly switches its behavior from non-SLIPS to SLIPS.

Figure 5G:
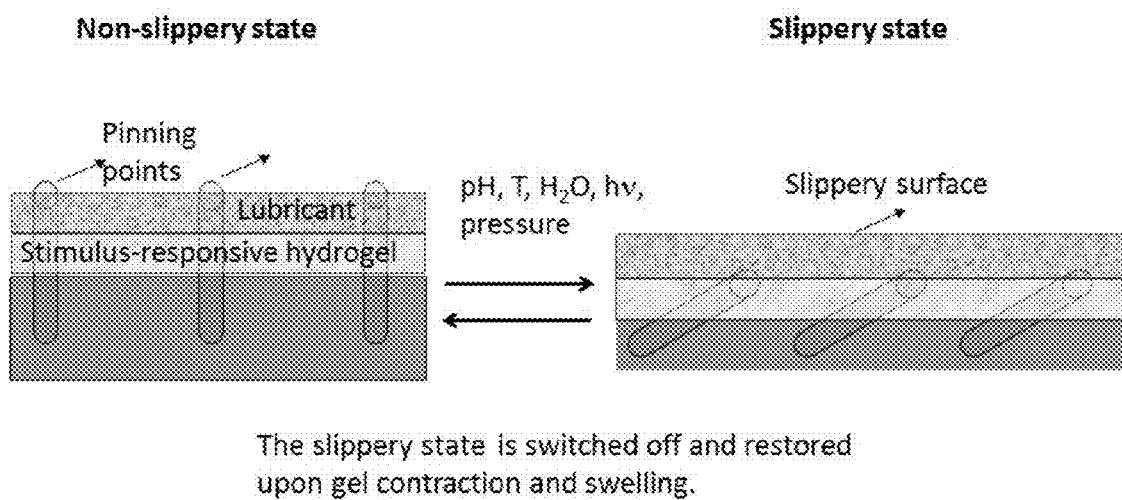
FIG. 5G shows a change from a non-SLIPS to a SLIPS structure by reorienting the surface structures within an intermediate layer, lubricant and/or the substrate in accordance with certain embodiments.

FIG. 5G shows yet another example, where freely-moving high-aspect-ratio structure resides within the substrate, lubricant and/or an intermediate layer (e.g., stimulus-responsive hydrogel), at least one of which is responsive to a certain stimulus. Upon application of a suitable stimulus (e.g., mechanical, T, pH, light, E-field, M-field, glucose, enzyme, antigen, ultrasound, etc.), the substrate, lubricant and/or the intermediate layer expands or contract leading to the reorientation of the high-aspect ratio structures and leading to reversible switching between non-SLIPS and SLIPS structures.

Figure 5H:
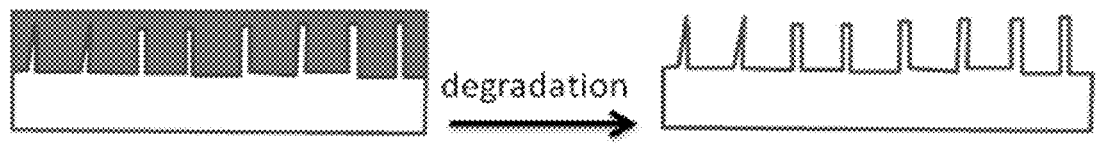
FIG. 5H shows a change from a SLIPS to a non-SLIPS structure due to degradation of Liquid B in accordance with certain embodiments.

In some other embodiments, a substrate that changes the way Liquid B is entrained over time is utilized. For example, as shown in FIG. 5H, the underlying substrate degrades, such that for example, the functionalized surface loses or substantially reduces its affinity to the lubricant and the lubricating Liquid B leaves the substrate over time. This exposes the underlying surface features. In further embodiments, a substrate is initially be impermeable to Liquid B but subject to degradation (e.g., bioerosion) during operation leading to increased diffusion of Liquid B into the substrate over time to form a non-SLIPS structure.

Figure 5I:
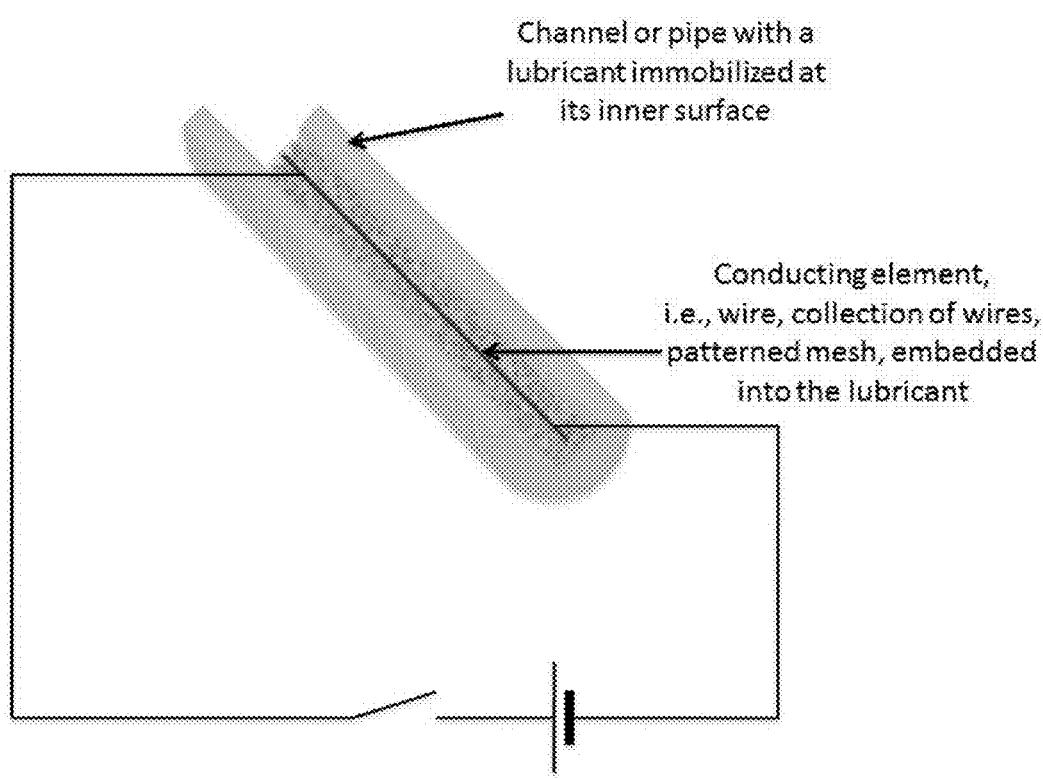
FIG. 5I shows a change from a SLIPS to a non-SLIPS structure inside a pipe or channel by applying an electrical current in accordance with certain embodiments.

Although the embodiments have been illustrated using an open structure, in some embodiments the system is employed in different configurations. For example, FIG. 5I shows a channel or pipe with a lubricant immobilized at the inner surface, wherein application of a suitable stimulus reversibly changes the internal surfaces of the channel or pipe from a non-SLIPS to a SLIPS structure.

Some suitable underlying solid structure (or intermediate layers) utilized in accordance with the present disclosure that responds to stimulus include conductive materials (e.g., non woven metal/metal alloy mesh, carbon nanotubes, polypyrroles, polythiophenes, polyaniline, and the like), elastic materials (e.g., polyurethane, rubbers such as s: isoprene rubber, butadiene rubber, chloroprene rubber, neoprene, butyl rubber, styrene-butadiene rubber, nitrile rubber, silicone rubbers such as polydimethylsiloxane, fluorosilicone rubber, fluoroelastomers such as Viton, Tecnoflon, Fluorel, or Aflas, perfluoroelastomers such as Tecnoflon PFR, Kalrez, Chemraz or Perlast, Polyether block amides, and the like), any responsive gel materials that undergo phase/volume change (e.g., hydrogels, organogels, physical gels), piezoelectric materials (e.g., piezoelectric ceramic, zinc nanoarray, barium titanate, lead titanate, lead zirconate titanate (known as PZT), potassium niobate, lithium niobate, lithium tantalite, sodium niobate, bismuth titanate, and the like or organic, polymeric piezoelectrics such as polyvinylidene fluoride (PVDF)); sponge-like materials that deform or collapse in response to a mechanical or other stimulus (metallic meshes and foams, foamed polymers, such as foamed polyurethane, fibrous Teflon materials, and the like). Exemplary responsive gels are described in Mano, J. F. *Adv. Eng. Materials* 2008, 10(6), 515-527; de las Heras Alarcón, C. et al. *Chem. Soc. Rev.* 2005, 34, 276-285; Gupta, P. et al. *Drug Discovery Today* 2002, 7(10), 569-579. In some embodiments, materials that decompose or melt are also used as dynamic substrate materials.)

As will be apparent to one of ordinary skill in the art in light of the discussion provided herein, in some embodiments the switch between SLIPS and non-SLIPS structures occurs locally. To achieve this the response, in some embodiments a solid is further patterned with various regions having different dynamic characteristics, such that the SLIPS function is switched ON and OFF only locally, or different regions have different "slippery" characteristics. In some embodiments, such patterning is achieved by imparting different mechanical characteristics onto/within the roughened elastic structure, in discrete or continuous patterns, by varying, e.g., cross-linking density, porosity, geometrical parameters, such as thickness of the elastic layer and the like. The foregoing patterning methods are provided as exemplary only, and any of the well-known methods for formulating and patterning surfaces are well-known in the art and are used in accordance with any of the embodiments disclosed herein.

Modification of Liquid B

Figure 6A:
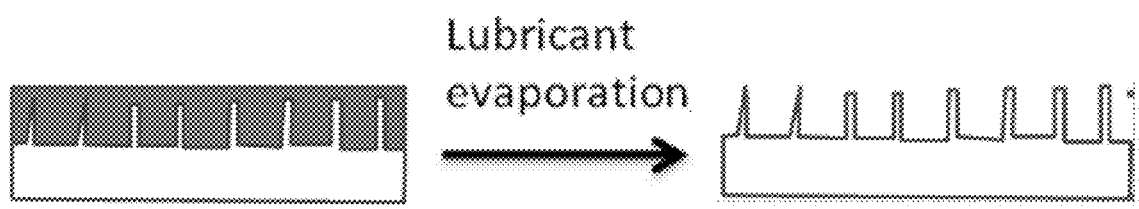
FIG. 6A shows a change from SLIPS to a non-SLIPS structure by evaporation of Liquid B in accordance with certain embodiments.
Figure 6B:
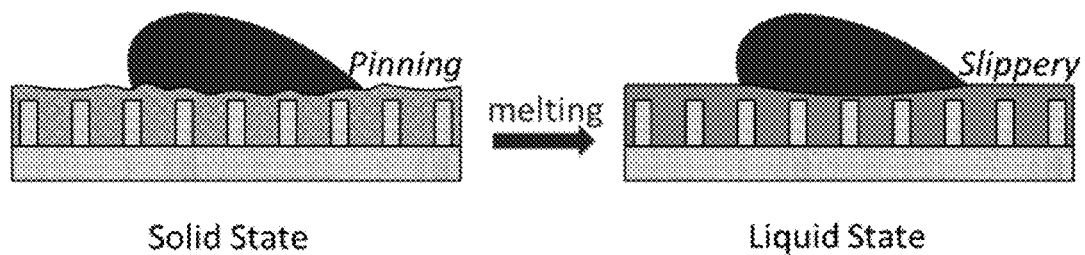
FIG. 6B shows a change from non-SLIPS to a SLIPS structure by melting and freezing Liquid B using temperature in accordance with certain embodiments.

In certain embodiments, the volume of lubricating liquid is altered to expose the underlying surface of structures without the change of the underlying solid. For example, as shown in FIG. 6F, a fluidic chip containing a pumping mechanism is employed to control the flow of Liquid B onto the SLIPS surface. The presence or absence of the ultrasmooth surface formed by Liquid B is controlled actively by pumping the Liquid B in or out of the surface. In some embodiments, dynamic SLIPS is used to finely control the SLIPS character of the surface by controlling thickness of the lubricating layer using a pumping system. The surface is slippery when more lubricant is pumped in, and turns to less slippery when the lubricant is pumped out.

In other embodiments, Liquid B is chosen to be volatile so that it evaporates and expose the underlying roughened structure over time, leading to a loss of the SLIPS structure and degradation of the performance. For example, FIG. 6A shows a SLIPS structure where the lubricant evaporates over time to lead to a non-SLIPS structure. To return to the SLIPS structure, Liquid B is replenished as needed.

In certain embodiments, Liquid B is selected to change or degrade over time, so that the chemical composition of the lubricating liquid changes over time and the SLIPS properties change or degrade correspondingly. In some embodiments, the change in chemical composition of Liquid B leads to greater adhesion of Liquid B to Object A, faster diffusion of Liquid B into the underlying solid surface, faster evaporation of Liquid B away from the solid surface, and the like.

In certain embodiments, Liquid B that changes its properties as a function of an external stimuli (e.g., temperature, pH, electric field, magnetic field, acoustic, and the like) are utilized. In some embodiments, Liquid B includes a material that changes its phase from solid to a liquid through application of temperature. As shown in the left side of FIG. 6B, solidified lubricant forms a non-SLIPS structure as the solidification of the lubricant (Liquid B) leads to greater adhesion to the droplets and/or lead to roughening of the surface. However, upon melting of the lubricant (Liquid B) by increasing the temperature to a sufficiently high enough temperature (e.g., the melting point, temperatures above the glass transition temperature, etc.), the SLIPS structure forms again. Some exemplary Liquid B that are reversibly changed from a solid to a liquid under normal operating conditions in accordance with the present disclosure includes paraffins, waxes, including biological, and their fluorinated counterparts, such as docosafluoro-n-decane, (1S,2R,5S)-2-(2,2,3,3,4,4,5,5,6,6,7,7,8,8,9,9,10,10,11,11,11-henicosafluoroundecyl)-6,6-dimethylbicyclo[3.1.1]heptane, perfluorodecane-limonene, perfluorodecane-octane and the like.

In certain embodiments, the change of Liquid B is not as drastic as a phase change, but a change in the viscosity of Liquid B to provide the control of the extent of the slippery function, i.e. viscosity tunability of the lubricant. For example, as shown in FIG. 6D, using a viscous liquid as Liquid B provides largely non-SLIPS behavior due to the high viscosity of the liquid, where a highly viscous liquid does not lead to a more adherent surface. After increasing the temperature to a critical point, the viscosity of Liquid B decreases to a sufficiently non-viscous state leading to a structure having greater SLIPS characteristics. This approach provides a way to actively control the velocity of the droplet transport on these surfaces as a function of the viscosity of the underlying lubricant. In some embodiments, the system starts from a lubricant liquid of a relatively high viscosity, for example DuPont Krytox 105/107.

As another example, in some embodiments Liquid B repels Liquid A when in a SLIPS structure, but attracts Liquid A as Liquid B turns into Gas B and boils away as the temperature is raised.

In some other embodiments, additives that change function of Liquid B are added, such as additives that respond to external stimuli (e.g., temperature, pH, electric field, magnetic field, acoustic, and the like). For example, in some embodiments, by adding monomers that undergo polymerization in response to a certain stimulus/environmental conditions, the gelation/solidification of Liquid B is controlled, where solidification of Liquid B leads to a reduction in their slippery characteristics. In certain embodiments, the gelation mechanism is reversible, and the polymer network dissociates again upon the removal of the stimulus, allowing a reversible transition back to the SLIPS structure when the gel-formed layer turns back into a liquid again. In some embodiments, nanotubes and/or graphene is added to impart electrical properties to Liquid B, which is utilized to allow Liquid B to respond to electric field.

In other embodiments, the ultra-smooth surface of Liquid B is disrupted, so that it no longer provides a ultra-smooth surface. For example, as shown in FIG. 6E, Liquid B includes magnetic particles (e.g., ferrofluids) that respond to a magnetic field by forming a rippled surface. Although FIG. 6E demonstrates use of a magnetic field to impart the rippled surface 330 shown in FIG. 3, many different techniques for forming non-ultra-smooth surfaces can be envisioned, such as mechanical vibrations, acoustic vibrations, and the like that cause ripples to form on Liquid B.

In certain embodiments, the system is employed in different configuration. For example, FIG. 6G shows a channel or pipe with a lubricant immobilized at the inner surface, wherein application of a suitable stimulus reversibly changes the state of Liquid B (lubricant) present in the internal surfaces of the channel or pipe from a solid to a liquid. Accordingly, in some embodiments the internal surfaces of the channel or pipe reversibly switch between non-SLIPS to SLIPS structures.

In certain embodiments, surface features 110 contain inherent or imparted characteristics that promote adhesion of particular types of Object A. In this case, the accumulation of this material collected from Object A on the surface changes its slippery function. Such design can then play a role of a sensor for the presence of certain components/contaminants in Object A.

In some embodiments, in addition to the single controls of porous solid and fluid, dynamic properties of both solids and fluids are combined to achieve dual or even multiple switches. For example, in some embodiments the stretchable porous membrane is selected as the substrate, and Liquid B comprises magnetic-responsive fluids and/or thermal-responsive fluids. Switchable properties are thus achieved on a two-dimensional area by stretching the substrate on which the Liquid B redistributes, as described above. In some embodiments, a further adjustment is made by locally applying an external stimulus on Liquid B such as a magnetic field on ferrofluids or thermal heating/cooling on a temperature sensitive liquid.

Any combination of the stimuli that changes the structure of the SLIPS and therefore its function/performance characteristics can be used in accordance with the present disclosure. In some embodiments, the SLIPS function is tuned through the modifications of either the solid or the lubricant separately, as described above, or, in further embodiments, they are both adaptive and contribute to the change of the SLIPS behavior. Therefore, in some embodiments, any combination of a dynamic substrate with a dynamic Liquid B is possible, such that both the solid surface and the Liquid B undergo changes to obtain non-SLIPS structures.

Figure 6C:
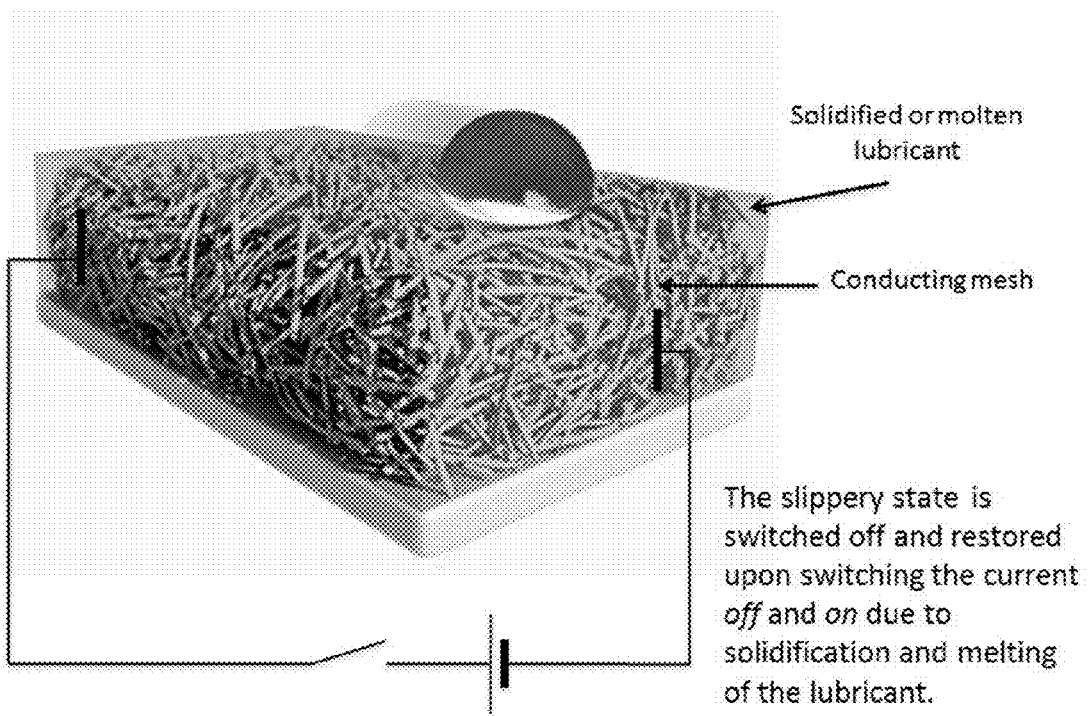
FIG. 6C shows a change from SLIPS to a non-SLIPS structure by melting and freezing Liquid B using electrical current in accordance with certain embodiments.
Figure 6D:
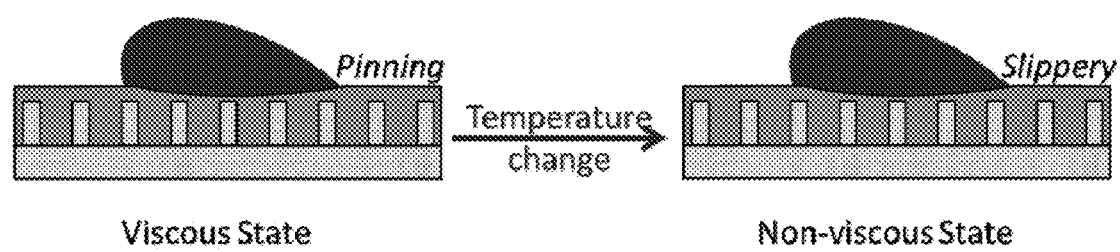
FIG. 6D shows a sketch for a design of a thermal-responsive dynamic SLIPS structure which shows a change from a less slippery state to a more slippery state by changing the viscosity of Liquid B from higher to lower in accordance with certain embodiments.
Figure 6E:
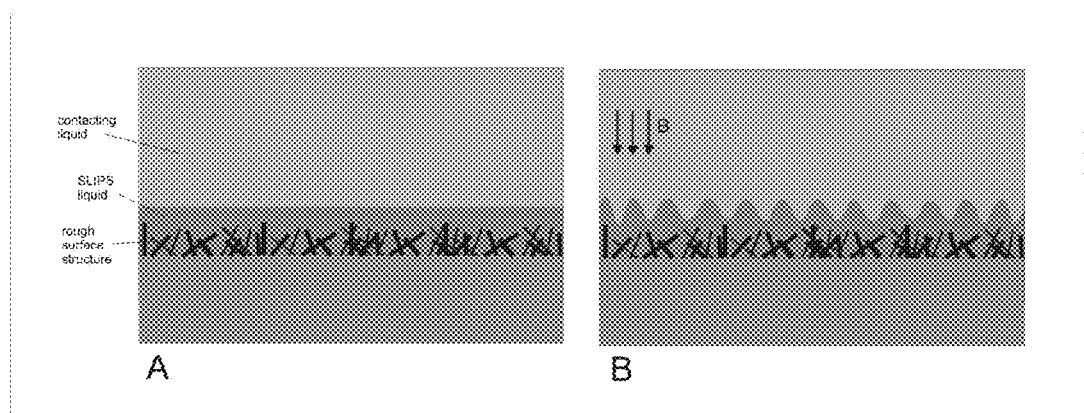
FIG. 6E shows a change from SLIPS to a non-SLIPS structure as a function of applied magnetic field in accordance with certain embodiments.
Figure 6F:
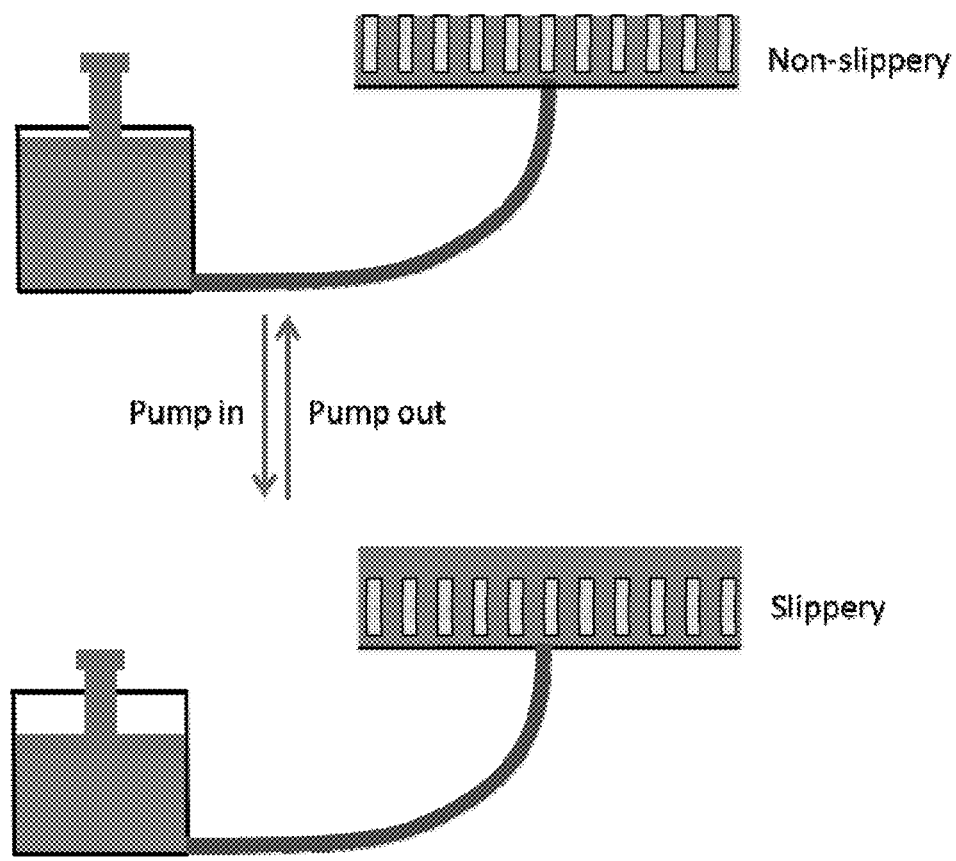
FIG. 6F shows a change from a structure having more SLIPS character to a surface having less SLIPS character by pumping in and out Liquid B in accordance with certain embodiments.
Figure 6G:
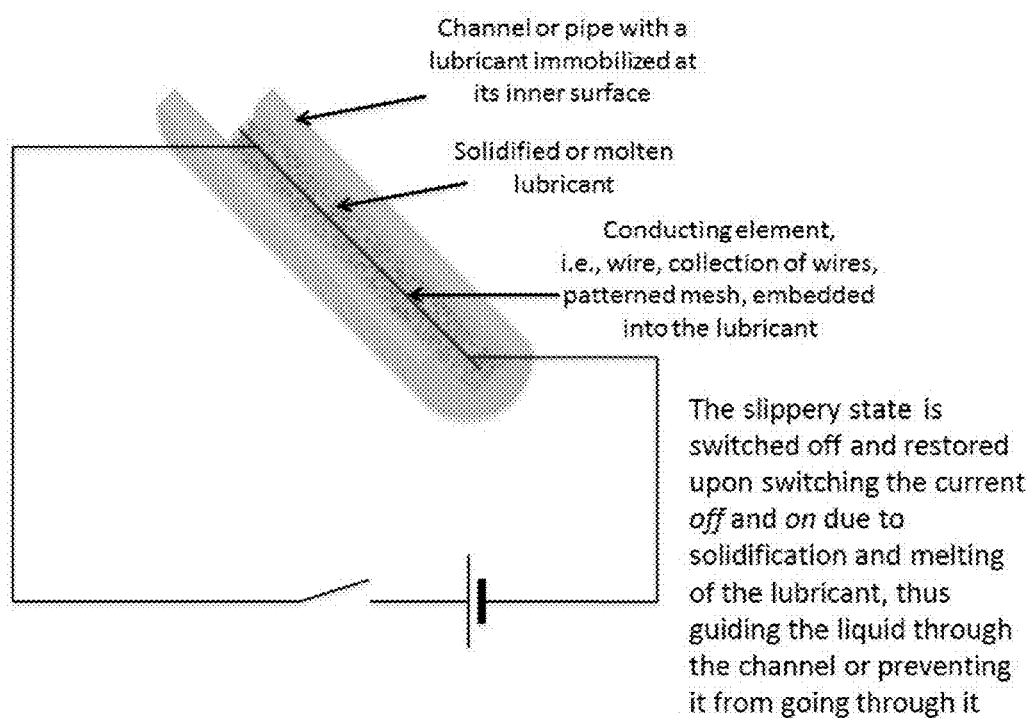
FIG. 6G shows a change from a SLIPS to a non-SLIPS structure inside a pipe or channel by applying an electrical current to melt and freeze Liquid B in accordance with certain embodiments.

An exemplary embodiment of such a structure is shown in FIG. 6C or FIG. 6G. As shown, the underlying substrate is formed of a conducting mesh that is heated upon application of an electrical current. The lubricant is chosen to be solid at ambient temperature, but melt upon local heating induced by the current applied to an underlying conducting mesh. Upon heating, the Liquid B (lubricant) melts, whereas removing the electrical current solidifies the lubricant. Solidification of the lubricant leads to a non-SLIPS surface while melting of the lubricant reversibly reverts to the SLIPS structure.

Other Desired Properties of Dynamic SLIPS

In addition to the transition between the SLIPS and non-SLIPS structure described above, in some embodiments other desired properties are imparted, such as reversibility, directionality, local switching behavior, continuous tuning of properties between extreme states, such as optical transparency, adhesion characteristics, mobility of the Objects A, and the like.

Reversibility

As will be apparent to one of ordinary skill in the art in light of the discussion provided herein, in some embodiments, the switch between SLIPS and non-SLIPS structures is either reversible or irreversible. In some embodiments, use of Liquid B having magnetic particles provides a reversible switch between SLIPS and non-SLIPS structures by application and removal of a magnetic field. In some embodiments, use of different solidification temperatures between Object A and Liquid/Solid B also provides a reversible switch between SLIPS and non-SLIPS structures by increase and decrease of temperature. In some embodiments, use of an elastic substrate to deform the solid layer and recede Liquid B provides a reversible switch between SLIPS and non-SLIPS structures by application and removal of a mechanical strain.

In some embodiments, evaporation or degradation of Liquid B over time leads to an irreversible switch from SLIPS to a non-SLIPS structure. In some embodiments, evaporation or boiling away of Liquid B by increasing the temperature leads to an irreversible switch from SLIPS to a non-SLIPS structure.

Both types of switch may be important depending on different types of application provided.

Continuous Tuning of Properties

To meet widespread challenges in efficiency and sustainability, future materials must be designed to dynamically adapt to environmental changes. A growing assortment of strategies has enabled the development of stimuli-responsive materials, but most are limited to two-state ON/OFF switching of single properties, and only a small number of strategies that lead to materials with continuously adjustable characteristics were reported. Even more elusive are multi-functional materials capable of changing several performance parameters in a highly controlled fashion. In some embodiments, dynamic SLIPS provides a solution to this challenge and offer multifunctional, adaptive materials that enable a single surface to reversibly span an entire range of functional properties from one extreme to another, with stimulus-sensitive fine-tuning along the way.

In one embodiment shown in FIGS. 14-20, such a property is achieved by using a liquid film supported by a nanoporous elastic substrate. The liquid flows over and within the pores as the substrate deforms, and thus causes the free surface to change from a defect-free smooth one to a rough one through a continuous range of topographies. The interplay between elastic and fluid components enables a graded mechanical stimulus to be directly translated into finely tuned, dynamic adjustments of two functions: (i) material's transparency that is continuously manipulated from transparent to opaque, and (ii) the ability to transport and discriminate various Liquids A that are continuously manipulated from free-sliding to pinned, with the precise control of their movement velocity as a function of the applied strain. By pairing the fluidity of an infiltrated liquid film with the elastically responsive topography of a porous solid, many materials are imbued with properties that are sensitive to fine features of the surface topography associated with optics, wettability, adhesivity, anti-fouling and surface transport characteristics into the realm of responsive materials.

In addition to the two-state switch, the functionalities of the surface are continuously controlled in some embodiments by gradually adjusting the external stimuli. For example, in some embodiments the optical transparency of the SLIPS membrane is continuously tuned by gradually stretching the membrane as in FIG. 18B and FIG. 18C. In further embodiments, the sliding angles of the different low-surface-tension hydrocarbons are continuously controlled, as illustrated in FIG. 19F and FIG. 19G. In still further embodiments, as the morphology tunability of ferrofluid is related to the strength of the external magnetic field, the surface properties of the magnetic-SLIPS is also continuously tuned.

Optical Transparency

In certain embodiments, the transition between SLIPS and non-SLIPS structures is accompanied by transition from an optically transparent state to an optically opaque (or less transparent) state. For example, in some embodiments the SLIPS structure provides an optically transparent material whereas the non-SLIPS structure (e.g., after evaporation, receding or other removal of Liquid B) provides an optically opaque material.

Mobility Control

The continuous tunability of the liquid film morphology provides a way to control surface wettability and adhesiveness. Manipulating fluids, particularly those with low surface tensions, has proved extremely difficult on rigid surfaces: controlling mobility notoriously requires restructuring of intricate and fragile topographical elements that are hard to change. Soft surfaces show more promise, but they still fail with low-surface-tension liquids, and even higher-surface-tension droplets cannot easily be remobilized once they pin on and wet the surface. In some embodiments of the dynamic SLIPS system disclosed herein, the flat, atomically smooth liquid interface in the SLIPS state serves as a lubricating layer and allows liquids to slide freely, while the rougher film topography in the non-SLIPS state leads to pinning that inhibits motion (see FIG. 16). This surface thus provides a simple, stimulus-responsive way to tune liquid mobility and transport in real time.

In some embodiments, by controlling the amount of the infused lubricant or the applied strain of the membrane, the mobility of the impinging liquids on the stretchable-SLIPS is gradually tuned. In further embodiments, the liquid is controlled from moving to pinning by application of strain on the surface. In further embodiments, the velocity of sliding droplets on the surface are controlled by gradually controlling the strain or the amount of the infused lubricant. In still further embodiments, specific liquids are selected to be pinned to the surface by matching the relationship of the surface tension and sliding angle which is tuned by applying strain to a certain point.

Local Switching Between SLIPS and Non-SLIPS

In some embodiments, switching of the SLIPS function is done over the entire structure, or locally. In some embodiments where the underlying solid is patterned with regions having various responsive characteristics, the SLIPS function is switched OFF or restored within a certain region. In these embodiments, this is used to switch ON and OFF the directional transport of liquids, to induce local switchable adhesive characteristics, to induce patterned transparency changes, etc. In one embodiment depicted in FIG. 6C and FIG. 6G, if the conducting material is placed in stripes and a melting Liquid B is chosen, the application of the current produces a melted, directional "slippery" path. The slippery function is directional, and the droplets travel along the melted path.

APPLICATIONS

Numerous different applications for modification of SLIPS to non-SLIPS can be envisioned where surface that repel a wide range of materials followed by a surface that attract certain materials is desired, or surfaces that change their properties due to the redistribution of the lubricant in the structure. Some non-limiting exemplary applications are described below.

Control of Surface Adhesiveness and Liquid Mobility and Transport on Surfaces

One of the most interesting properties of dynamic SLIPS surfaces is their ability to tune or to switch ON/OFF the adhesion of various Objects A to the surface. In particular, the non-limiting examples below show the potential of this property in manipulating liquids on the surfaces and controlling the surface adhesive characteristics. In some embodiments, dynamic SLIPS is designed to switch between adhesive and non-adhesive state, to switch ON and OFF liquid movement, to continuously or abruptly change the velocity of liquid transport, to induce liquid separation and identification, to control the direction of liquids movement, etc.

Biodegradable SLIPS Layers for Medical Implants

Medical implants such as orthopedic grafts, dental implants, hip implants, and fracture repair plates and screws, require bone tissue to biologically and mechanically bond to the implant surface following implantation. In some embodiments, this bonding process takes place over an extended period of time, from days to months (and years). Keeping such medical implants free from bacterial contamination is also critically important, to minimize the risk associated with blood-based sepsis and bacterial biofilm formation. However, continued use of the SLIPS structure to reduce bacterial contamination would also prevent the bonding of human tissue in the longer term, following implantation surgery. Therefore, the adhesion resistance of a conventional SLIPS surface would be counterproductive in the long-term.

Accordingly, in some embodiments, Liquid B that degrades, deteriorates and/or is displaced with time is utilized. As a result, the SLIPS layer gives the implant surface antibacterial properties during implantation in the short term, but allows tissue bonding after implantation, when the SLIPS liquid degrades. Therefore, in some embodiments long term bonding of tissue to the implant surface takes place over a long term time scale.

In some embodiments, Liquid B is removed through biodegradation, oxidation, emulsification, depolymerization, dissolution or the like. Biocompatible Liquids B include various kinds of hydrocarbon oils, silicone oils such as polydimethylsiloxane (PDMS), polyethylene glycol (PEG), glycerin or dextran. In some embodiments, certain fluorinated lubricants commonly used in medical applications such as perfluorodecalin, Perflubron, and the like, are also applied.

Figure 7A:
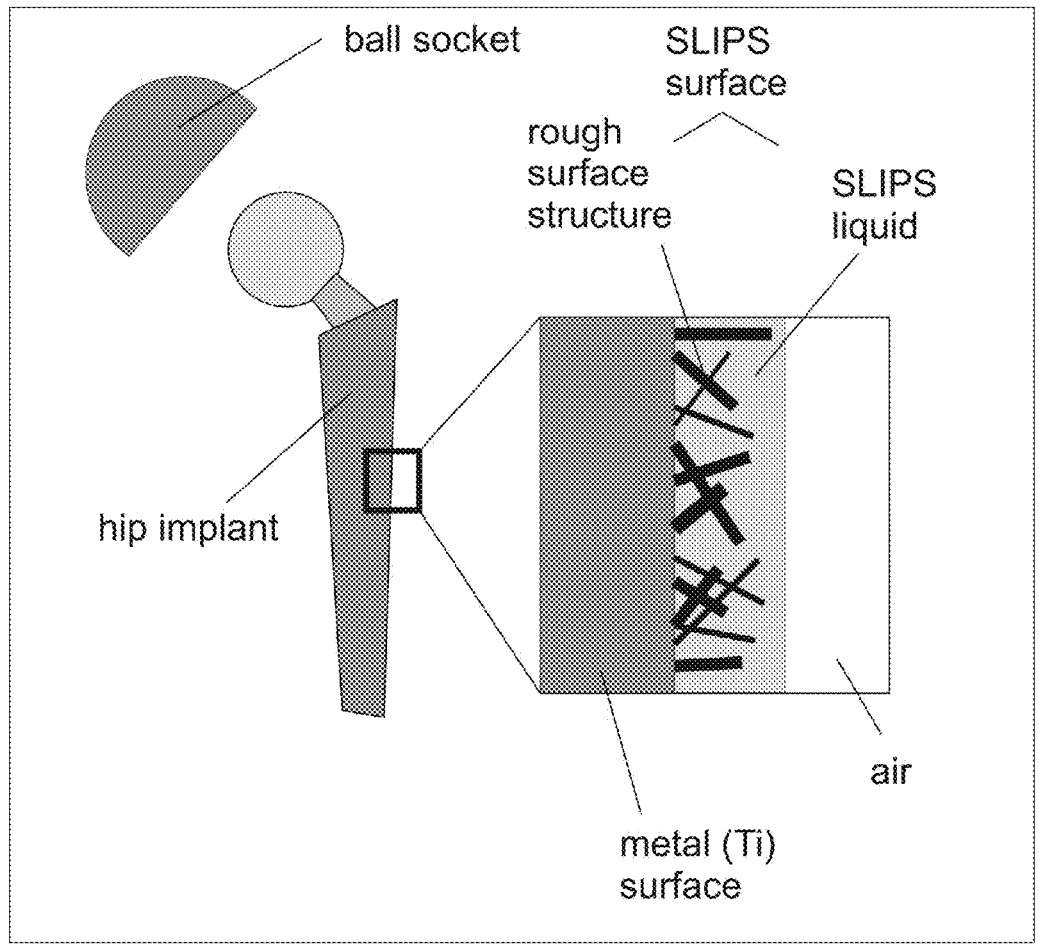
FIG. 7A shows a hip implant having a SLIPS structure formed thereon in accordance with certain embodiments.

In certain embodiments, Liquid B gradually degrades over a period of time ranging from hours to days, (or possibly weeks), depending on the nature of the implant, and the rate of tissue growth, inflammation, etc. FIG. 7A shows schematically a bone implant having the SLIPS structure chemically functionalized with, for example, fully, partially fluorinated or non-fluorinated long-chain alkyl silanes. As shown, the implant contains a metal (e.g., Ti) surface having rough surface structures. Liquid B forms an ultra-smooth surface over the rough surface structures.

Figure 7B:
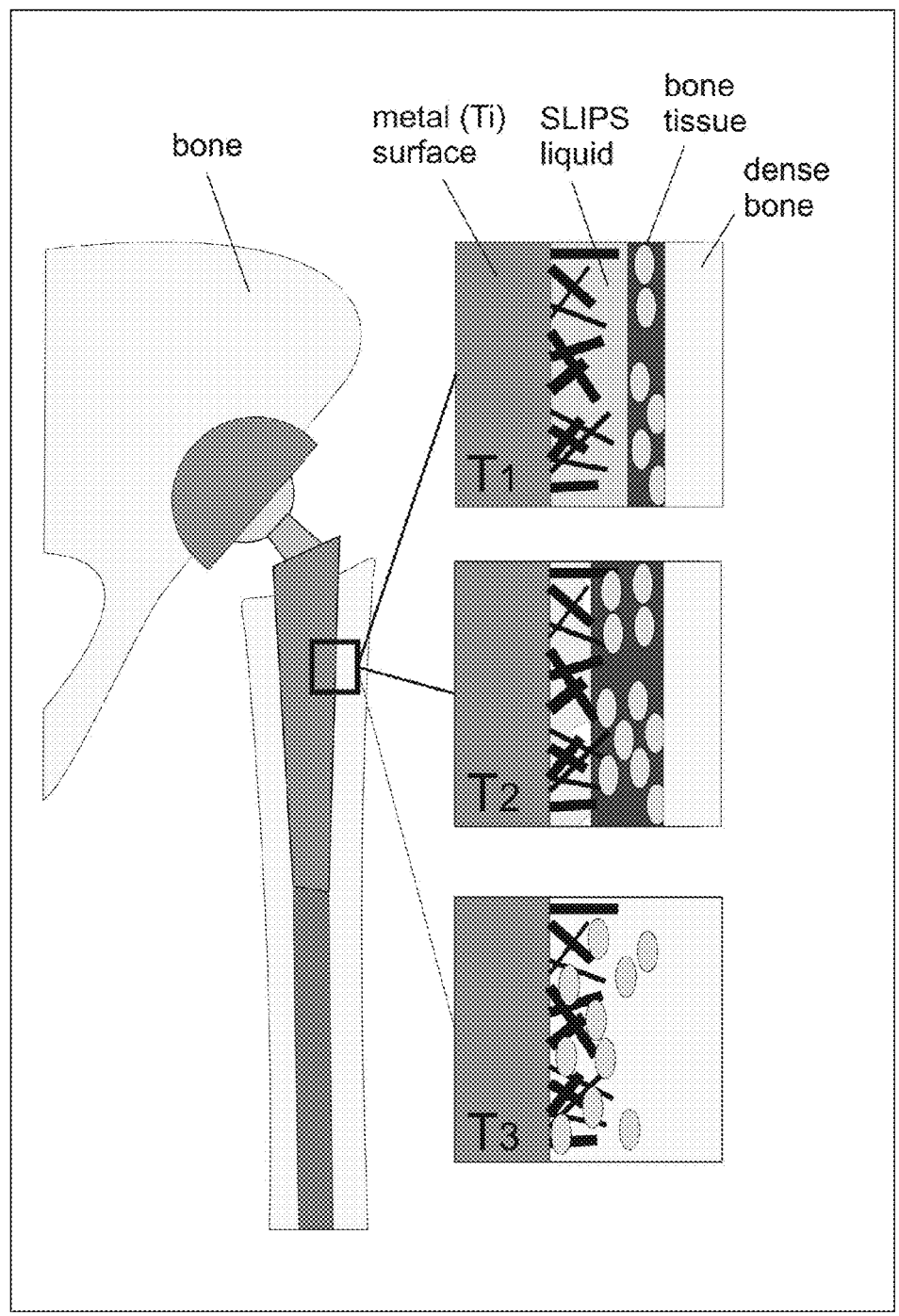
FIG. 7B shows a hip implant having a SLIPS structure that forms a non-SLIPS structure over time in accordance with certain embodiments.

FIG. 7B shows schematically the evolution of the SLIPS structure as a function of time after implantation. As shown, initially at time $T_1$, SLIPS structure is formed so that undesired bacterial biofilm formation or blood-based sepsis is avoided. However, in certain embodiments, after certain time (e.g., $T_2$ and $T_3$), Liquid B biodegrades over time to expose the roughened surface which promotes adhesion of bone tissue to promote strong adhesion between dense bone and the implant.

In some embodiments, a further modification involves the incorporation of an antibacterial agent, or growth factor, into the Liquid B itself, which is also be released at the same time as Liquid B becomes removed from the surface. In some embodiments, Liquid B comprises D-Amino acids which effectively prevent the development of biofilm such as *B. subtilis* and *S. aureus* by blocked the subsequent growth of the foci into larger assemblies of cells. In further embodiments, antibiotics, drug-loaded nanoparticles, other drug-release vehicles, silver nanoparticles, BMP and the like are incorporated into Liquid B.

Additives that Changes Function of Liquid B

In certain embodiments, Liquid B is a magnetically-responsive liquid, such as a ferrofluid, a suspension of ferromagnetic particles in a liquid (e.g., a non-polar liquid). In such scenarios, Liquid B's morphology is controlled with a magnetic field. Ferrofluids can produce a wide range of morphological shapes in the presence of a magnetic field. Therefore, in some embodiments, a SLIPS surface develops morphologies in response to a field, which include ripples and waves on the surface, at length scales ranging from micrometers to millimeters.

In some embodiments, an oscillating wave moving across a SLIPS interface is useful for cleaning surfaces, such as dislodging bacteria or debris particles, in the same way that cilia work in biological systems. FIG. 6E shows a schematic representation of a ferrofluid-SLIPS structure in which the application of an external magnetic field causes a change in the surface morphology of the liquid. In certain embodiments, the field causes an oscillating motion, and instead of promoting adhesion, it is further utilized to remove debris or particles, such as bacteria or protein structures (e.g., fibrin, blood thrombus, and the like) from the surface.

In some embodiments, the external magnetic field is applied in such a way that it is external to the human body, while the ferrofluid-SLIPS is on a medical device internal to the body, such as a catheter tube. Therefore, in some embodiments a catheter is under temporary or continuous magnetic stimulation to keep the inner surfaces clear of debris, or to aid in the movement of the interior fluid, in a similar way to the cilia of natural structures, such as the lungs, trachea or abdomen.

Valveless Fluidic Channels

Figure 8:
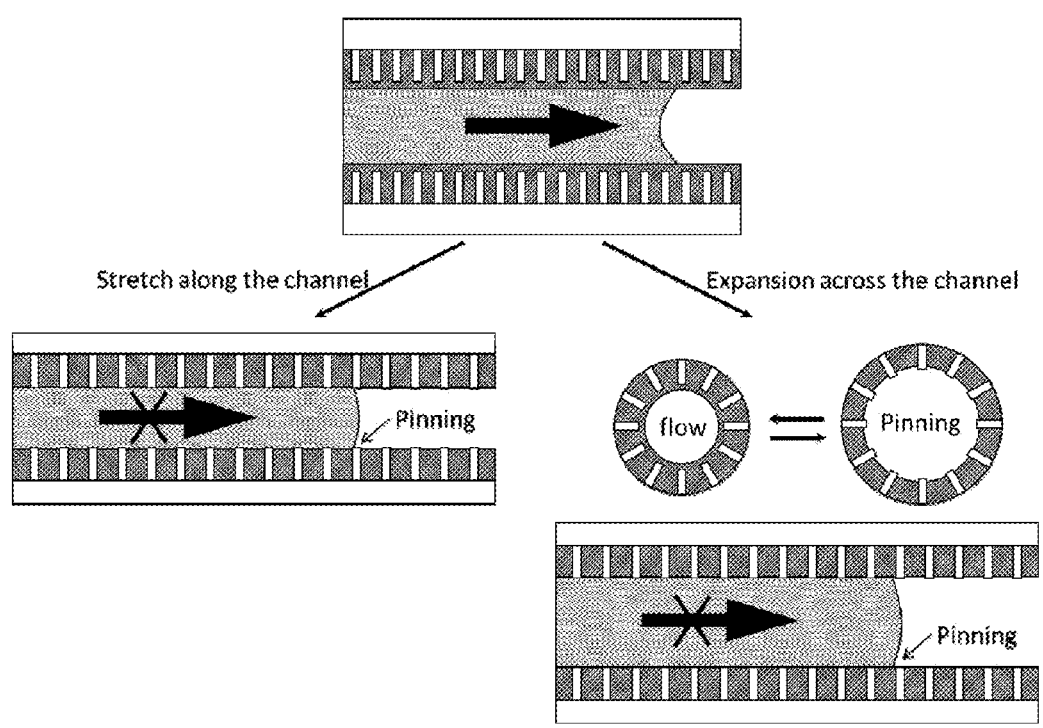
FIG. 8 shows a valveless microfluidic system that turns on and off the flow in accordance with certain embodiments.

In some embodiments, dynamic transition between SLIPS to a non-SLIPS structure is further utilized to provide a valveless fluidic system that "turns on" and "turns off" the flow of fluid within the fluidic channels. As shown in FIG. 8, a microfluidic channel having a SLIPS structure is provided. Due to the high slippery nature of SLIPS, in some embodiments fluids within the microfluidic channel readily flow. Upon application of some external stimuli (e.g., stretching), the SLIPS structure is transformed into a non-SLIPS structure. Accordingly, in some embodiments the fluid is pinned to the non-SLIPS structures to "turn off" the flow. In some embodiments, relaxing the strain then again "turns on" the flow as the SLIPS structure is recovered.

Liquid Separation

Figure 9:
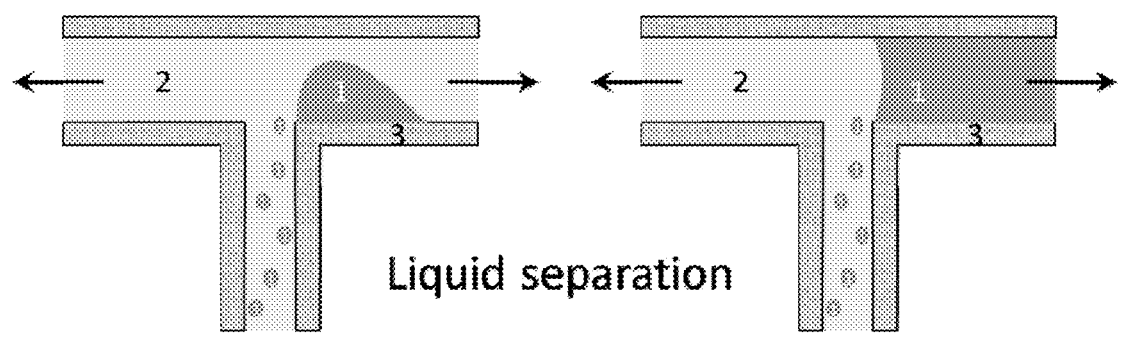
FIG. 9 shows a liquid separation technique utilizing dynamic transition between SLIPS and non-SLIPS structures in accordance with certain embodiments.

In certain embodiments, different response of fluids (Liquid A) to the SLIPS and non-SLIPS structures are utilized to achieve dynamic separation. For example, as shown in FIG. 9, a T-shaped fluidic system having a SLIPS structure on the walls of the fluidic channels is provided (see 3). Within the channels, two different liquids, such as Liquid A1 (see 1) and Liquid A2 (see 2) that are immiscible, are provided where both Liquid A1 and A2 readily flow as it contacts the SLIPS structure. Upon application of some external stimuli (e.g., stretching), the SLIPS structure transforms into a non-SLIPS structure. In some embodiments, Liquid A1 possesses properties (relative to the SLIPS/non-SLIPS structure) that lead to pinning of Liquid A1 to the non-SLIPS structure. However, in some embodiments, Liquid A2 has properties (relative to the SLIPS/non-SLIPS structure) that allow Liquid A2 to continue flowing through the fluidic channels. Accordingly, in some embodiments, Liquid A1 and Liquid A2 are separated. After Liquid A2 completely flows out of the microfluidic channels, the structure is reverted back to a SLIPS structure and subsequently and separately collect Liquid A1 that was previously pinned to the non-SLIPS structures. In some embodiments, toluene is Liquid A and water is Liquid B. By applying an external stimulus (such as stretch) to a critical point, the channel surface turns to non-slippery for toluene, but it is still slippery for water because water has much higher surface energy, and is more difficult to be pinned unless a much larger stimulus is applied. Hence, the toluene part in the fluid is pinned in the channel surface and the water part flows away.

Moisture Collector

Figure 10:
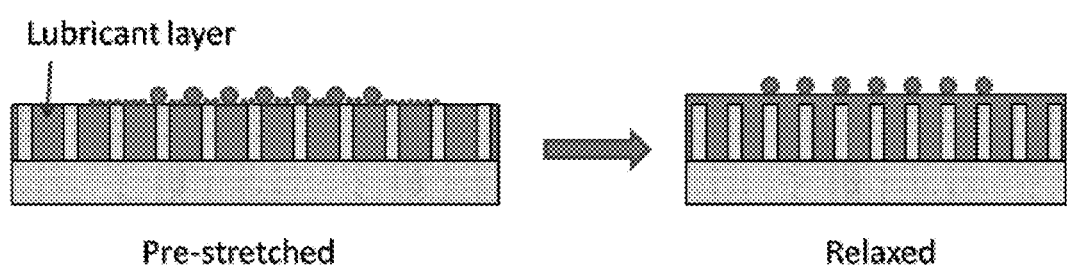
FIG. 10 shows moisture collector utilizing dynamic transition between SLIPS and non-SLIPS structures in accordance with certain embodiments.

In certain embodiments, the dynamic SLIPS structure is utilized to collect moisture from the environment. For example, as shown in FIG. 10, in a pre-stretched state, a non-SLIPS structure is formed. In some embodiments, such non-SLIPS structures are be highly adherent to moisture, leading to enhanced condensation of moisture from the environment onto the "rough" surfaces. As shown, a multitude of different sized droplets condense on the "rough" non-SLIPS surface. In some embodiments, after a suitable amount of condensation has occurred, upon application of a suitable stimulus (e.g., stretch, pressure, M-field, E-field, etc.), the non-SLIPS structure is converted into a SLIPS structure, whereupon the condensed water droplets freely slide on the SLIPS surface (and potentially some smaller droplets coalesce into larger droplets). By providing a suitable energy (e.g., tilting of the structure, blowing of the droplets, and the like), the condensed moisture is collected in a reservoir leading to a moisture free surface. Then, upon removing the stimulus, a non-SLIPS structure is formed again, whereupon further condensation of moisture from the environment onto the non-SLIPS occurs again. In some embodiments, the process is repeated to provide a moisture collection device.

Liquid Identification/Sorting Device

Figure 11:
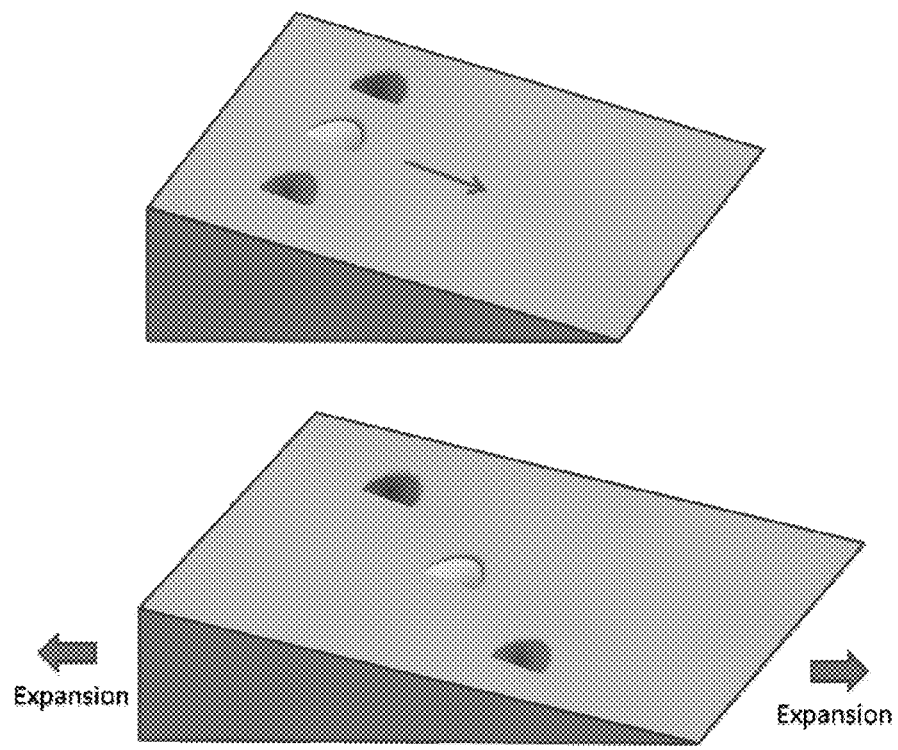
FIG. 11 shows a liquid identification/sorting device utilizing dynamic transition between SLIPS and non-SLIPS structures in accordance with certain embodiments.

In certain embodiments, the dynamic SLIPS structure is utilized to carry out the identification and sorting of liquids based on their mobility characteristics. For example, as shown in FIG. 11, a liquid-infused surface of gradient thickness or gradient Young's modulus is designed. The Young's modulus (E) can be expressed by dividing the tensile stress ($\sigma$) by the tensile strain ($\in$): $E=\sigma/\in$, while the stress equals to the force (F) on average crossing area (A): $\sigma=F/A$. This results in $E=F/(\in \times A)$. When the membrane is stretched, at an instantaneous moment, F is constant, and thus $\in$ is inversely proportional to A (if E is constant) or E (if A is constant), which means a different strain results based on the membrane thickness or Young's modulus. Hence, a gradient strain could be achieved when the membrane is in gradient thickness or modulus. Since liquids of different surface tension have different mobility on the dynamic SLIPS at different strain/tension, in some embodiments these liquid droplets on the prepared gradient surface slide and be pinned to different positions of specific strain, therefore a stretch-induced sorting is achieved. In further embodiments, a SLIPS membrane is provided with the gradient cross-linking density along the membrane. In this case, for a given force, different regions experience different local strains. The droplets of different surface tensions travel until they reach the region where the local strain/stress value exceeds its threshold for pinning.

Smart Switch on Chemical Catalysis

Figure 12:
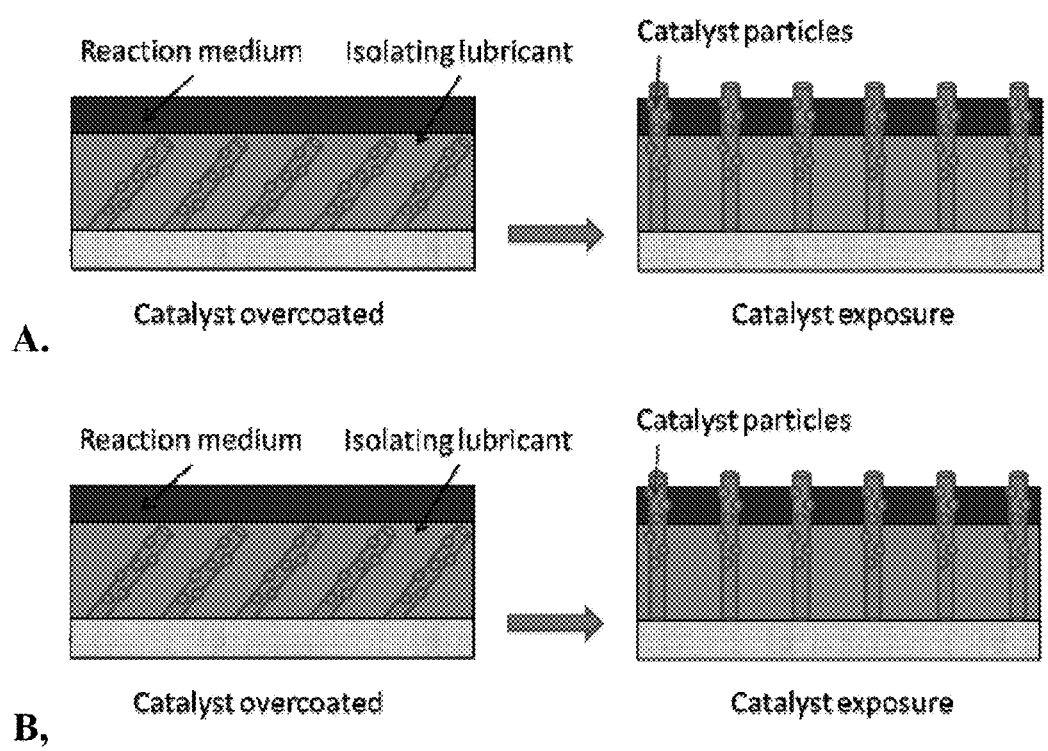
FIGS. 12A-B show chemical reaction switching devices which utilize dynamic transition between SLIPS and non-SLIPS structures in accordance with certain embodiments.

In certain embodiments, the dynamic SLIPS structure is utilized to switch on and off chemical reactions as desired. For example, as shown in FIGS. 12A-B, a switchable chemical catalysis is obtained on dynamic SLIPS by implanting catalyst particles on the solid host. As shown in FIG. 12A, on the left, when a SLIPS structure is formed, the catalyst is covered with the lubricant. Particularly, the lubricant is utilized so that it repels away any reactants to further ensure that no reactants are exposed to the catalysts to trigger any undesired chemical reactions. As shown on the right, when the reaction is desired, upon application or removal of a suitable stimulus, a non-SLIPS structure forms whereupon the catalyst particles and/or the underlying substrate microstructures are designed to attract the reactants. For example, in some embodiments, the solid host is dynamically bent or shrunk by using responsive materials such as light- or temperature-sensitive polymers, magnetic responsive polymers, dielectric elastomers and the like to expose the catalyst particles to the reaction medium. FIG. 12B shows another embodiment of smart switch on chemical catalysis utilizing the structure/morphology change of the surface. As in FIG. 12A, the catalyst particles are pre-implanted on the solid host, which is dynamically bent/shrunk by using the responsive materials such as light, temperature sensitive polymers, magnetic responsive polymers, dielectric elastomers, etc. Moreover, in some embodiments the catalyst particles are designed to be immiscible with Liquid B to ensure that the catalyst is fully exposed (i.e., a thin coating of Liquid B does not remain over the catalyst particles) after Liquid B has receded. As a result, the reactants are attracted to and be exposed to the catalyst particles when Liquid B's levels are lowered, triggering the chemical reaction.

Smart Water-Repelling Tent with Adaptive Light Transmission

Figure 13:
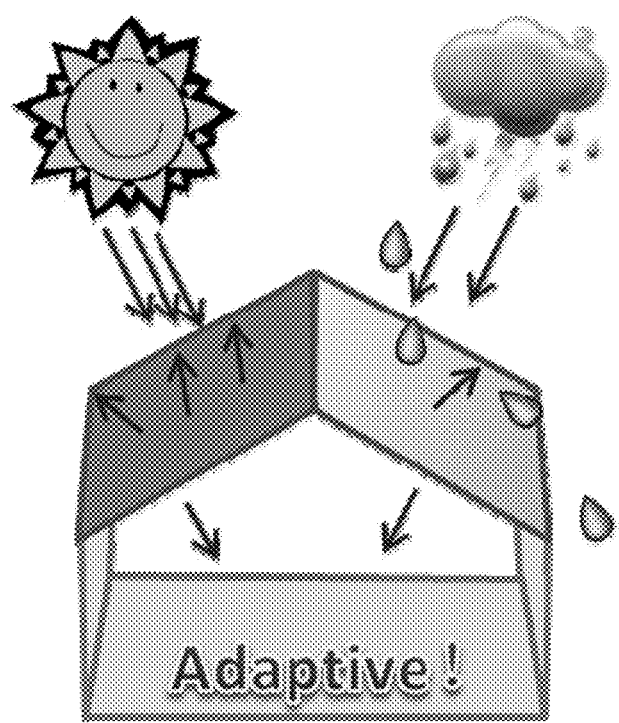
FIG. 13 shows a smart tent with adaptive light transmission and water-repellant properties utilizing dynamic transition between SLIPS and non-SLIPS structures in accordance with certain embodiments.

In certain embodiments, the dynamic SLIPS structure is utilized to provide a smart tent with adaptive light transmission. For example, as shown in FIG. 13, dynamic SLIPS structure described herein is used as smart tent that blocks light on a dry sunny day, but becomes both transparent and water-repellent on a dim rainy day. For example, in some embodiments the substrate is designed to be optically clear. Upon stretching the tent on a dry sunny day, the lubricant recedes into the porous elastic substrate and become opaque due to scattering. This provides a surface that is able to block light on a dry sunny day as excess sunlight might not be desired. However, when the weather becomes cloudy and even rainy, the release of the stretched tent causes the lubricant to file the pores again and to provide a SLIPS structure and restore transparency and water repellency. Upon formation of the SLIPS structure, the rain droplets freely slide away providing a clean surface and maximizing light transmission. Moreover, in some embodiments the SLIPS structure provides the added benefit of a self-cleaning surface that removes undesired debris collected during the non-SLIPS state as the rain droplets collect the undesired debris and carry them away from the surface as well.

Wound Dressing

In certain embodiments, the dynamic SLIPS structure is utilized to provide a smart tissue bandage. In some embodiments, a bandage is applied to the tissue of a wound (such as a burn) in the non-SLIPS state, to allow adhesion to the wound. Then, the non-adhesive, SLIPS state is activated to allow easy removal of the bandage from the underlying tissue. In further embodiments, tissue cells are grown on a non-SLIPS structure based bandage, whereupon the tissue cells adhere/grow/align due to the enhanced adhesion provided by the non-SLIPS structure. Then, the bandage is applied to the wound area where the tissue cells are transferred to treat the wound. Then, the bandage is released after converting it into a SLIPS structure when the wound has been treated to a desirable degree.

An important application of switchable adhesion using dynamic SLIPS mechanisms is for wound dressings (bandages) that are reversibly adherent or removable from the tissue surface. In wound repair there are stages when the growing tissue is very sensitive to mechanical damage, such as the removal of a bandage dressing. This sensitivity is particularly important for severe wounds, such as large scale burns. Bandages that have a dynamic, switchable adhesion are particularly important to allow the bandage to be removed from the wound surface without damaging the underlying tissue.

Figure 32:
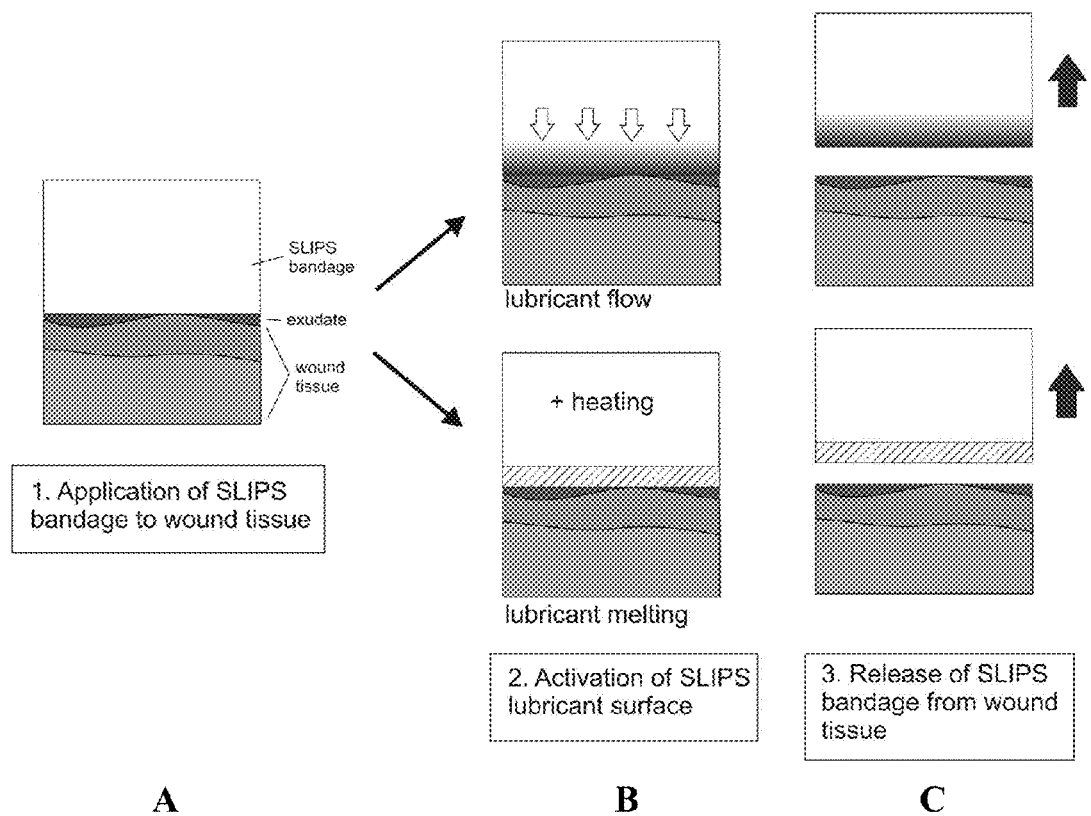
FIGS. 32A-C show schematics of a SLIPS bandage in adherent contact with the tissue of a wound and mechanisms to render the bandage non-adhesive for removal.

FIG. 32A shows a SLIPS bandage in adherent contact with the tissue of the wound. The bandage works to absorb the exudate fluid from the wound, and while in application to the wound, the bandage does not have liquid lubrication present. FIGS. 32B-C show two mechanisms to allow the activation or introduction of the lubricant layer to the SLIPS bandage, to make it non-adhesive. The mechanism shown at the top of FIGS. 32B-C functions by flowing lubricant to the bandage/tissue interface, through the SLIPS bandage, to allow the removal of the bandage. The mechanism shown at the bottom of FIGS. 32B-C functions by causing a phase transition (melting) of the lubricant layer. Both mechanisms cause a distinct change in the adhesion strength of the bandage to the underlying tissue, so that the bandage is removed easily with minimal disruption to the healing tissue and clotted blood or exudate.

Other Applications

Numerous other applications can be envisioned. For example, structural materials, (e.g., tents, windows, shades, etc.) that block the excessive light and switch off the unneeded slippery properties on a bright, clear sunny day, but become transparent to get more light and also repellant for rain and snow, on a rainy, gray-sky day can be envisioned. As another example, sensors that self-report the accumulation of a certain component due to the degradation of the slippery function can be envisioned. Medical pipes, transfusion systems, catheters and the like that allow or prohibit the flow of fluids by simple application of an external field (e.g., stretching of the tube) can be envisioned. This property is an important addition to microfluidics, making fluidic channels switchable, controllable, and changing their transport characteristics and drag in a dynamic, tunable way.

EXAMPLES

Example 1: On/Off Switching

Figure 14:
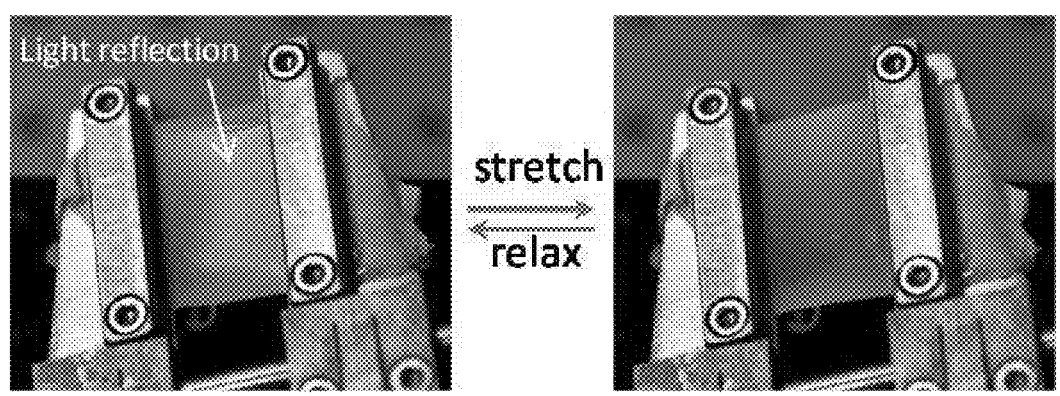
FIG. 14 shows images of exemplary SLIPS and non-SLIPS structures formed as a function of applied mechanical strain in accordance with certain embodiments.

The dynamic performance of optical transmission and liquid mobility control are attributed to the reversible flow and distribution of the Liquid B during the mechanical stretch process, which further influences the apparent optical diffraction index and wettability of the surface (see FIG. 5A). Since the volume of Liquid B remains constant, changing the surface area of the underlying substrate changes the filling distribution of Liquid B on the surface, which influences the filling fraction and the film thickness of Liquid B on the surface. In other words, the layer of Liquid B on the porous surface recedes inward to the porous regions when a stretch is applied, which makes the surface seem to be "dry". FIG. 14 shows that the film exhibits some light reflection at a relaxed state due to the layer of Liquid B coating the solid, while after stretching, the light reflection is no longer present, making the film appear "dry."

Figure 18A:
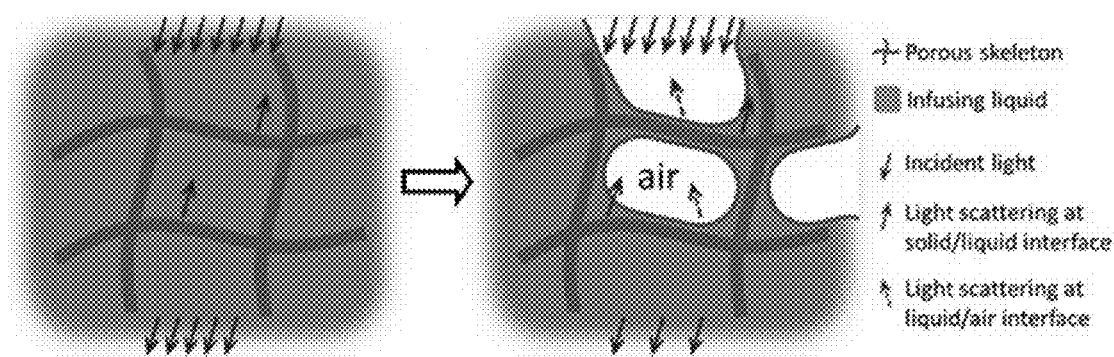
FIG. 18A shows a schematic illustration of the change in optical transmission under stretch. Air pockets induced by stretching lead to increased light scattering in accordance with certain embodiments.
Figure 18B:
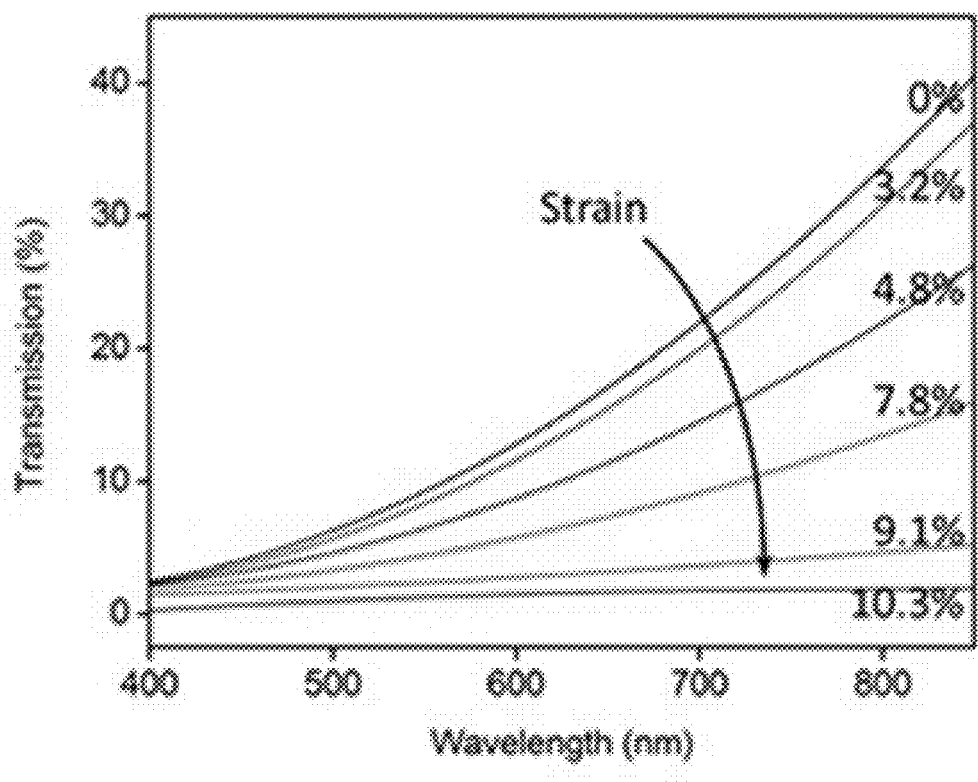
FIGS. 18B and 18C show in-line optical transmission measurements in the visible light range (FIG. 18B) and in the near-infrared range (FIG. 18C) under mechanical stretch in accordance with certain embodiments.
Figure 18C:
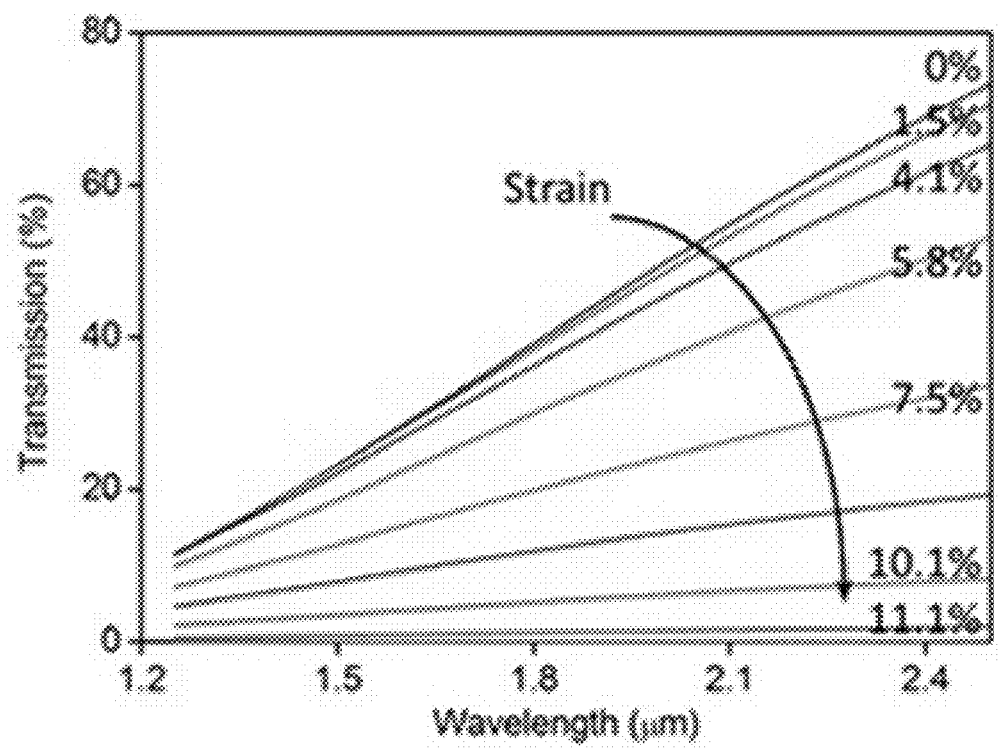
Figure 18D:
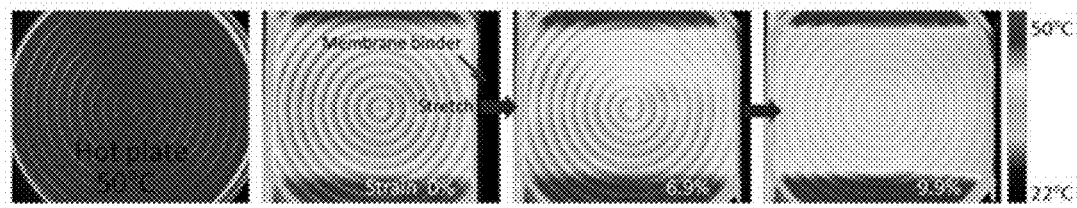
FIG. 18D show images taken with an IR camera showing the induced change in the IR transmission through an exemplary dynamic SLIPS material placed in front of a hot plate. The color gradient from black to light gray indicates the IR signal emission from high to low. Most of the IR signal is scattered by the shielded membrane upon stretching in accordance with certain embodiments.

Moreover, during stretching, more air occupies the micro/nanoscale porosity of the surface, which makes the surface opaque (see FIG. 18A). When the surface is relaxed, the surface area of the film decreases, and the imposed liquid flows to refill the film, making the film optically transparent again.

Figure 15:
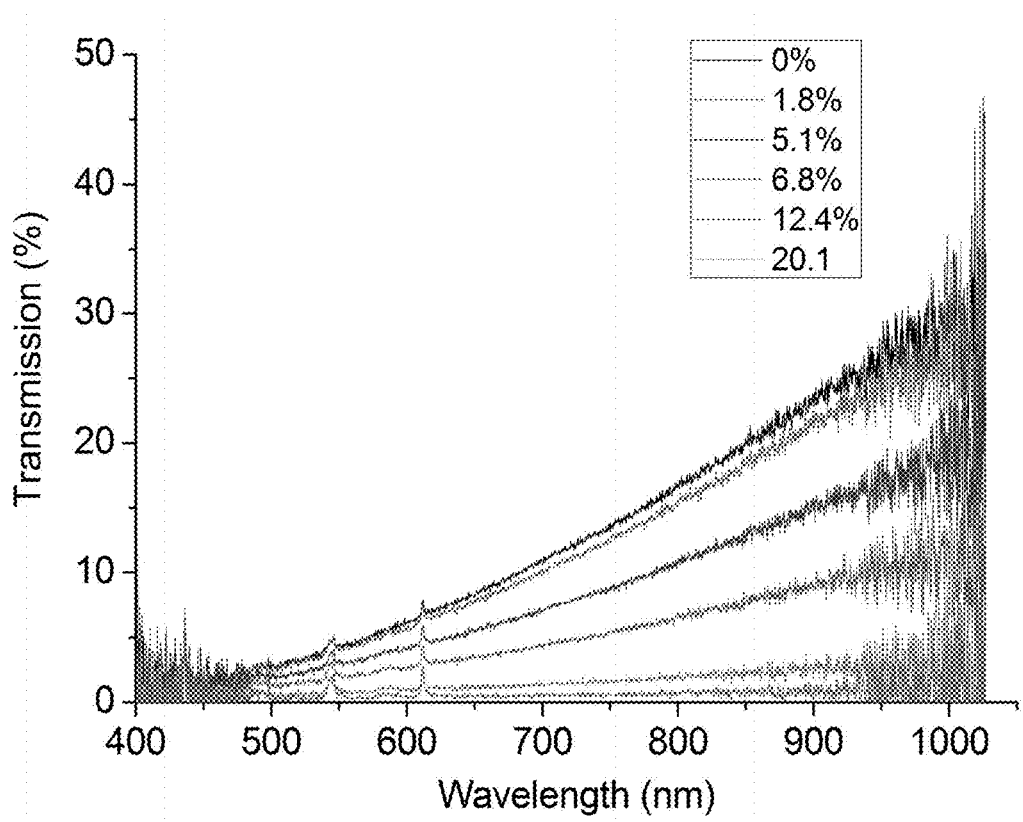
FIG. 15 shows experimental optical transparency graphs for the transition from SLIPS to non-SLIPS structures as a function of applied mechanical strain in accordance with certain embodiments.
Figure 16:
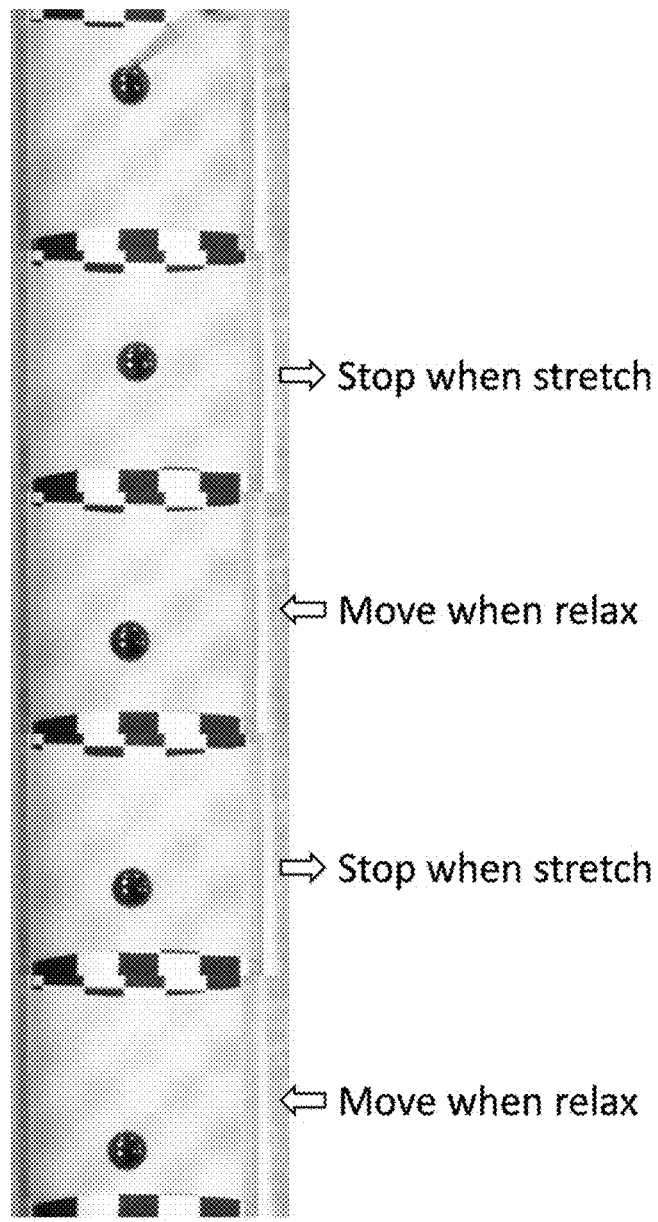
FIG. 16 shows exemplary images of a crude oil that either moves or stops over SLIPS and non-SLIPS structures formed as a function of applied mechanical strain in accordance with certain embodiments.

To illustrate, FIG. 15 shows the optical transparency of a Teflon film filled with a perfluoro-fluid as Liquid B. As shown, optical transparency is controlled from about 40% to about 0% as a function of the applied strain. As shown, with greater applied strain, light transmission decreases.

Moreover, Liquid A's mobility is switched on and off as desired. For example, when structure is in the relaxed (SLIPS) state, the structure exhibits its original property of liquid repellency and slipperiness, as Liquid B forms an ultra-smooth surface. In this state, the droplets move freely on the surface. In contrast, when the film is in the stretched state, Liquid A is pinned on the roughened surface. This is demonstrated in FIG. 16 using a drop of paraffinic crude oil. As shown, the crude oil is dynamically controlled to move or stop on the prepared surface under reversible mechanical stretch. Accordingly, a valveless flow control system is provided.

Example 2: Continuous Tunability of SLIPS Characteristics

The dynamic behavior of the SLIPS structure in this example is based on the concept that any deformation of the substrate that changes the pore size can cause the liquid to respond. As a result, fluid from the coating layer (Liquid B) is drawn into (out of) the expanding (contracting) pores, altering surface topography (see FIG. 17A). This response can be quantitatively predicted by relating the induced pressure change to the substrate deformation and the interfacial tension. Initially, the pressure of the infused liquid (Liquid B) is balanced with the pressure outside. For example, for a mechanically sensitive substrate, when a tensile stress $\sigma$ is applied, the pressure of the liquid inside the porous matrix decreases. In the instantaneous state, before the liquid molecules have started to move, the change in pressure depends on the tensile stress as $\Delta P = -\sigma/3$. Driven by the pressure drop, the excess liquid layer can thin and cave inwards. An equilibrium state is reached when the pressure difference is balanced by the surface tension of the liquid, $-\Delta P = 2\gamma/r_m$, where $\gamma$ is the interfacial energy between the infused liquid and the outside media and $r_m$ is the radius of the meniscus curvature (see FIG. 17A). When the tensile stress is released, the pressure of the liquid increases back to close to the pressure of the outside media and the liquid moves outwards, forming a flat interface again. Thus the hybrid material is expected to provide a dynamic fluidic interface that reversibly varies from smooth to textured in response to stimuli sensed by the substrate.

Figure 17A:
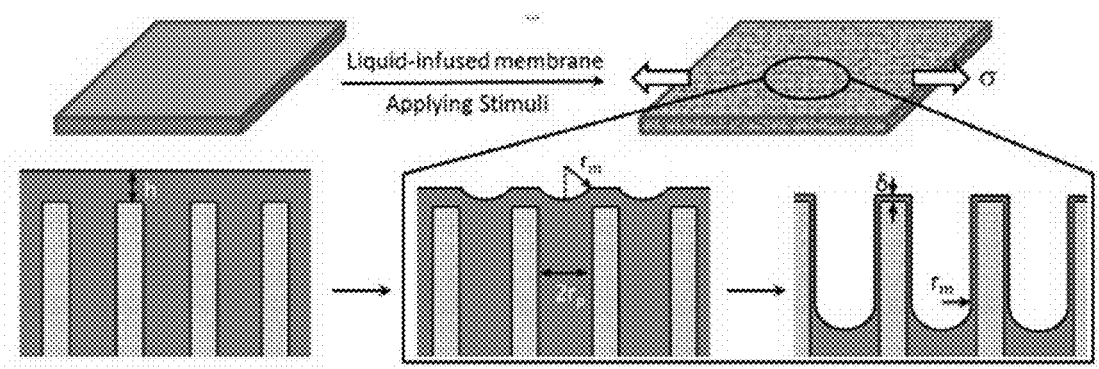
FIG. 17A shows the topography of a liquid film on an elastic porous substrate being reconfigured in response to external stimuli (for example, mechanical stretch). The porous matrix is illustrated as composed of unit pores of radius $r_p$. Initially a thin layer of excess liquid of thickness h overcoats the substrate and forms a flat interface. Under small tension, the film surface undulates. Under higher tension, the liquid interface begins to retreat into the expanded pores. A rough surface develops with a meniscus radius $r_m$ in accordance with certain embodiments.
Figure 17B:
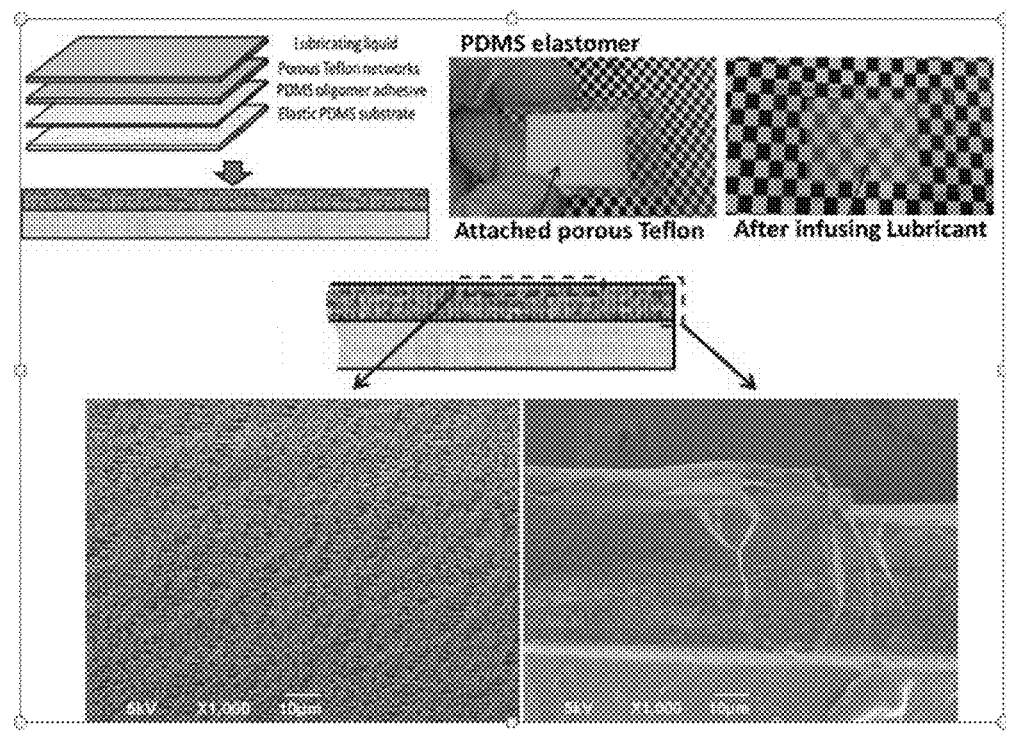
FIG. 17B shows an exemplary material construction from a PDMS base layer, porous Teflon, and infused liquid (left, top) and the corresponding optical images for the substrate without (middle, top) and with (right, top) the liquid. A thin layer of PDMS precursor pre-coated on the PDMS firmly adheres the base to the Teflon nanofibers with a slight penetration into the porous membrane (bottom) in accordance with certain embodiments.

An exemplary dynamic SLIPS structure was built by combining a low surface energy fluid that infiltrates a stretchable porous matrix on an elastic base (see FIG. 17B). As the porous matrix, a Teflon membrane (composed of nanofiber networks, ~50 μm thick, average pore size 200 nm) that can absorb and hold fluids was utilized. Porous Teflon membranes with average pore size of ~200 nm and thickness of ~45 μm were purchased from Sterlitech Corporation, Wash., USA. These membranes were used as received without further modification. An elastic PDMS membrane (~0.5-1.5 mm thick) was attached to the porous Teflon membrane, using a thin layer of PDMS oligomer as adhesive, such that stretching the base stretches the porous matrix while maintaining the mechanical integrity of the system (see FIG. 17B). The hybrid membrane was integrated with an elastic PDMS film (0.5~1.5 μm thick) and the porous Teflon membrane, by using a thin layer of PDMS oligomer as adhesive. The PDMS film was firstly activated under $O_2$ plasma treatment for 10 s. A thin layer of PDMS curing precursor (Dow Corning Sylgard 184, 1:10) was then coated on the substrate, and placed in a 70° C. oven for 15-20 min to obtain sticky oligomer. The porous Teflon membrane was attached on the sticky layer under the pressure of ~1000 Pa. The sticky PDMS oligomer would slightly penetrate into the porous Teflon membrane and thus firmly attached the nanofiber networks to the elastic substrate. Then the integrated multilayer was placed in the 70° C. oven for further 1-2 h to ensure full curing.

A perfluorinated liquid (for example, DuPont Krytox 103 perfluoropolyether) that can wet and wick into the porous membrane was selected as the fluid layer. Particularly, the lubricating fluid used for the experiment was perfluorinated fluid, DuPont™ Krytox® 103 perfluoropolyether. The density and kinematic viscosity of Krytox 103 at 25° C. are 1920 kg/m$^3$ and 0.82 cm$^2$/s, and the optical refractive index is in the range of 1.296-1.301, respectively. The test liquids were obtained from Sigma Aldrich, including n-hexane, octane, decane, dodecane, hexadecane, ethanol and silicone oil (AR20). The DI water was obtained from miniPore purification system. A liquid tracer, DFSB-K175 Orange, was used to dye the organic liquids, and Rhodamine B was used to dye water. The interfacial tension for Krytox 103 with different media was measured using a pendant drop method at ambient conditions, as shown below. Densities of the individual liquids are provided by the manufacturer specification.

TABLE 1

Measured Interfacial Tension for Krytox 103 and different media.

| Medium | Interfacial Energy with Krytox 103 (mN/m) |
| --- | --- |
| Air | 17.4 ± 0.1 |
| Water | 57.2 ± 0.1 |
| Ethanol | 8.3 ± 0.2 |
| Silicone Oil (AR20) | 8.2 ± 0.3 |
| Hexadecane | 8.8 ± 0.3 |
| Dodecane | 7.5 ± 0.3 |
| Decane | 6.6 ± 0.2 |
| Octane | 5.4 ± 0.3 |
| Hexane | 3.5 ± 0.1 |

Lubricating fluid was added onto the surfaces by pipette to form an overcoated layer. With matching surface chemistry and roughness, the fluid spreads onto the whole substrate through capillary wicking. The thickness of the overcoated layer is controlled by the fluid volume given a known surface area of the sample. The surface energy match between the solid matrix and the liquid, together with the matrix roughness and the liquid's immiscibility with most other liquids, ensures that the liquid stably adheres to the matrix. The resulting system integrates the characteristics of a smooth liquid interface with the poroelasticity of the substrate that avails high roughness and porosity, along with the liquid's ability to flow and redistribute.

The liquid pressure of a porous matrix infused with liquid under a mechanical load was calculated by using commercial finite element software, ABAQUS. A layer of a liquid infused porous matrix of 50 um thickness bonded to a PDMS substrate of 1 mm thickness was simulated. The width and length of the system were 3 cm and 4 cm. The layer of liquid infused matrix was modeled as a poroelastic material. The material parameters used in the calculation include Young's modulus 20 MPa, Poisson's ratio 0.2, permeability $4 \times 10^{-14}$ m$^2$, liquid density 1920 kg/m$^3$ and liquid viscosity $8.2 \times 10^{-5}$ m$^2$/s. The PDMS substrate was modeled as an elastic material with Young's modulus 2 MPa, and Poisson's ratio 0.49. Three types of mechanical loads including tension, bending and poking were simulated individually. The "Soil" type of solver was selected in the simulation. The instantaneous liquid pressure was calculated by applying the mechanical load in a very small time step which is five order of magnitude smaller than the time for diffusion to reach equilibrium. A zero flux boundary condition was also imposed on the surface of the top layer.

Figure 17C:
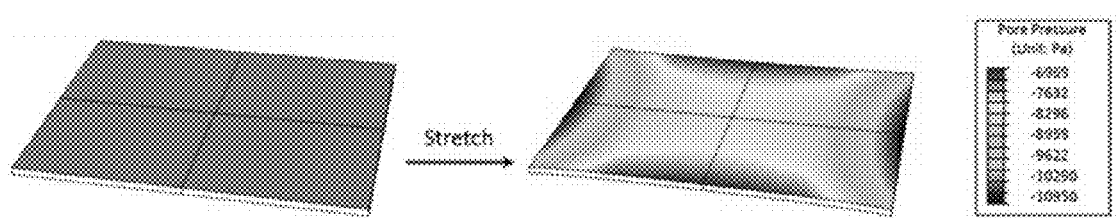
FIG. 17C shows the results of a finite element calculation of the instantaneous pore pressure of the liquid infused porous Teflon attached to a PDMS substrate. When a mechanical load is applied, a field of negative pore pressure is generated throughout the porous membrane in accordance with certain embodiments.

The finite element calculation indicates that applying a tensile stress to this system results in a pressure drop throughout the porous matrix. The liquid pressure differential was initially set to zero everywhere in the liquid-infused membrane, and the instantaneous pressure was calculated just after a lateral stretch was applied. As shown in FIG. 17C, a field of negative pressure is built up in the membrane. Consistent with the prediction discussed above, the experimental observations indicate that this pressure drop drives the overcoating fluid to retreat into the pores. Macroscopically, as the surface changes from flat to rough, the optical properties are expected to change. Accordingly, a shining reflection is observed when the material is in the relaxed state but disappears when the applied strain is larger than a critical value, indicating a transition between the smooth and structured surface, respectively. This transition also causes a change in the material's ability to transmit light.

Figure 17D:
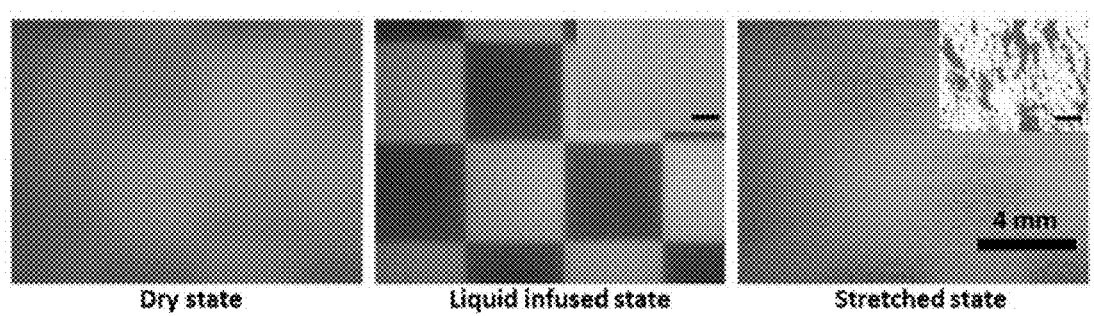
FIG. 17D shows optical images demonstrating the stretch-induced surface changes resulting from liquid redistribution. Insets: Microscopic images (scale bar: 50 μm) showing the appearance of unfilled air gaps in accordance with certain embodiments.

The membrane stretch was carried out by a home-made uniaxial stretcher, with a thread pitch of 0.6 mm. The membrane was mounted by screwed clippers on a pair of arms of the stretcher. The evolution of the distance between the arms was measured during the experiment, which was further used to calculate the membrane strain. As shown in FIG. 17D, the liquid-infused matrix shows enhanced light transmission compared to the opaque pure porous Teflon membrane, due to the liquid's ability to fill the air pockets in the membrane and effectively reduce the light scattering at the surface/air interface. When the infused membrane is stretched, the transparent surface becomes opaque, as the liquid redistribution under membrane stretch generates partially air-filled pores (see insets in FIG. 17D).

The sensitivity of the film surface properties to matrix deformation makes it possible to finely tune the optical behavior over a continuous, wide range in response to stimuli. The commercial porous Teflon is constructed from nanofiber networks forming interconnected pores of distributed sizes. As the tensile stress is applied, the liquid front pierces through pores with radius $r_p$ if $-\Delta P > 2\gamma/r_p$. The liquid front retreats into the matrix until it meets a pore small enough to balance the pressure difference. As the stress is increased, more pores are broken through in the equilibrium configuration. Consequently, a larger area of unfilled open pores is formed in the membrane and more light is scattered at the liquid/air interface (see FIG. 18A).

This tunability of optical transmission was demonstrated by gradually stretching the liquid-infused membrane. Optical transmission measurements were carried out using a UV-Vis spectrophotometer for visible light (400 nm to 850 nm wavelength) and a Bruker Hyperion 3000 FTIR Microscope for NIR light (1.25 μm to 2.5 μm). All optical transmission measurements were normalized with respect to the transmission spectrum of air at room conditions. In-line light transmissions were recorded in both instruments. Lower light transmission in both visible and near-infrared (NIR) wavelengths is progressively obtained as the strain is increased (see FIGS. 18B-18C), until the membrane finally becomes opaque under either visible or NIR wavelengths.

Thermal imaging measurements were performed by using an IR camera (FLIR SC5000), which operates in the 2.5 to 5.1 μm waveband. A blackbody calibrator (OMEGA BB701) which was set at 50° C. was used as background. The stretcher was placed between the camera and the hot background. The distance between the membrane and hot background is 4 cm. As demonstrated by an IR camera (FLIR) which collects the light of wavelengths 2.5-5.1 μm, the signal from a hot background (50° C.) is effectively scattered by the surface as it is stretched (see FIG. 18D).

The continuous tunability of the liquid film morphology also provides a way to control the surface wetting properties. The flat, atomically smooth liquid interface in the relaxed state serves as a lubricating layer and allows liquid drops to slide freely, while the rougher film topography in the stretched state leads to increased contact angle hysteresis that inhibits motion, decelerates droplets and eventually pins them on the surface (see FIG. 19A).

Figure 19A:
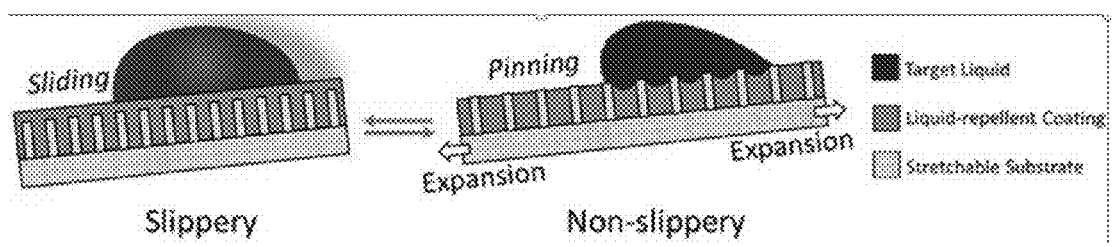
FIG. 19A is a schematic showing the control mechanism: a droplet of test liquid changes from sliding to pinning under external stimuli (for example, mechanical stretch) as the film surface reconfigures from flat to rough in accordance with certain embodiments.
Figure 19B:
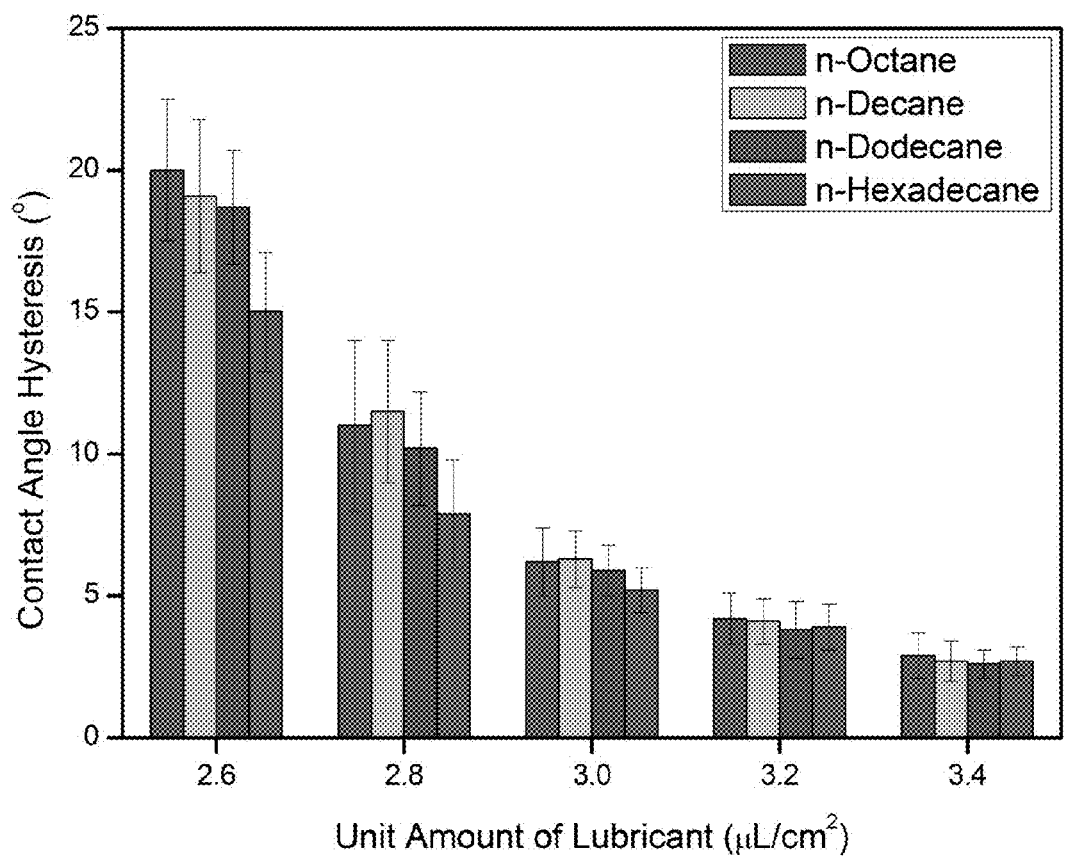
FIG. 19B shows the contact angle hysteresis for different hydrocarbons as a function of amount of lubricant in accordance with certain embodiments.
Figure 19C:
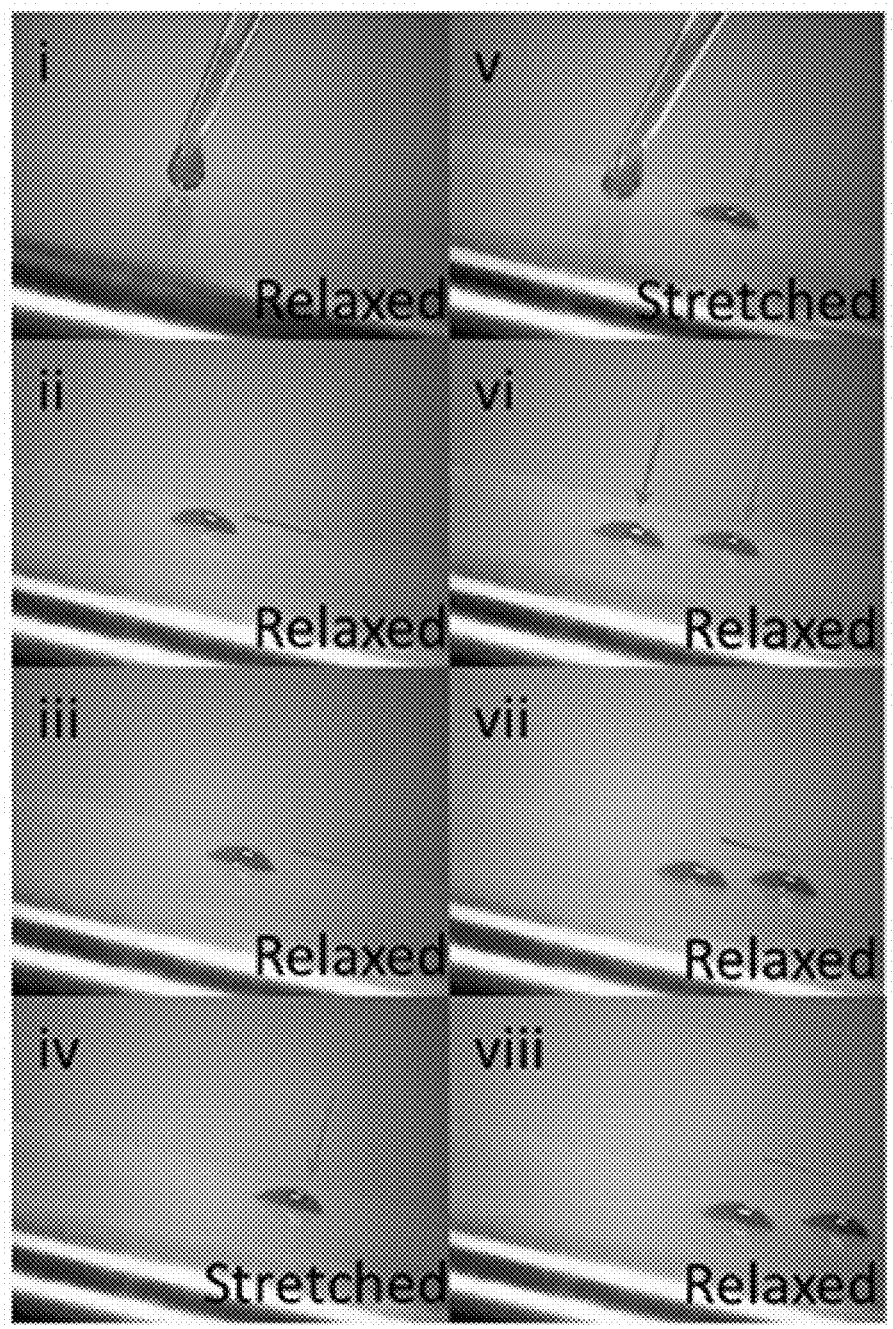
FIG. 19C shows a demonstration of the control of the mobility of silicone oil drops on the dynamic slippery surface under stretch. A drop of silicone oil was deposited on a tilted surface, sliding down (i~iii) until a stretch was applied (iv). A second oil drop deposited on the stretched surface was also pinned (v). Both of the drops slid down when the strain was relaxed (vi~viii) in accordance with certain embodiments.

FIG. 19B shows a comparison of contact angle hysteresis as a function of lubricant amount on an unstretched membrane. The tested liquids include n-octane (n-$C_8H_{18}$), n-decane (n-$C_{10}H_{22}$), n-dodecane (n-$C_{12}H_{26}$) and n-hexadecane (n-$C_{16}H_{34}$). As shown in FIG. 19C, the contact angle hysteresis is smaller than 5° on the as-prepared membrane when the unit lubricant amount is larger than 3.0 μL/cm². Additionally, no oil residue was detected on the membrane after the oil drop slid away upon release from pinning, consistent with the lubricating film remaining continuous rather than allowing the oil to wet and foul the underlying solid. This surface thus provides a simple, stimulus-responsive way to fine-tune liquid mobility and transport in real time, with a level of dynamic control previously unachievable with other state-of-the-art techniques.

FIG. 19C demonstrates this ability by presenting the behavior of a drop of silicone oil (6 μL) on a tilted surface. Sliding angle measurements were used to test oil mobility on the hybrid membrane. Oil sliding angles were recorded by a contact angle measurement system (KSV CAM101) at room temperature. The droplet volume for the measurement was 9 μL (unless otherwise specified) and the macroscopic droplet profile was captured through a camera equipped with an optical system for amplification of the captured images. In measuring the contact angle hysteresis, the surface was tilted with respect to the horizontal plane until the liquid droplet started to slide along the surface. As shown, the oil slides on an undeformed substrate, but is pinned in place when a strain of 6% is applied (i~iv). In the stretched state, even a newly deposited oil drop is immobilized and stays where it is placed on the surface (v). When the stress is released, both of the drops begin to slide (vi~viii).

Figure 19D:
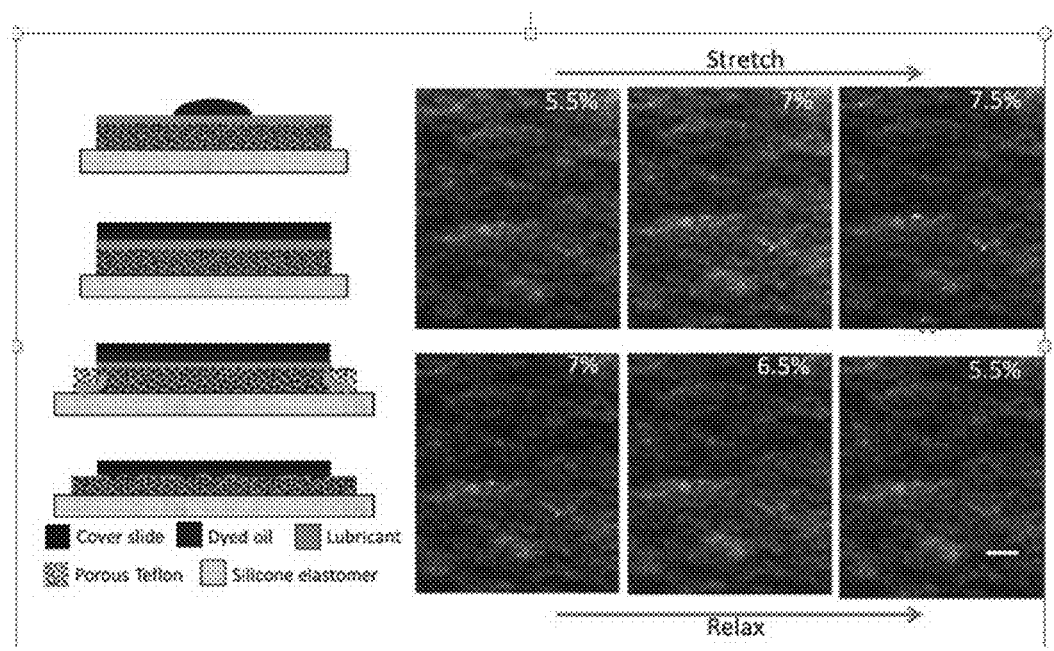
FIG. 19D shows a schematic of the experimental design and experimentally obtained micrographs demonstrating interaction between target liquid and the underlying substrate in accordance with certain embodiments.

The changes in mobility correlate with reconfiguration of the film under reversible stretch, and confocal imaging further confirms that the lubricant/oil interface becomes rough when the membrane is stretched and returns to flat when the stress is relaxed. The interaction between the lubricant and impinging oil was imaged by using Zeiss LSM 720 laser confocal microscope and Zen software. Silicone oil that dyed with the liquid fluorescent tracer, DFSB-K175 Orange was used as probe oil. The integrated membrane infused with 3.0 μL/cm² unit amount of Krytox 103 was used as substrate. FIG. 19D shows the interaction between the target liquid and the underlying substrate. Sequential images for the liquid/membrane interface at different stain. The images are shown in gray style where the bright area represents the fluorescent signal. Bright dots (circled areas) were observed as the strain increased (7.5%), and these disappeared when the film was relaxed (5.5%). Scale bar: 20 μm.

Figure 19E:
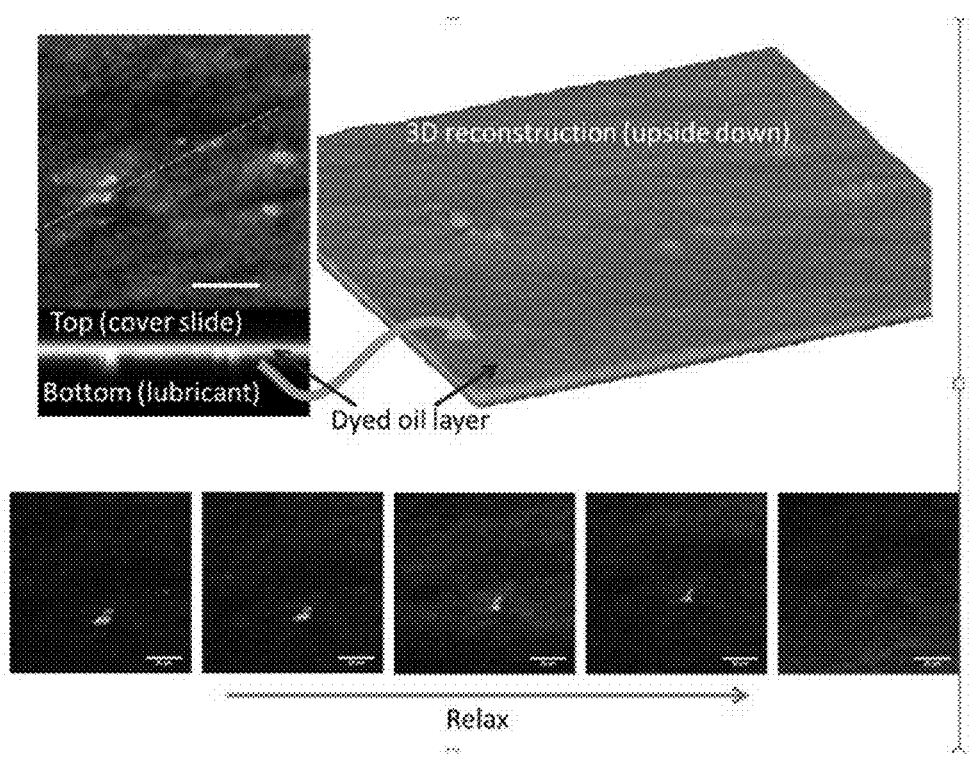
FIG. 19E shows the in situ observation of the retreatment of the penetrated oil when the strain is relaxed in accordance with certain embodiments.
Figure 19F:
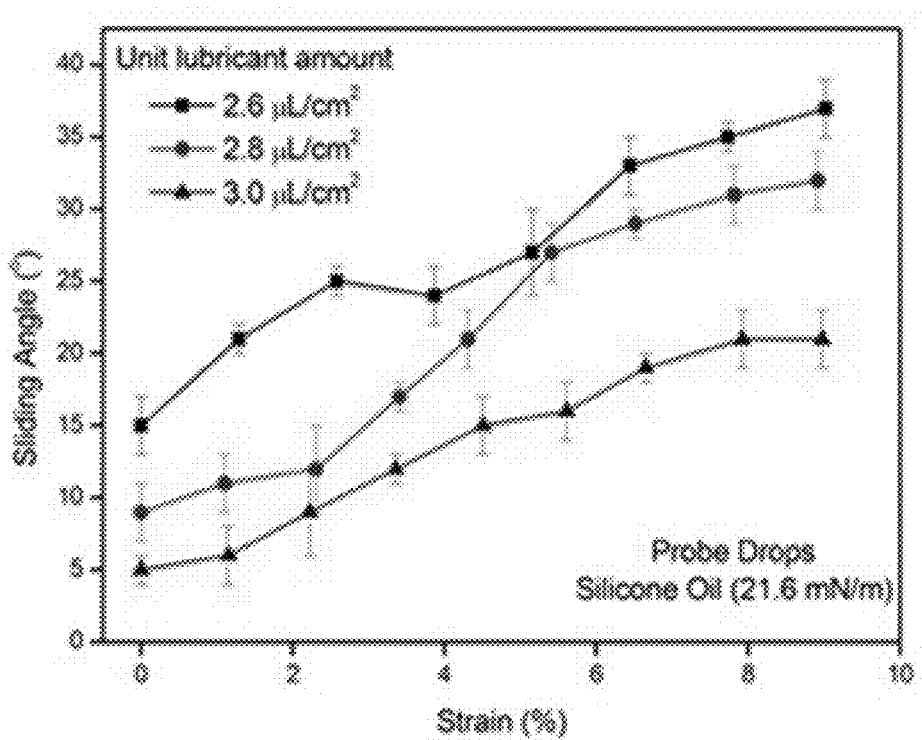
FIG. 19F shows a comparison of sliding angle (silicone oil) as a function of strain on the membrane with different amounts of infused fluid in accordance with certain embodiments.
Figure 19G:
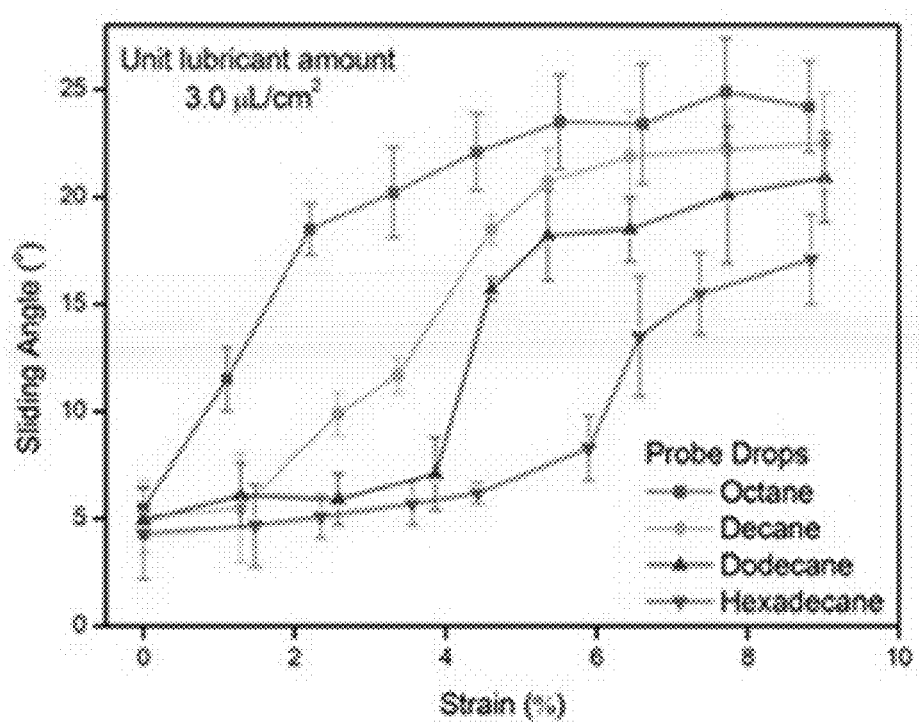
FIG. 19G shows tuning of the oil sliding angle as a function of strain for test droplets of different interfacial tensions. Perfluoro-lubricant (Krytox 103) with a unit amount of 3.0 μL/cm$^2$ was used as the infused fluid in accordance with certain embodiments.

In some embodiments, the oil/lubricant interface is not clearly detected when an oil drop is deposited directly on the slippery surface, because the thick bulk oil adsorbs most fluorescent signal, providing very bright background. In such instances, an alternate method to reveal the morphology of the interface was utilized. A 4 μL drop of dyed silicone oil was firstly deposited on the liquid-infused membrane, and then a cover slide (22×22 mm) was placed on the drop. Thus, the oil was flattened and spread between the cover slide and the underlying substrate, forming a thin oil layer with a thickness between 10-15 μm. Then in situ confocal imaging was carried out to capture the interface evolution under stretch. A time series mode was used to track the in situ evolution at the interface during stretch. A Z-stacking mode (along the dashed line) was used to capture the morphology of the lubricant/oil interface at different strains. The slicing distance is 1.07 μm. As shown in FIG. 19E, the bright layer represents the dyed oil layer between the cover slide and the slippery surface. The Z-stacking image confirms that the bright dots resulted from the partially penetration of dyed oil into the lubricant layer under stretch, forming a kind of rough contact. Scale bar: 20 μm. As the strain is relaxed, the bright dot gets smaller and finally disappears.

Example 3: Identifying Liquids by Strain-Related Mobility Profiles

In addition to directly manipulating moving droplets, in some embodiments the infused surface is easily tuned to different stimulus-sensitivity levels, with droplets of different surface tensions displaying unique sensitivity profiles. When a tensile stress is applied, the liquid pressure inside the porous matrix instantly drops to below the pressure outside, which provides a driving force for the excess lubricant layer to cave inward. As the lubricant flows in, the pressure difference is also released. If the overcoating lubricant layer is thick enough, it fills the newly formed gaps and equalize the internal and external pressure without disrupting the flat outer lubricant-oil interface. In practical terms, the thickness h is controlled by controlling the amount of lubricant. For a porous matrix of bulk modulus K, the thickness of the excess lubricant layer h relative to the thickness of the porous membrane H does not exceed the increased volume of the matrix induced by the tensile stress, h/H<σ/3K. Under these conditions, an equilibrium configuration of the oil-lubricant interface is reached when the liquid pressure difference is balanced by the interfacial tension $\gamma_{LO}$, that is, $-\Delta P=2\gamma_{LO}/r_p$. Therefore, for a given interfacial tension, a smaller amount of lubricant leads to a larger pressure difference at equilibrium, and the interface is pinned at a smaller pore size. This relationship allows the deformation sensitivity threshold to be straightforwardly tailored by varying the amount of lubricant. At the same time, for a given amount of lubricant, a lubricant-oil combination with a smaller interfacial energy also requires a smaller pore size to stop the retreat of the interface. Consequently, less strain is required to disrupt the flat interface and pin droplets with lower interfacial tensions.

The tuning of mechanical sensitivity, and the differential responsiveness of different droplets, are illustrated in FIGS. 19F and 19G. FIG. 19F shows the sliding angles for silicone oil drops on membranes infused with different amounts of lubricant (2.6-3.0 μL/cm²) under different membrane strains (0-10%). In general, the sliding angle (the tilt required for the droplet to slide) increases with increasing strain for a given amount of lubricant, as the surface becomes rougher. However, for a given strain, membranes with less lubricant have higher sliding angles. Conversely, it takes less strain to reach a higher sliding angle on a surface with less lubricant, consistent with less stretch leading to greater roughness and pinning. To test how lubricant/oil interfacial energy influences the sensitivity to strain, Krytox 103 (17.4 mN/m; 3.0 µL/cm$^2$) was utilized as the lubricant, and the sliding angles were compared as a function of strain for hydrocarbon oils of different surface energies: octane (21.6 mN/m), decane (23.7 mN/m), dodecane (25.4 mN/m) and hexadecane (27.3 mN/m). The sliding angles are shown in FIG. 19G. Oils of lower surface tension have a sharp increase when a small strain is applied. For example, a small strain change from 0 to ~2% increases the sliding angle from 5° to 18° for a droplet of octane. The same strain change has no discernible effect on hexadecane, which requires ~9% strain to reach a sliding angle close to 18°. The system is thus sensitive enough to distinguish among a variety of low-surface-tension liquids.

Figure 20A:
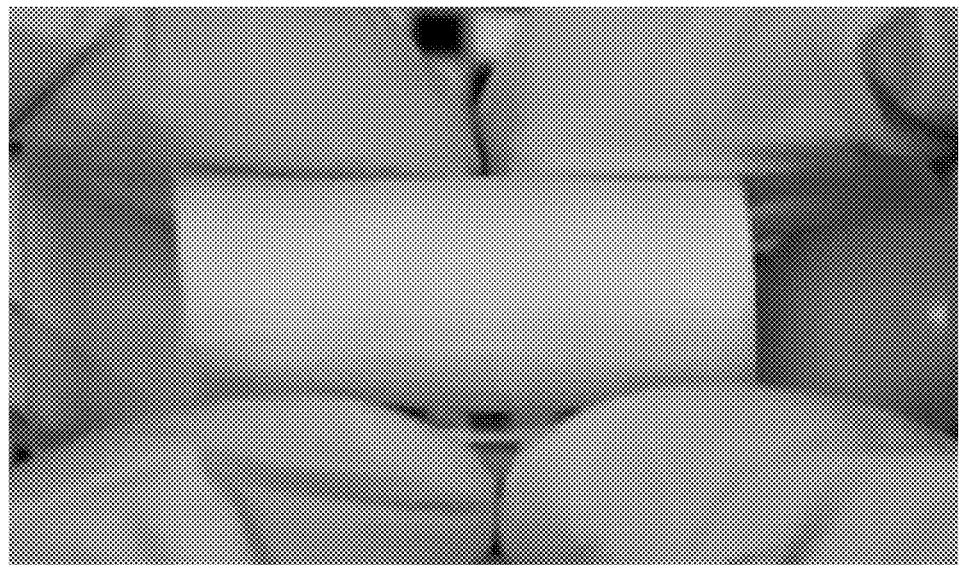
FIG. 20A shows bending of an exemplary dynamic SLIPS membrane and the corresponding pressure changes predicted by finite element modeling in accordance with certain embodiments.
Figure 20A:
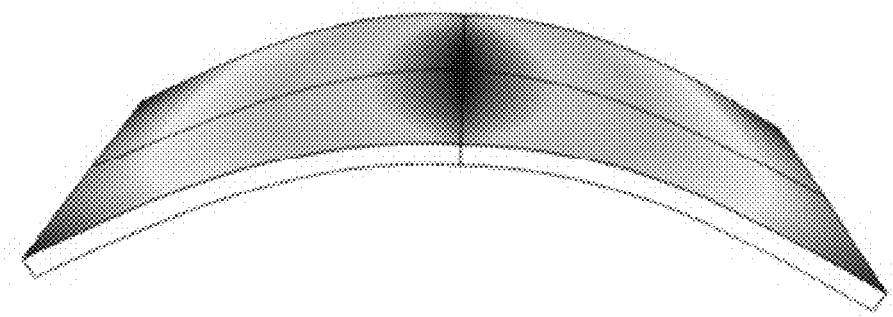
Figure 20B:
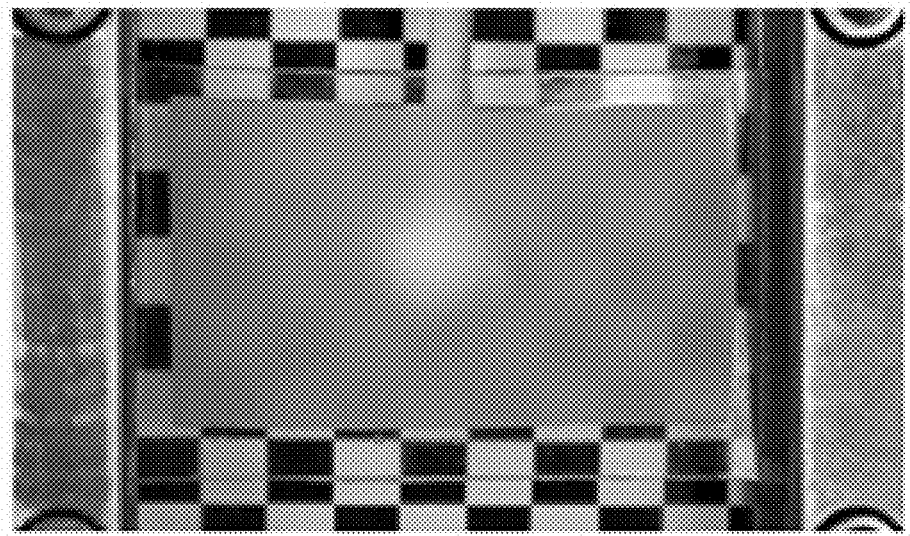
FIG. 20B shows poking of an exemplary dynamic SLIPS membrane and the corresponding pressure changes predicted by finite element modeling in accordance with certain embodiments.
Figure 20B:
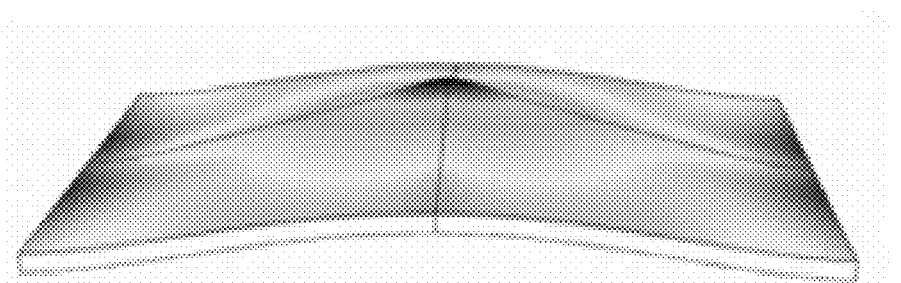
Figure 20C:
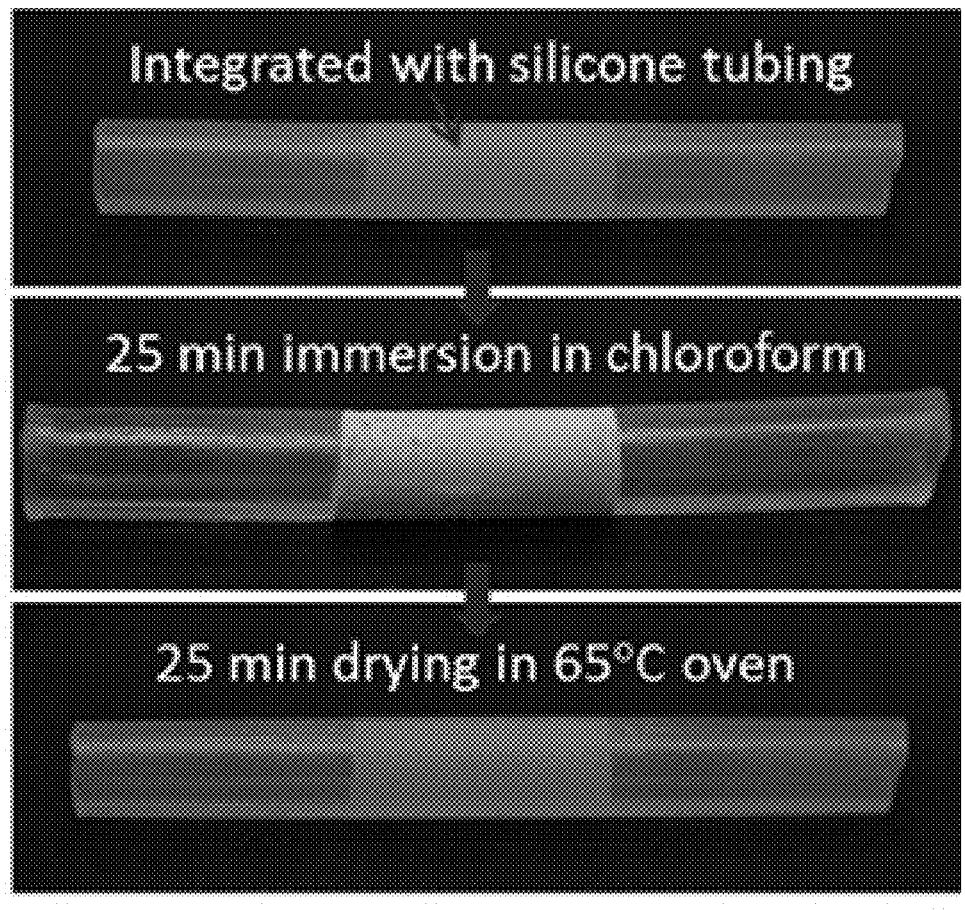
FIG. 20C shows reversible swelling and drying of an infused substrate attached to silicone tubing in accordance with certain embodiments.
Figure 20D:
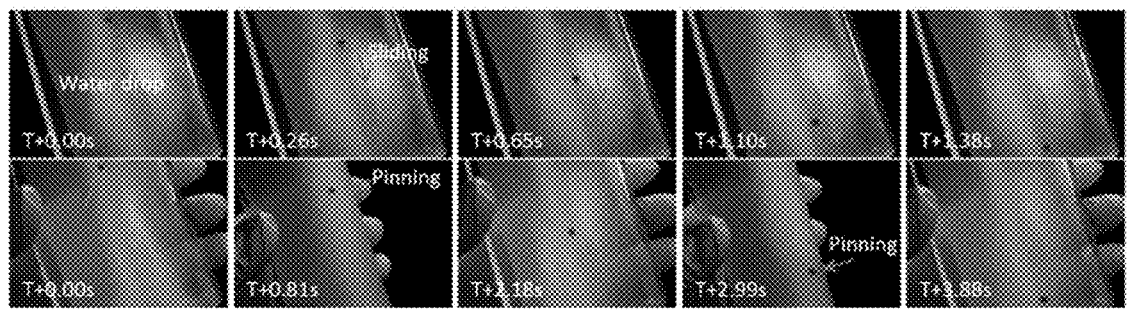
FIG. 20D shows comparison of water drops (9 μL, dyed with Rhodamine B) sliding on a slippery surface without (upper row) and with (lower row) bending. The membrane was tilted ~60° in accordance with certain embodiments.
Figure 20E:
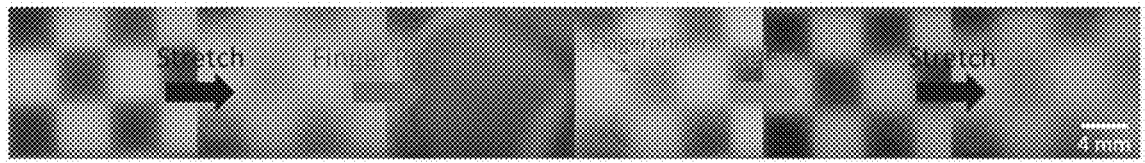
FIG. 20E shows the anti-fingerprint ability of the dynamic SLIPS structure. The fluid flows back and fills the gaps made by the fingerprint, indicating a self-healing mechanism in accordance with certain embodiments.

In addition to planar strain, in some embodiments more complex and localized deformations and the associated changes in the material's properties are induced by bending, poking, or swelling the liquid-infused elastic membrane (see FIGS. 20A to 20C). For example, sliding water drops slow down and stop when the membrane is bent, and resume moving as the membrane is released (see FIG. 20D). Compared to stretching, bending generates a sharper response in a localized area, and thus allows the fast and efficient control of liquids from low-surface-energy oils to water. FIG. 20C shows optical switching of a liquid-infused membrane attached to silicone tubing by reversible swelling/drying in chloroform. The membrane becomes opaque as the tubing expands upon swelling, and recovers after drying. The fluidic nature of the infused liquid also enables the liquid-infused membrane to be used in applications such as anti-fingerprint surfaces. As shown in FIG. 20E, a fingerprint is left on the stretched surface when textural collapse is generated by finger pressure, while it disappears when the strain is relaxed and the liquid flows back and fills the gaps made by the fingerprint. The fluidic nature of the infused liquid provides a dynamic stamping/screening property by allowing self-healing of the liquid layer.

Moreover, the anisotropy in the surface topography induced by stretching, provides the way to add the directionality to the SLIPS function. For example, when the fibrous surface is stretched in one direction, the droplets move with different velocities along and perpendicular to this direction. They significantly slow down and eventually pin when moving in the direction perpendicular to the applied force, but their velocity is not be affected in the direction of the strain.

Example 4: Magneto-SLIPS

A magnetically-responsive omniphobic surface that is based on the principle of slippery liquid infused porous surface(s) (SLIPS), referred to herein as magneto-SLIPS, is described. Without wishing to be bound by theory, the magnetic responsiveness may arise from the fluorocarbon-based ferrofluid that infiltrates the porous surface. In the absence of a magnetic field, magneto-SLIPS functions as normal SLIPS; in the presence of a magnetic field, various shapes of ferrofluid form on magneto-SLIPS as the result of normal field instability of ferrofluid and make the surfaces capable of holding droplets of liquids at tilt angles as high as 90°, transporting liquid droplets and mixing them, pumping a continuous liquid flow along a tube, and controlling the friction and adhesion between a solid surface and a magneto-SLIPS.

The magneto-SLIPS has been designed such that it keeps the SLIPS behaviors in the absence of an external magnetic field. Fluorocarbon-based ferrofluid was chosen to provide immiscibility of the infiltrating liquid and the liquids to be repelled (water- or hydrocarbon-based liquids). Porous Teflon membranes (available from Sterlitech) or polyfluoro-alkylsilane-coated micro-structured epoxy-resin was selected as the solid substrates to allow the ferrofluids to preferentially wet the substrates.

Preferably, in the presence of a magnetic field, the ferrofluid has a desired saturation magnetization to allow the display of normal field instability and desired viscosity so that this surface deformation forms within a reasonable time scale (a few seconds). As discussed more fully below, the normal field instability refers to the formation of spikes (or peaks and valleys) on the surface of ferrofluids when a strong normal magnetic field is applied. In qualitative terms, a normal magnetic field with a strength exceeding certain threshold intensity creates patterns of spikes as a result of the minimization of the sum of gravitational, capillary, and magnetic energies.

Commercial neodymium magnets (K&J Magnets, surface field 1000-5000 Gauss), and commercial fluorocarbon-based ferrofluids NF3882 (Ferrotec, 400 Gauss, 40 cP, and volatility=72.3% at 100° C. for 1.5 h) and NF3914 (Ferrotec, 400 Gauss, 367 cP, and volatility=0.5% at 100° C. for 3.5 h) were utilized. In certain cases, the ferrofluids were diluted with Krytox 100 (DuPont, 13 cP, volatility=87% at 121° C. for 22 h) to give different geometries of surface deformation.

Figure 21:
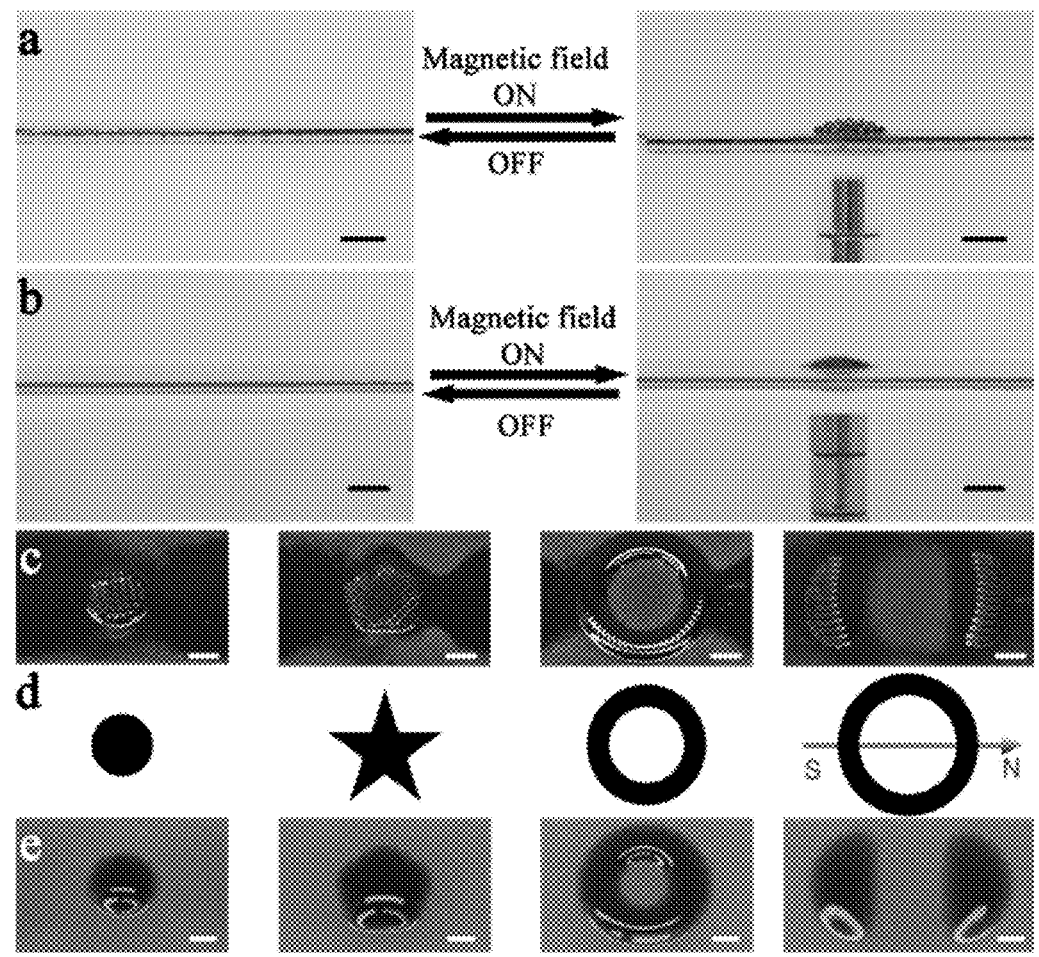
FIG. 21A to 21E show reversibility of the surface deformation and its various geometries using magnetic fields in accordance with certain embodiments.

The surface topography may depend on the concentration of the ferrofluid as well as the size, the shape, and the magnetization direction of the magnet. For example, as shown in FIG. 21A, when the ferrofluid is used without dilution (referred to in this example as the concentrated ferrofluid), the surface deformation takes the form of spikes. As shown in FIG. 21B, when the ferrofluid is diluted (referred to in this example as the diluted ferrofluid), the surface deformation takes the form of a bump. Moreover, as shown in FIGS. 21C-21E, the geometries of the surface deformation are further varied by varying the geometries and the magnetization directions of the magnets.

The formation of spikes and bumps are reversible. For example, when the magnet is removed, the surface becomes flat within seconds. As shown in FIG. 21C, the formation of spikes draws ferrofluid from nearby regions and reveals the porous solid substrate, as evident by a higher brightness as a result of diffuse reflection.

In addition, different geometries of surface deformation created by utilizing different shaped or magnetized magnets. As shown in FIGS. 21C to 21E, from left to right, axially magnetized disk magnets, star magnets, ring magnets and diametrically magnetized ring magnets form different surface topographies with both concentrated ferrofluid (see FIG. 21C) and diluted ferrofluid (see FIG. 21E). The magneto-SLIPS (porous Teflon membrane infiltrated with ferrofluid) were attached to glass slides with a double-sided Scotch tape. Scale bars are 2 mm.

One desired property of omniphobic surfaces is that the surface is slippery so that liquid droplets slide on them at small tilt angles. In the absence of a magnetic field, magneto-SLIPS maintain this "slippery" property. As shown in FIG. 22A, liquid droplets (5 µL) with various surface tensions slide at tilt angles smaller than 5°. In the presence of a magnetic field, however, magneto-SLIPS becomes non-slippery. For example, as shown in FIGS. 22B and 22C, water and decane droplets, respectively, are pinned at the spikes at about 90 degree tilt angle. Similarly, as shown in FIGS. 22D and 22E, water and hexadecane droplets, respectively, are stopped on ferrofluid-depleted areas at about 45 degree tilt angle. Alternatively, as shown in FIGS. 22F and 22G, water and pentane droplets, respectively, are held within rings of diluted ferrofluid at about 20 degree tilt angle.

Figure 22:
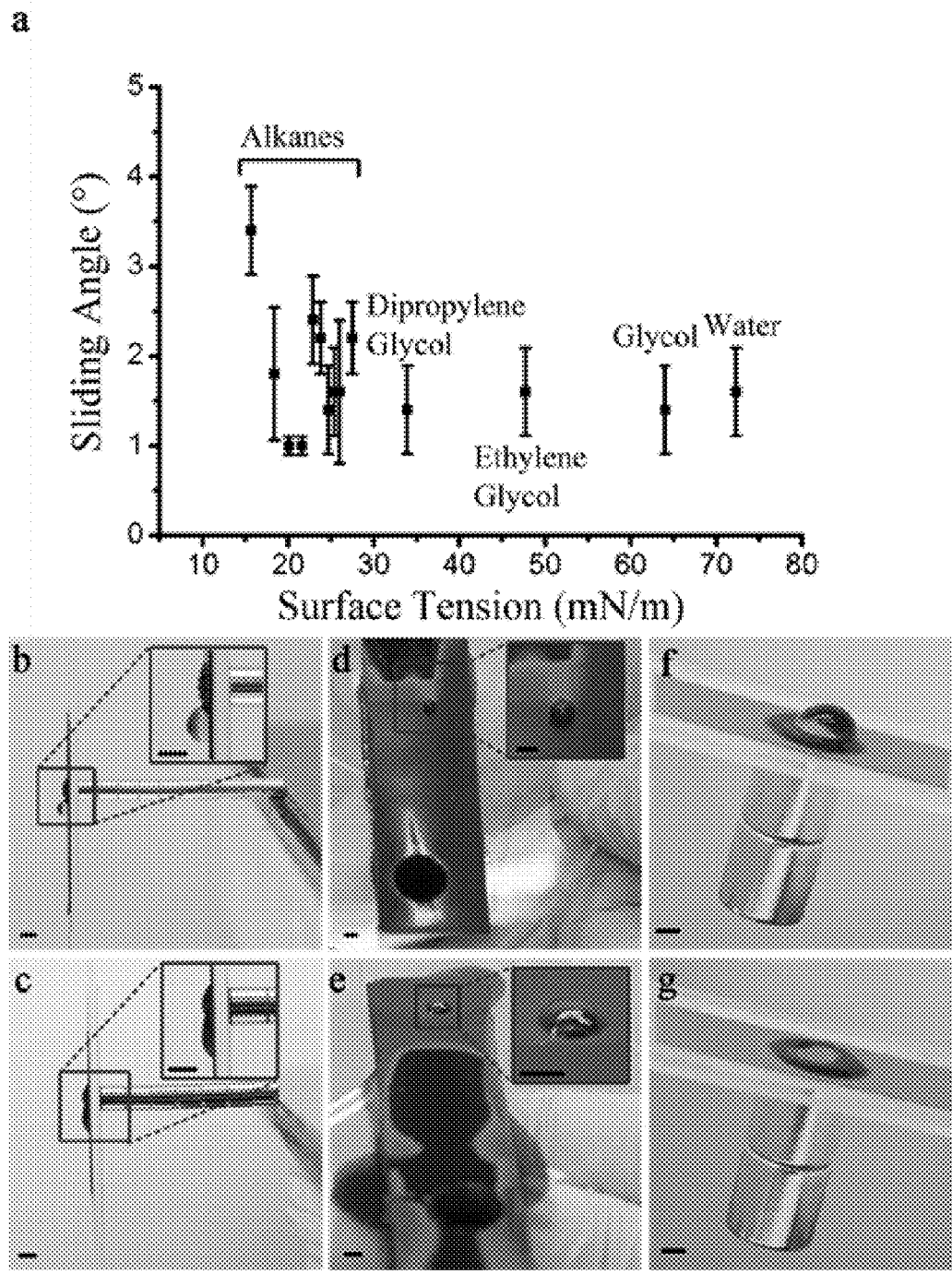
FIG. 22 A-G shows the slippery and non-slippery behaviors of liquid droplets on magneto-SLIPS in accordance with certain embodiments.

Except for the magneto-SLIPS shown in FIGS. 22D and 22E, the microstructure substrate used in FIG. 22 is porous Teflon membranes. The microstructured substrate used in FIGS. 22D and 22E is rows of 34-micron-tall and 2-micron-thick platelets separated by 40 microns. Scale bars are 2 mm.

Among all these non-slippery configurations, pinning at spikes achieves the highest tilt angles, up to 90° for both water and hydrocarbons. Without wishing to be bound by theory, the spikes may provide a liquid surface for droplets to adhere by capillary force, and this capillary force may act parallel to the substrate surface and counter the gravity of the droplets.

Moreover, the water droplet is colored yellow and the decane droplet is colored black. These colors suggest a thin layer of ferrofluid that wraps the droplet. Without wishing to be bound by theory, this wrapping layer of ferrofluid may produce an effective magnetic force that also contributes to the pinning of droplets.

Another way to stop a liquid droplet from sliding is to move the liquid droplets to the regions where the ferrofluid is depleted due to the formation of spikes. Yet another way is to use ring-shaped surface deformation to contain the droplets of large volumes. In all configurations, once the magnetic field is removed, the slippery property of magneto-SLIPS is restored.

The analysis of the pinning of droplets on magneto-SLIPS reveals two interfacial phenomena.

Figure 23:
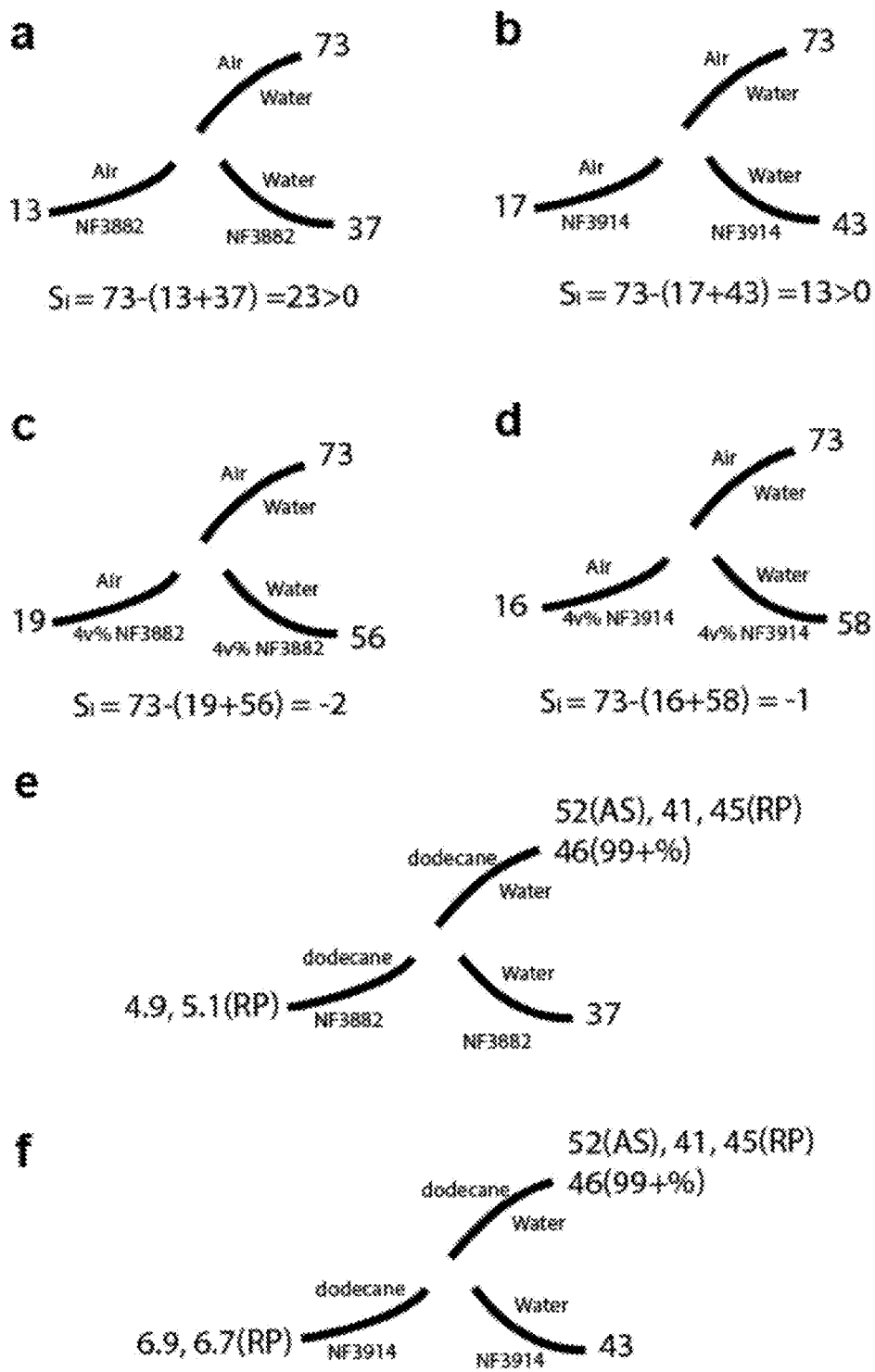
FIG. 23 A-F shows the calculation of initial spreading coefficient in accordance with certain embodiments.

First, when a water droplet is placed on magneto-SLIPS, a layer of ferrofluid is observed to spontaneously wrap around it. The initial spreading coefficient was calculated. As shown in FIG. 23, the ferrofluids are NF3882, NF3914, 4 v % NF3882 in Krytox 100, and 4 v % NF3914 in Krytox 100. AS (Analytical Standard>99.8%) and RP (Reagent Plus>99%) are from Sigma-Aldrich. 99+% is from Alpha Aesar. In the case of air-water-ferrofluid, surface tension dominates, and the initial spreading coefficient, written as $S_i = \sigma_{air-water} - (\sigma_{air-ferrofluid} + \sigma_{ferrofluid-water})$, is positive, which corresponds to spreading (see FIGS. 23A and 23B). However, if dodecane is added to replace air, this layer of ferrofluids unwraps spontaneously, even though the calculation of $S_i$ gives ambiguous results (see FIGS. 23E and 23F). Because the capillary lengths of ferrofluid interfaces (see Table 2) are less than the size of the water droplets used (~2.7 mm), full account of the wrapping and unwrapping phenomena is expected to include the effect of gravity.

TABLE 2

Capillary Lengths of Ferrofluid Interfaces

| Interfaces | Surface Tension (mN/m) | Density Difference (g/cm$^3$) | Capillary Length (mm) |
|---|---|---|---|
| Water-air | 74 | 1.0 | 2.7 |
| NF3882-air | 13 | 1.8 | 0.9 |
| NF3914-air | 17 | 1.9 | 1.0 |
| NF3882-water | 37 | 0.8 | 2.2 |
| NF3914-water | 43 | 0.9 | 2.2 |
| NF3882-dodecane | 5 | 0.8 | 0.8 |
| NF3914-dodecane | 7 | 0.9 | 0.9 |

Note 1:
Capillary lengths are calculated according to $l_c = \sqrt{\gamma/\Delta\rho \cdot g}$, or the root square of the interfacial tension over the product of density difference and standard gravity acceleration).

Figure 24:
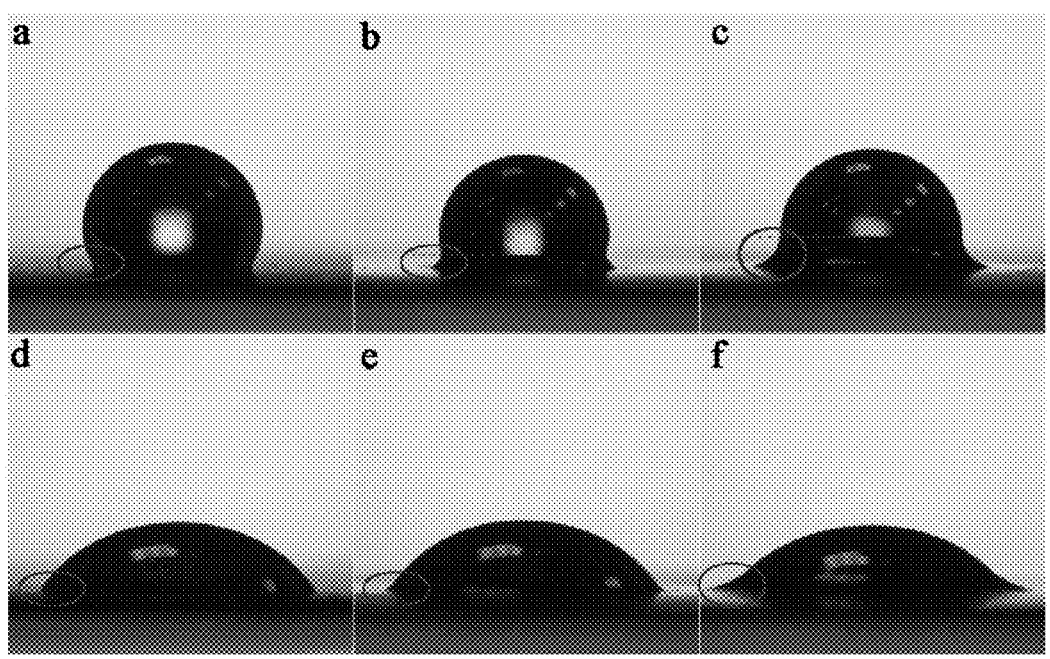
FIGS. 24A to 24C shows the fillets of a water droplet in air in accordance with certain embodiments.
FIGS. 24D to 24F shows the fillets of a decane droplet in air in accordance with certain embodiments.

Second, a fillet is observed to form at the three-phase contact line. Without wishing to be bound by theory, the fillet, observed at the three-phase contact line of a droplet (see FIG. 24), is likely the result of the force balance in both in-plane and out-of-plane directions. To explain this phenomenon, the concept of a soft substrate is employed, which describes the situation between the extreme of Young's Law for a solid (infinitely hard) substrate and the extreme of Neumann's triangle for a liquid (infinitely soft) substrate. The liquid component of the magneto-SLIPS, the ferrofluid, deforms easily whereas the solid component of the magneto-SLIPS, the porous structure, deform relatively little if at all. As a result, the more the ferrofluid, the larger the fillet, as evidenced in FIG. 24. Both the wrapping layer and the fillet render the liquid droplet slightly magnetic and hence make the droplets attracted to a magnet.

In some embodiments, not only does magneto-SLIPS make liquid droplets stationary, it is also used to move them and position them. Magnetic attraction between a droplet and a magnet (as explained in the previous paragraph) offers one way to move a droplet, but it may be more convenient to use the movement of the surface deformation to drag or push liquid droplets.

Figure 25:
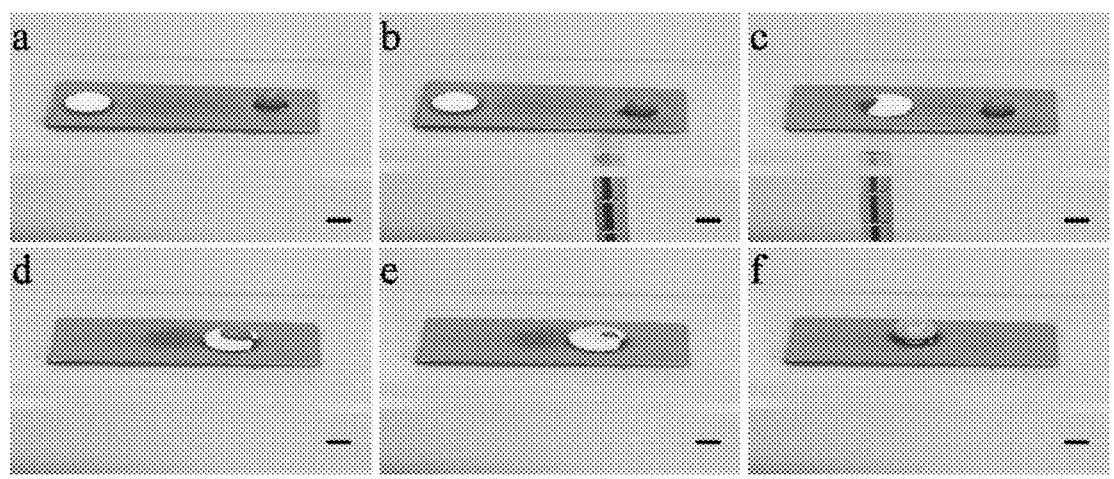
FIG. 25 A-F shows moving and mixing droplets of polystyrene colloids in ethanol (white) and in water (dyed with Rhodamine B) in accordance with certain embodiments.

An exemplary embodiment of this capability is shown in FIG. 25, which shows transporting and mixing of polystyrene colloidal dispersion in ethanol and in water (dyed with Rhodamine B). The size of the bump is comparable to the sizes of the two droplets. It was found that for droplets of low surface tension liquid (22 mN/m for ethanol), it was more effective to move the droplet by pushing it with a bump, whereas for droplets of high surface tension liquid (73 mN/m for water), dragging a droplet was an easier way to control the direction of movement than pushing the droplet.

Figure 26:
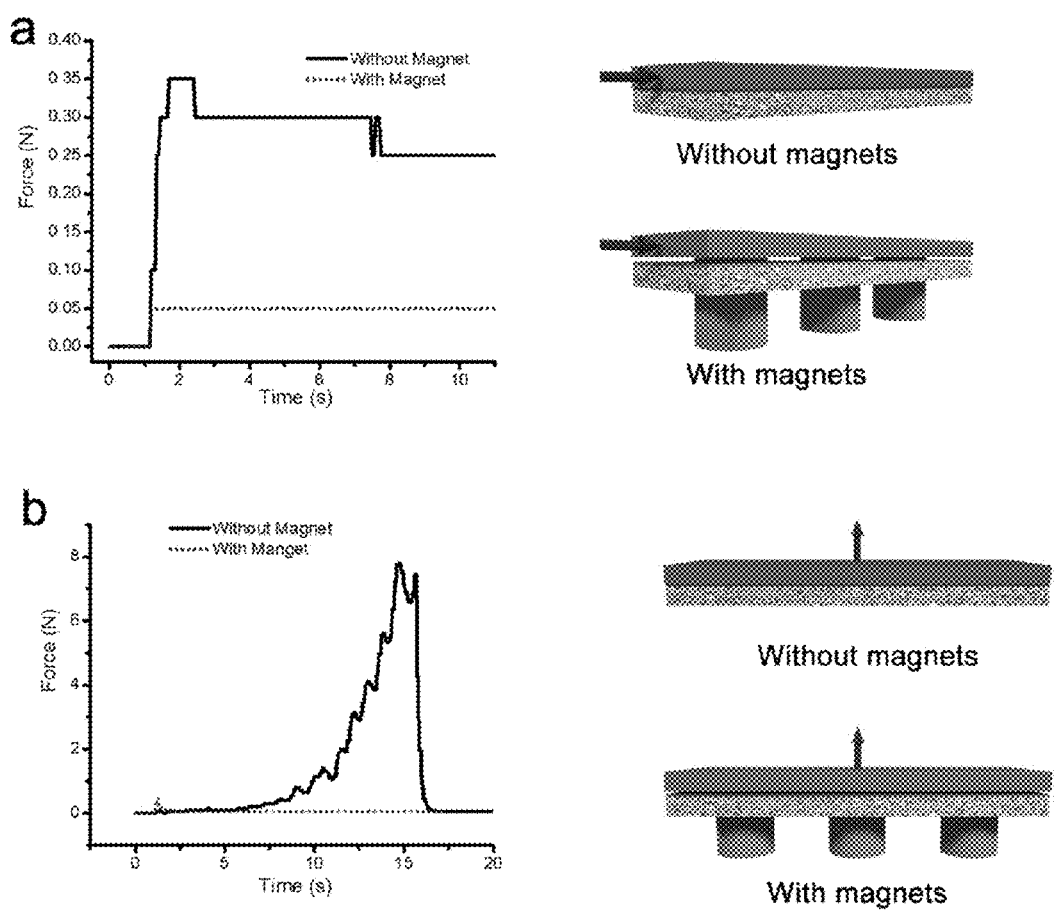
FIG. 26 A-B shows friction and adhesion control by comparing the forces needed to push or separate a glass slide on or from a magneto-SLIPS with and without magnets in accordance with certain embodiments.

In addition to manipulating liquids, in some embodiments magneto-SLIPS is also used to control the interaction of a solid surface in contact with it. This ability was demonstrated by switching the friction and adhesion of a glass slide on a magneto-SLIPS, as shown in FIG. 26.

For friction, as shown in FIG. 26A, the force required to push a glass slide along a planar magneto-SLIPS without magnets is six to seven times higher than with magnets. The size of the glass slide is 2.54 cm by 7.62 cm. Once the glass slide starts to move, the speed of the pushing is 2.5 mm/s. The force gauge utilized had a sensitivity of 0.05N and was incapable of measuring the difference between static and kinetic friction when magnets are present.

For adhesion, as shown in FIG. 26B, the force required to pull the glass slide apart from magneto-SLIPS without magnets is one order of magnitude higher than with magnets. The zigzag-shaped increase in the force in the absence of magnets is due to the difficulty in applying a strictly out-of-plan force. Any tangential force moves the glass slide parallel to the surface of magneto-SLIPS. The actual force required to pull away the glass slide may be even higher than the value measured here.

Figure 27:
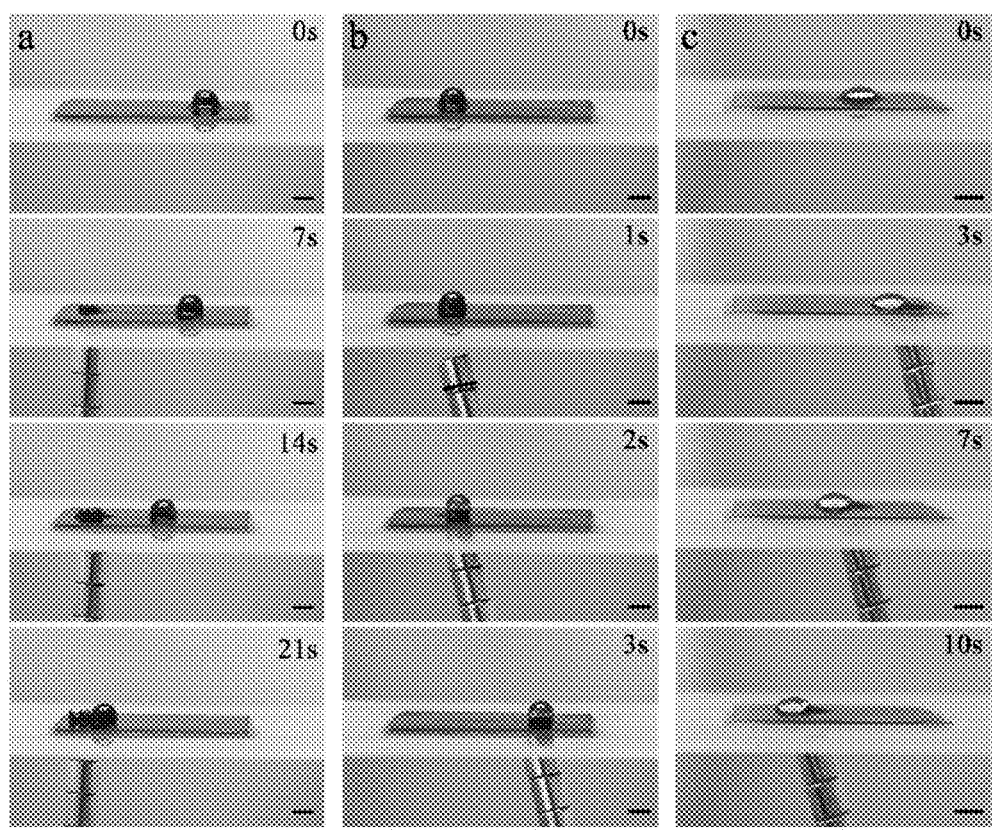
FIG. 27 A-C shows moving of different droplets using attracting, dragging, and pushing in accordance with certain embodiments.

Additional methods to move a droplet on magneto-SLIPS can be envisioned. In some instances, such as shown in FIG. 27A, water droplets are attracted with a magnet placed at small distances. In other instances, as shown in FIG. 27B, water droplet is dragged along with the spikes formed on the ferrofluid. In other instances, as shown in FIG. 27C, a droplet of hydrocarbon is pushed with a bump of diluted ferrofluid. Scale bars in FIG. 27 are 2 mm.

Figure 28:
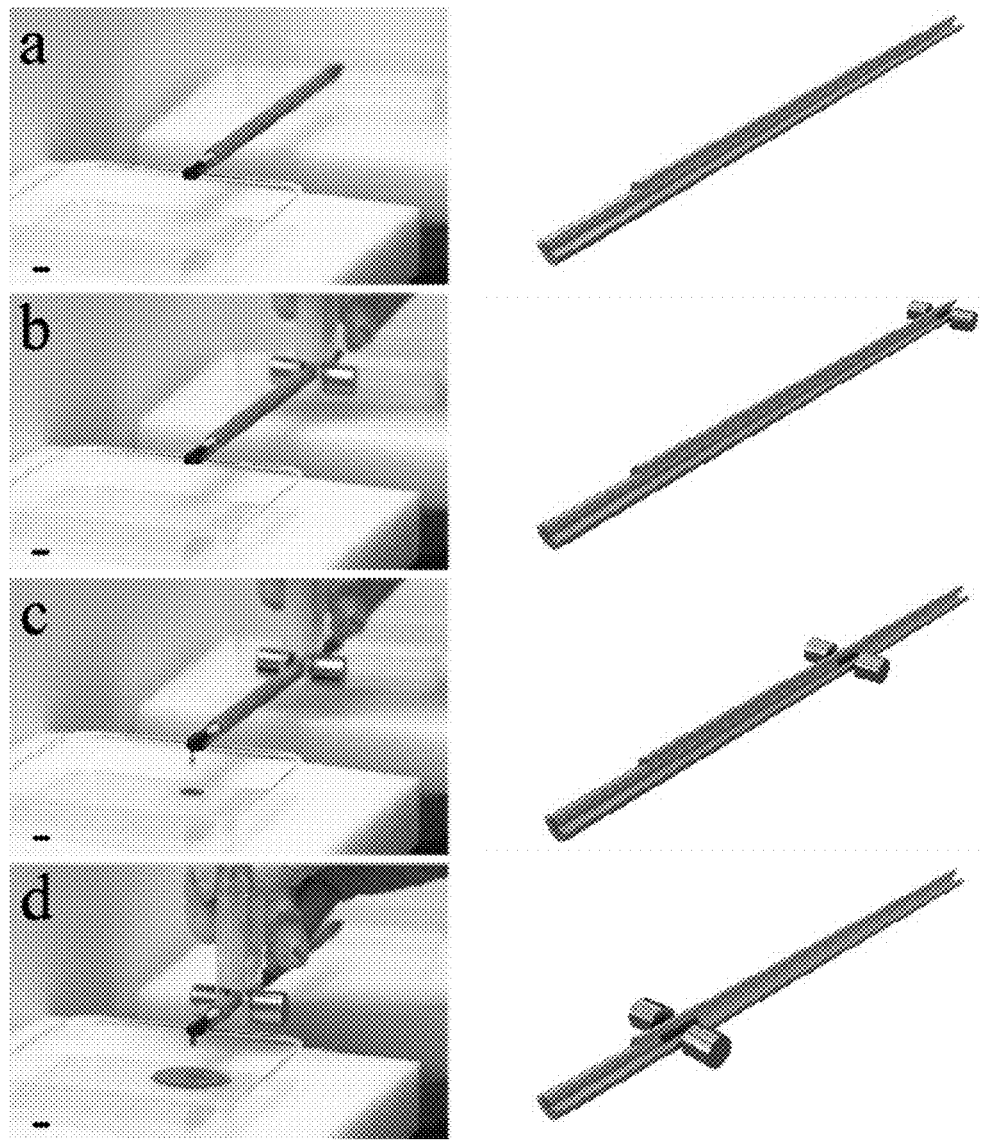
FIG. 28 A-D shows pumping of a liquid (ethanol dyed with Rhodamine B) along a Teflon tube infiltrated with ferrofluid in accordance with certain embodiments.

Besides droplets of liquid, the surface deformation, when confined in a tube, enables magneto-SLIPS to handle liquid in a continuous flow. As shown in FIG. 28, this capability was demonstrated by pumping a continuous flow of ethanol along a tube of magneto-SLIPS. The bump created by the magnet forms a plug inside the tube, and by moving the magnets the plug pushes out the ethanol. The inside diameter of the tube is ~2 mm, and the wall thickness of the tube is ~0.9 mm. Scale bars are 1 cm. The thick wall ensures that there is enough ferrofluid to form the plug locally without affecting the slippery properties of the tube elsewhere.

Example 5: Thermo-Responsive SLIPS

Figure 29:
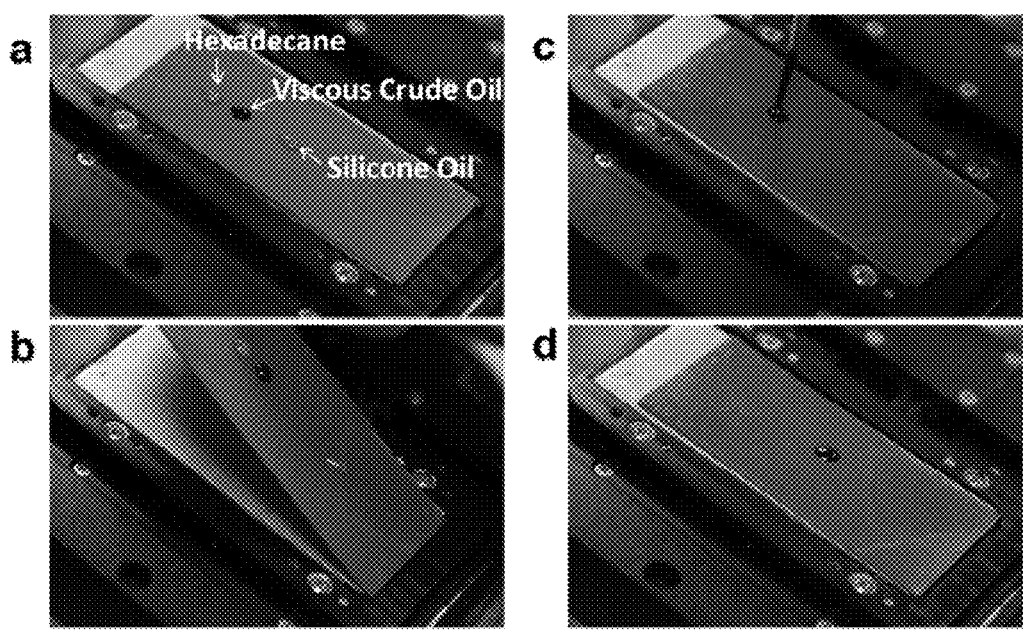
FIG. 29 A-D shows an example of controlled droplet mobility on thermal-responsive dynamic SLIPS that changes its properties upon lubricant melting.

FIG. 29 shows an example of controlled droplet mobility on thermo-responsive dynamic SLIPS that changes its properties upon lubricant melting. In FIGS. 29A-B, oil drops (hexadecane, crude oil and silicone oil, 9 mL) are pinned on a tilted substrate made from a sand-blasted copper sheet covered with a porous Teflon (200 nm average pore size, Sterilitech) that was infused with Perfluorodecane-pinane wax (Fluoryx Inc.). The temperature of the substrate was kept at 65° C. FIGS. 29C-D show the sliding of the crude oil on the same substrate when the temperature increased to 80° C., at which the wax melted to liquid, making the surface slippery. The tilt angle of the substrate is 15° in FIG. 29A and FIGS. 29C-D, and 35° in FIG. 29B, respectively.

Figure 30:
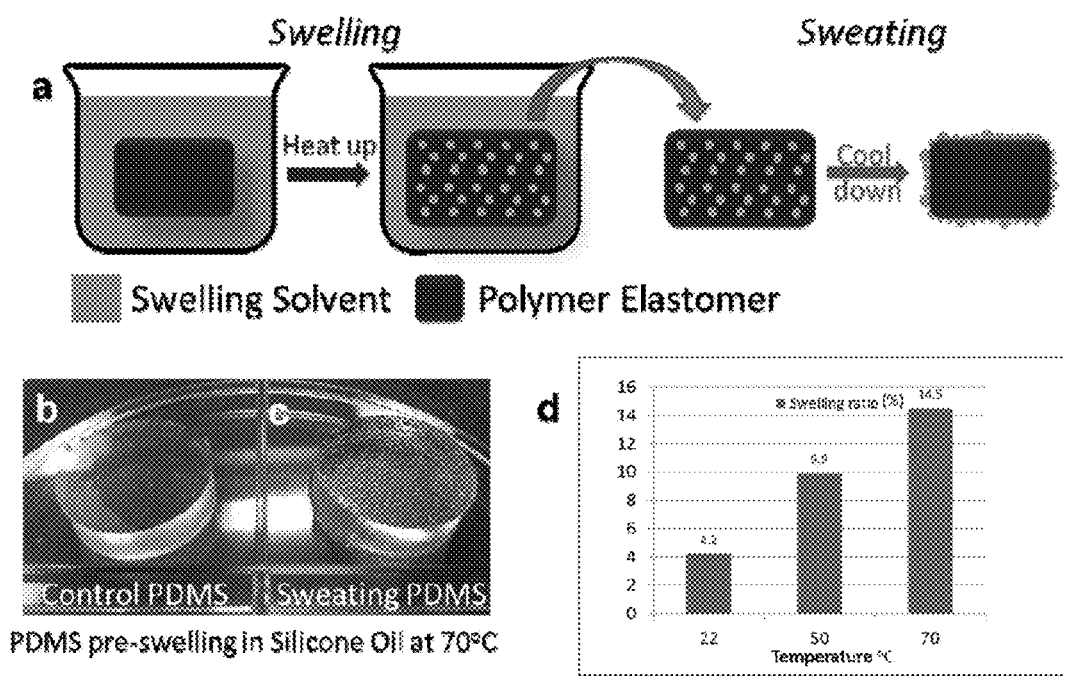
FIG. 30 A-D shows a schematic representation and the performance characteristics of an exemplary dynamic SLIPS that utilizes inclusions of lubricant that "sweat" out upon temperature changes

FIG. 30A shows a schematic representation and the performance characteristics of an exemplary dynamic SLIPS that utilizes inclusions of lubricant that "sweat" out upon temperature changes utilizing the thermal enhanced swelling ability of polymeric elastomer. When the elastomer is swollen in the presence of a solvent lubricant B, it becomes impregnated with the inclusions of the lubricant. The elastomer adsorbs more lubricant at higher temperature and "sweats" the excess lubricant inclusions when the temperature cools down. FIG. 30B shows a control PDMS elastomer (Dow Corning, 10:1) without the impregnated lubricant, comparing to the "sweating" PDMS surface shown in FIG. 30C. Here, a polydimethylsiloxane Silicone Oil (Aldrich) was used as solvent/lubricant. The PDMS plate was preswollen in the Silicone Oil at 70° C. for 48 hours, then cooled down at room temperature, during which the Silicone Oil will is released to coat the surface and produce SLIPS. FIG. 30D shows the swelling ratio in relation to temperature for PDMS in the Silicone Oil.

Figure 31:
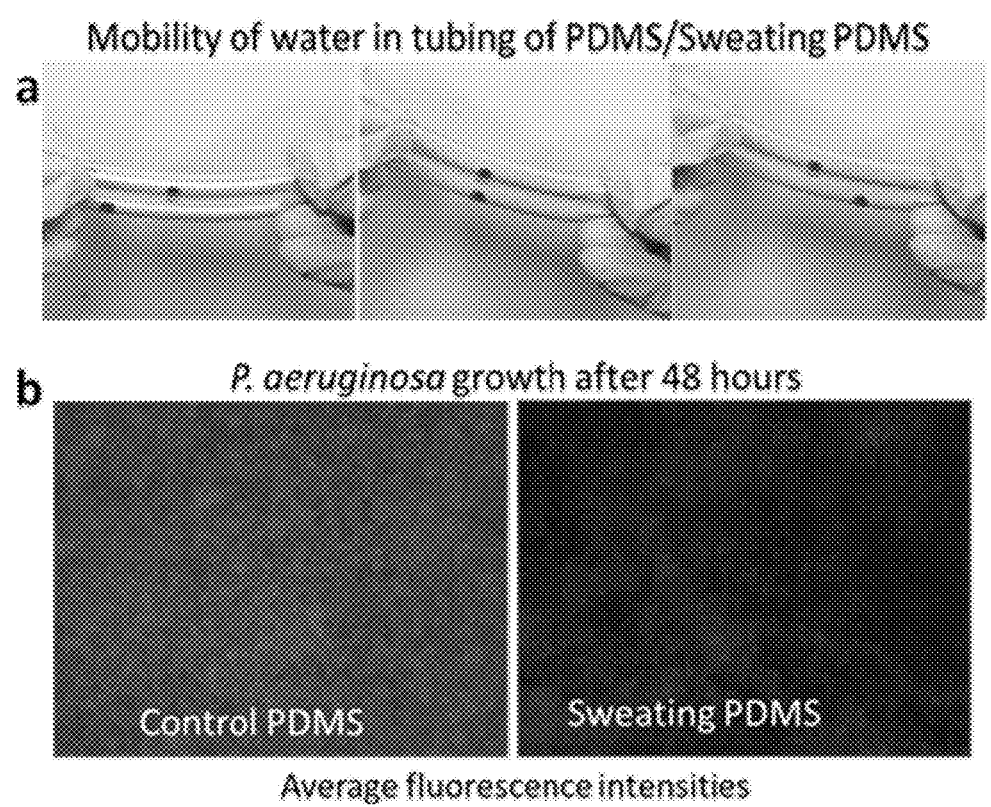
FIG. 31A shows the demonstration of the "Sweating surface" in the application of liquid transportation.
FIG. 31B shows the demonstration of the "Sweating surface" in the anti-biofilm application.

FIG. 31A shows the demonstration of the "Sweating surface" in the application of liquid transportation by showing a comparison for the liquid slippery ability of a normal Silicone tubing (upper) and a "Sweating" Silicone tubing (lower). A dyed water drop can slide easily inside the "Sweating" tubing but be pinned in the normal tubing. FIG. 31B shows the demonstration of the "Sweating surface" in the anti-biofilm application by showing average fluorescence intensities (brightness) for the comparison for the anti-biofilm of a normal Silicone surface (left) and a "Sweating" Silicone surface (right). Both the surfaces were immersed in a growth medium of *P. aeruginosa* for 48 hours, after which the bacteria attachments were tested. The "Sweating" PDMS surface displayed an average 40% reduction for bacteria attachment.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of altering one or more characteristics of a structure, the method comprising:
   providing a structure comprising a roughened surface which is optionally functionalized to immobilize a lubricating liquid, wherein the lubricating liquid wets and adheres to the roughened surface to form a layer having a smooth planar upper surface over the roughened surface to obtain a first characteristic of the structure; and
   applying or removing a first stimulus to the structure, wherein the application or removal of the first stimulus exposes a portion of the underlying substrate or disrupts the smoothness and/or planarity of the upper surface of the lubricating liquid layer to obtain a second characteristic of the structure;
   wherein:
   the first stimulus comprises heat and wherein the heat stimulus causes temperature-induced melting of a solid lubricant or a change in viscosity of the lubricant; and
   the first stimulus is selected to alter the shape, volume or configuration of the underlying substrate, such that the underlying substrate is exposed when the underlying substrate is in an expanded or contracted state.

2. The method of claim 1, wherein the one or more characteristics comprise at least one of optics, transparency, wettability, adhesion to a first substance which optionally contacts the surface, repellency of a first liquid which optionally contacts the surface or mobility of a first liquid which optionally contacts the surface.

3. The method of claim 1, wherein the change from the first characteristic of the structure to the second characteristic of the structure occurs gradually or over a continuum.

4. The method of claim 1, wherein the change from the first characteristic of the structure to the second characteristic of the structure occurs abruptly or completely.

5. The method of claim 1, wherein the change from the first characteristic of the structure to the second characteristic of the structure is irreversible or reversible, by removal or reduction of the first stimulus or application of a second stimulus.

6. The method of claim 1, wherein the underlying substrate comprises a shape-changing thermal responsive polymer that undergoes a shape, volume or configuration change upon thermal stimulus.

7. The method of claim 5, wherein the lubricating liquid comprises additives that respond to the first stimulus.

8. The method of claim 7, wherein the additives comprises a gelling or polymerization agent and the first stimulus induces polymerization or gelling of the lubricant.

9. A method of altering one or more characteristics of a structure, the method comprising:
providing a structure comprising a roughened surface which is optionally functionalized to immobilize a lubricating liquid, wherein the lubricating liquid wets and adheres to the roughened surface to form a layer having a smooth planar upper surface over the roughened surface to obtain a first characteristic of the structure; and
applying or removing a first stimulus to the structure, wherein the application or removal of the first stimulus exposes a portion of the underlying substrate or disrupts the smoothness and/or planarity of the upper surface of the lubricating liquid layer to obtain a second characteristic of the structure;
wherein:
the first stimulus comprises heat and wherein the heat stimulus causes temperature-induced melting of a solid lubricant or a change in viscosity of the lubricant; and
the surface comprises a plurality of deflectable aspected features and the first stimulus is selected to deflect the aspected features from a first position in which the aspected features are above the lubricant layer to a second position in which the aspected features are below the lubricant layer or vice versa.

10. A method of altering one or more characteristics of a structure, the method comprising:
providing a structure comprising a roughened surface which is optionally functionalized to immobilize a lubricating liquid, wherein the lubricating liquid wets and adheres to the roughened surface to form a layer having a smooth planar upper surface over the roughened surface to obtain a first characteristic of the structure; and
applying or removing a first stimulus to the structure, wherein the application or removal of the first stimulus exposes a portion of the underlying substrate or disrupts the smoothness and/or planarity of the upper surface of the lubricating liquid layer to obtain a second characteristic of the structure;
wherein:
the first stimulus comprises heat and wherein the heat stimulus causes temperature-induced melting of a solid lubricant or a change in viscosity of the lubricant; and
the first stimulus is selected to degrade the underlying substrate surface to reduce the affinity of the lubricant for the surface.

11. The method of claim 5, wherein the first stimulus is selected to degrade the lubricant to reduce the affinity of the lubricant for the surface.

12. The method of claim 5, wherein the first stimulus is selected to reduce the shape, volume or configuration of the lubricant to expose the underlying substrate.

13. The method of claim 1, wherein the removal of the first stimulus and/or the application of a second stimulus re-obtains the first characteristic of the structure.

14. The method of claim 9, wherein the one or more characteristics comprise at least one of optics, transparency, wettability, adhesion to a first substance which optionally contacts the surface, repellency of a first liquid which optionally contacts the surface or mobility of a first liquid which optionally contacts the surface.

15. The method of claim 9, wherein the change from the first characteristic of the structure to the second characteristic of the structure occurs gradually or over a continuum.

16. The method of claim 9, wherein the change from the first characteristic of the structure to the second characteristic of the structure occurs abruptly or completely.

17. The method of claim 9, wherein the change from the first characteristic of the structure to the second characteristic of the structure is irreversible or reversible, by removal or reduction of the first stimulus or application of a second stimulus.

18. The method of claim 9, wherein the underlying substrate comprises a shape-changing thermal responsive polymer that undergoes a shape, volume or configuration change upon thermal stimulus.

19. The method of claim 9, wherein the lubricating liquid comprises additives that respond to the first stimulus.

20. The method of claim 19, wherein the additives comprises a gelling or polymerization agent and the first stimulus induces polymerization or gelling of the lubricant.

21. The method of claim 9, wherein the first stimulus is selected to degrade the lubricant to reduce the affinity of the lubricant for the surface.

22. The method of claim 9, wherein the first stimulus is selected to reduce the shape, volume or configuration of the lubricant to expose the underlying substrate.

23. The method of claim 9, wherein the removal of the first stimulus and/or the application of a second stimulus re-obtains the first characteristic of the structure.

24. The method of claim 10, wherein the one or more characteristics comprise at least one of optics, transparency, wettability, adhesion to a first substance which optionally contacts the surface, repellency of a first liquid which optionally contacts the surface or mobility of a first liquid which optionally contacts the surface.

25. The method of claim 10, wherein the change from the first characteristic of the structure to the second characteristic of the structure occurs gradually or over a continuum.

26. The method of claim 10, wherein the change from the first characteristic of the structure to the second characteristic of the structure occurs abruptly or completely.

27. The method of claim 10, wherein the change from the first characteristic of the structure to the second characteristic of the structure is irreversible or reversible, by removal or reduction of the first stimulus or application of a second stimulus.

28. The method of claim 10, wherein the underlying substrate comprises a shape-changing thermal responsive polymer that undergoes a shape, volume or configuration change upon thermal stimulus.

29. The method of claim 10, wherein the lubricating liquid comprises additives that respond to the first stimulus.

30. The method of claim 29, wherein the additives comprises a gelling or polymerization agent and the first stimulus induces polymerization or gelling of the lubricant.

31. The method of claim 10, wherein the first stimulus is selected to degrade the lubricant to reduce the affinity of the lubricant for the surface.

32. The method of claim 10, wherein the first stimulus is selected to reduce the shape, volume or configuration of the lubricant to expose the underlying substrate.

33. The method of claim 10, wherein the removal of the first stimulus and/or the application of a second stimulus re-obtains the first characteristic of the structure.

* * * * *